United States Patent
Carling et al.

(10) Patent No.: US 6,310,203 B1
(45) Date of Patent: Oct. 30, 2001

(54) PRECURSOR COMPOUNDS TO SUBSTITUTED 1,2,4-TRIAZOLO[3,4,-A] PHATHALAZINE GABA ALPHA 5 LIGANDS

(75) Inventors: William Robert Carling, Bishops Stortford; Tamara Ladduwahetty, London; Angus Murray MacLeod, Bishops Stortford; Kevin John Merchant, Stevennge; Kevin William Moore, Bundngford; Francine Sternfeld, London; Leslie Joseph Street, Harlow, all of (GB)

(73) Assignee: Merck Sharpe & Dohme Limited, Hoddesdon (GB)

( * ) Notice: Subject to any disclaimer, the term of this patent is extended or adjusted under 35 U.S.C. 154(b) by 0 days.

(21) Appl. No.: 09/547,216

(22) Filed: Apr. 11, 2000

Related U.S. Application Data

(62) Division of application No. 09/180,623, filed as application No. PCT/GB98/01307 on May 6, 1998, now Pat. No. 6,200,975.

(30) Foreign Application Priority Data

| May 8, 1997 | (GB) | 9709368 |
| Jul. 10, 1997 | (GB) | 9714508 |
| Nov. 11, 1997 | (GB) | 9723741 |
| Feb. 25, 1998 | (GB) | 9803992 |

(51) Int. Cl.[7] .............................................. C07D 487/04
(52) U.S. Cl. .............................................. 544/234
(58) Field of Search .............................................. 544/234

(56) References Cited

U.S. PATENT DOCUMENTS

| 4,788,186 | 11/1988 | Occelli et al. | 514/218 |
| 5,145,684 | 9/1992 | Liversidge et al. | 424/489 |
| 5,182,290 | 1/1993 | Albaugh | 514/293 |
| 5,212,310 | 5/1993 | Thurkauf et al. | 544/251 |
| 5,306,819 | 4/1994 | Albaugh et al. | 544/346 |

FOREIGN PATENT DOCUMENTS

| 19617 862 | 4/1996 | (DE) . |
| 85840 | * 8/1983 | (EP) . |
| 0 085 840 | 8/1983 | (EP) . |
| 0 134 946 | 3/1985 | (EP) . |
| WO96/25948 | 8/1996 | (WO) . |
| WO98 04559 | 2/1998 | (WO) . |
| WO98/04560 | 2/1998 | (WO) . |
| WO98/50385 | 11/1998 | (WO) . |

OTHER PUBLICATIONS

Cai, D., et al., Tetrahedron Lett., 15:2537–2540 (1996).
Holzer, W., et al., J. Heterocyclic. Chem., 29:1203–1207 (1992).
McNamara, R.K., et al., Psychobiology, 21:101–108 (1993).
Tarzia, et al., Il Farmaco—Ed. Sc., 43:189–201 (1987).

* cited by examiner

*Primary Examiner*—Richard L. Raymond
*Assistant Examiner*—Deepak R. Rao
(74) *Attorney, Agent, or Firm*—Shu Muk Lee; David L. Rose

(57) ABSTRACT

Substituted 1,2,4-Triazolo[3,4-A]phthalazine derivatives that are GABA Alpha 5 ligands are prepared from compounds represented by the formula:

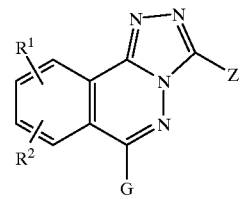

in which $R^1$ is hydrogen, halogen, $CF_3$, $OCF_3$, CN or an optionally substituted $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy group; $R^2$ is hydrogen, halogen, $CF_3$, $OCF_3$, CN or an optionally substituted $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy group; Z is an optionally substituted 5-membered or 6-membered heteroaromatic ring; and G is a leaving group.

2 Claims, No Drawings

PRECURSOR COMPOUNDS TO SUBSTITUTED 1,2,4-TRIAZOLO[3,4,-A] PHATHALAZINE GABA ALPHA 5 LIGANDS

CROSS REFERENCE TO RELATED APPLICATIONS

This application is a divisional of U.S. application Ser. No. 09/180,623, filed Nov. 12, 1998, now U.S. Pat. No. 6,200,975 which claims priority from PCT Application No. PCT/GB98/01307, filed May 6, 1998, which claims priority from Great Britain Application No. 9709368.6, filed May 8, 1997, Great Britain Application No. 9714508.0, filed Jul. 10, 1997, Great Britain Application No. 9723741.6, filed Nov. 11, 1997, and Great Britain Application No. 9803992.8, filed Feb. 25, 1998.

The present invention relates to a class of substituted triazolopyridazine derivatives and to their use in therapy. More particularly, this invention is concerned with substituted 1,2,4-triazolo[3,4-a]pyridazine derivatives which are ligands for $GABA_A$ receptors containing the α5 subunit and are therefore useful in the therapy where cognition enhancement is required.

Receptors for the major inhibitory neurotransmitter, gamma-aminobutyric acid (GABA), are divided into two main classes: (1) $GABA_A$ receptors, which are members of the ligand-gated ion channel super family; and (2) $GABA_B$ receptors, which may be members of the G-protein linked receptor super family. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δ subunit also exists, but is apparently uncommon in the native receptor.

Studies of receptor size and visualization by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6γδ and α4βδ. Subtype assemblies containing an α1 subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness.

It has been reported by McNamara and Skelton in Psychobiology, 21:101–108, that the benzodiazepine receptor inverse agonist β-CCM enhanced spatial learning in the Morris watermaze. However, β-CCM and other conventional benzodiazepine receptor inverse agonists are proconvulsant or convulsant which makes it clear that they cannot be used as cognition enhancing agents in humans.

However, we have now discovered that it is possible to obtain medicaments which have cognition enhancing effects which may be employed with less risk of proconvulsant effects previously described with benzodiazepine receptor partial or full inverse agonists.

It has now been discovered that use of an α5 receptor partial or full inverse agonist which is relatively free of activity at α1 and/or α2 and/or α3 receptor binding sites can be used to provide a medicament which is useful for enhancing cognition but in which proconvulsant activity is reduced or eliminated. Inverse agonists at α5 which are not free of activity at α1 and/or α2 and/or α3 but which are functionally selective for α5 can also be used. Inverse agonists which are both selective for α5 and are relatively free of activity at α1, α2 and α3 receptor binding sites are preferred.

European Patent Applications 0085840 and 0134946 describe related series of 1,2,4-triazolo[3,4-a]phthalazine derivatives which are stated to possess antianxiety activity. However, there is no disclosure nor any suggestion in either of these publications of the compounds of the present invention, nor that the compounds disclosed in the Applications have any cognition enhancing properties.

The present invention provides a compound of the formula I:

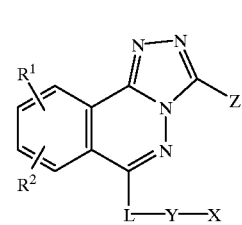

(I)

wherein:

$R^1$ is hydrogen, halogen or CN or a group $CF_3$, $OCF_3$, $C_{1-4}$alkyl, $C_{2-4}$alkenyl, $C_{2-4}$alkynyl, $C_{1-4}$alkoxy, $C_{2-4}$alkenyloxy or $C_2$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or $CF_3$ groups;

$R^2$ is hydrogen, halogen or CN or a group $CF_3$, $OCF_3$, $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms;

L is O, S or $NR''$ where $R''$ is H, $C_{1-6}$alkyl or $C_{3-6}$cycloalkyl;

X is a 5-membered heteroaromatic ring containing 1, 2, 3 or 4 heteroatoms independently chosen from oxygen, nitrogen and sulphur, at most one of the heteroatoms being oxygen or sulphur, or a 6-membered heteroaromatic ring containing 1, 2 or 3 nitrogen atoms, the 5- or 6-membered heteroaromatic ring being optionally fused to a benzene ring and the heteroaromatic ring being optionally substituted by $R^x$ and/or $R^y$ and/or $R^z$, where $R^x$ is halogen, $R^3$, $OR^3$, $OCOR^3$, $NR^4R^5$, $NR^4COR^5$, tri($C_{1-6}$alkyl)silyl$C_{1-6}$alkoxy$C_{1-4}$alkyl, CN or $R^9$, $R^y$ is halogen, $R^3$, $OR^3$, $OCOR^3$, $NR^4R^5$, $NR^4COR^5$ or CN and $R^z$ is $R^3$, $OR^3$ or $OCOR^3$, where $R^3$ is $C_{1-6}$alkyl, $C_{2-6}$alkenyl, $C_{2-6}$alkynyl, $C_{3-6}$cycloalkyl, hydroxy$C_{1-6}$alkyl and $R^3$ is optionally mono, di- or tri-fluorinated, $R^4$ and $R^5$ are each independently hydrogen, $C_{1-6}$alkyl, $C_{2-6}$alkenyl, $C_{2-6}$alkynyl, $C_{3-6}$cycloalkyl or $CF_3$ or $R^4$ and $R^5$, together with the nitrogen atom to which they are attached, form a 4–7 membered heteroaliphatic ring containing the nitrogen atom as the sole heteroatom, and $R^9$ is benzyl or an aromatic ring containing either 6 atoms, 1, 2 or 3 of which are optionally nitrogen, or 5 atoms, 1, 2 or 3 of which are independently chosen from oxygen, nitrogen and sulphur, at most one of the atoms being oxygen or sulphur, and $R^9$ is optionally substituted by one, two or three substituents independently chosen from halogen atoms and $C_{1-4}$alkyl $C_{2-4}$alkenyl $C_{2-4}$alkynyl, $C_{1-4}$alkoxy, $C_{2-4}$alkenyloxy and $C_{2-4}$alkynyloxy groups each of which groups is unsubstituted or substituted by one, two or three halogen atoms, and when X is a pyridine derivative, the pyridine derivative is optionally in the form of the N-oxide and providing that when X is a tetrazole derivative it is protected by a $C_{1-4}$alkyl group; or X is phenyl optionally substituted by one, two or three groups independently selected from halogen, cyano, $C_{1-6}$alkyl, $C_{2-6}$alkenyl, $C_{2-6}$alkynyl and $C_{3-6}$cycloalkyl;

Y is optionally branched $C_{1-4}$alkylidene optionally substituted by an oxo group or Y is a group $(CH_2)_jO$ wherein the oxygen atom is nearest the group X and j is 2, 3 or 4;

Z is a 5-membered heteroaromatic ring containing 1, 2 or 3 heteroatoms independently selected from oxygen, nitrogen and sulphur, at most one of the heteroatoms being oxygen or sulphur and providing that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkynyl, $C_{3-6}$cycloalkyl, hydroxy $C_{1-6}$alkyl, $C_{1-6}$alkoxy, $C_{2-6}$alkenyloxy, $C_{2-6}$alkynyloxy, $C_{1-6}$alkoxy$C_{1-6}$alkyl, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$ or $R^7$ and $R^8$, together with the nitrogen atom to which they are attached, form a 4–7 membered heteroaliphatic ring containing the nitrogen atom as the sole heteroatom;

or a pharmaceutically acceptable salt thereof.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-4}$alkyl", "$C_{2-4}$alkenyl", "$C_{2-6}$alkenyl", "hydroxy$C_{1-6}$alkyl", "$C_{2-4}$alkyl" and "$C_{2-6}$alkynyl" are to be construed in an analogous manner.

The expression "$C_{3-6}$cycloalkyl" as used herein includes cyclic propyl, butyl, pentyl and hexyl groups such as cyclopropyl and cyclohexyl.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy, butoxy, pentoxy and hexoxy groups, including cyclopropylmethoxy. Derived expressions such as "$C_{2-6}$akenyloxy", "$C_{2-6}$alkynyloxy", "$C_{1-4}$alkoxy", "$C_{2-4}$alkenyloxy" and "$C_{2-4}$alkyloxy" should be construed in an analogous manner.

$R^1$ may be hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or $CF_3$ groups. $R^1$ is typically hydrogen, fluorine, chlorine, bromine or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or by a pyridyl or phenyl ring each of which rings may be unsubstituted or substituted by one or two halogen atoms or nitro, cyano, amino, methyl or $CF_3$ groups and is generally hydrogen, fluorine or pyridylmethoxy, typically hydrogen.

$R^2$ may be hydrogen, halogen or CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy each of which groups is unsubstituted or substituted with one or two halogen atoms. $R^2$ is typically hydrogen, fluorine, chlorine or bromine, and is generally hydrogen or fluorine, typically hydrogen.

Preferably L is an oxygen atom. L may also be $NR''$ in which $R''$ is preferably hydrogen or methyl. $R''$ may be hydrogen.

X is generally: pyridyl, pyrazinyl, pyridazinyl or pyrimidinyl optionally substituted by a halogen atom or a group $R^3$, $OR^3$, $NR^4R^5$ or a five membered heteroaromatic ring containing 1, 2 or 3 nitrogen atoms, and X is optionally fused to a benzene ring; a 5-membered heteroaromatic ring containing 2 or 3 heteroatoms chosen from oxygen, sulphur and nitrogen, at most one of the heteroatoms being oxygen or sulphur, which is unsubstituted or substituted by one, two or three groups independently chosen from halogen and $R^3$, or which is substituted by a pyridyl, phenyl or benzyl ring which ring is optionally independently substituted by one, two or three halogen atoms or $C_{1-6}$alkyl or $CF_3$ groups; or phenyl optionally substituted by one, two or three independently chosen halogen atoms. In particular X is pyridyl, pyrazinyl, pyridazinyl or pyrimidinyl which is unsubstituted or substituted by methyl, $CF_3$, methoxy, bromine, chlorine, isopropoxy, dimethylamino or a 5-membered heterocyclic ring containing 1, 2 or 3 nitrogen atoms, and X is optionally fused to a benzene ring, or X is pyrazolyl, isothiazolyl, isoxazolyl 1,2,4-triazolyl, thiazolyl, 1,2,3-triazolyl or imidazolyl which is unsubstituted or substituted by one, two or three groups independently chosen from methyl, $CF_3$ and chlorine or is substituted by a phenyl, benzyl or pyridyl ring which ring is unsubstituted or substituted by chlorine or $CF_3$, or X is phenyl which is unsubstituted or substituted by chlorine. X may be monosubstituted by tri($C_{1-6}$alkyl)silyl$C_{1-6}$alkoxy$C_{1-4}$alkyl such as trimethylsilylethoxymethyl. A favoured value of X is pyridazine. Specific values of X are 2-pyridyl, 6-methylpyridin-2-yl, 3-pyridyl, 4-pyridyl, 3,5-dimethylpyrazol-1-yl, 3-methoxypyridin-2-yl, 3-methylisoxazol-5-yl, pyrazol-1-yl, 6-chloropyridin-2-yl, 6-bromopyridin-2-yl, 6-methoxypyridin-2-yl, 6-isopropoxypyridin-2-yl, 6-N,N-dimethylpyridin-2-yl, 6-(imidazol-1-yl)pyridin-2-yl, 3-pyridazino, 4-pyrimidinyl, pyrazin-2-yl, 2-quinolinyl, 2-quinoxalyl, 2-(4-trifluoromethyl)pyridyloxy, 4-methylisothiazolyl, 2,6-dichlorophenyl, 4-methylthiazol-5-yl, 2-methylthiazol-4-yl, 2-[1-(3-trifluoromethyl)pyrid-6-yl]imidazolyl, 1-benzylimidazol-2-yl, 1-(4-chlorophenyl)-1,2,3-triazol-4-yl, 3-chloro-2-methyl-5-trifluoromethylpyrazol-4-yl and 1-methyl-1,2,4-triazol-3-yl. Further specific values of X are (5-trifluoromethyl)pyridyl-2-yl, (3-trifluoromethyl)pyrid-2-yl, (4-trifluoromethyl)pyrid-2-yl, 1-methylimidazol-2-yl, 2-{[2-(trimethylsilyl)ethoxy]methyl}-1,2,4-triazol-3-yl, 3-methylimidazol-4-yl, 1,2,4-triazol-3-yl, 1-isopropyl-11, 2,4 triazol-3-yl, 4-methyl-1,2,4-triazol-3-yl, 1,2,3-triazol-4-yl, isothiazol-3-yl, 1-ethyl-1,2,4-triazol-3-yl 2-methyl-1,2,3-triazol-4-yl, 1-methyl-1,2,3-triazol-4-yl, 2-methyl-1,2,4-triazol-3-yl, 1-methylimidazol-4-yl, 5-tert-butylpyridazin-3-yl and 1-methyl-1,2,3-triazol-5-yl. Still further particular values of X are 2-benzyl-1,2,4-triazol-3-yl, 1-benzyl-1,2,4-triazol-3-yl, 1-nbutyl-1,2,4-triazol-3-yl, 2-ethyl-1,2,4-triazol-3-yl, 2-methylpyrazol-3-yl, 1-methylpyrazol-3-yl, 1-npropyl-1,2,4-triazol-3-yl, 1-(2,2,2-trifluorethyl)-1,2,4-triazol-3-yl, 1-ethyl-1,2,3-triazol-5-yl, 1-methyltetrazol-2-yl, imidazol-2-yl, 2-npropyl-1,2,4-triazol-3-yl, 1-ethyl-1,2,3-triazol-4yl, 2-ethyl-1,2,3-triazol-4-yl, 1-ethylimidazol-5-yl, 1-ethylimidazol-4yl, 1-npropyl-1,2,4-triazol-3-yl and 1-ethyl-1,2,3-triazol-5-yl.

When X is a substituted 6-membered heteroaromatic ring: $R^x$ is preferably halogen, $R^3$, $OR^3$, $NR^4R^5$ or a five-membered heteroaromatic ring containing 1, 2 or 3 nitrogen atoms and more preferably methyl, $CF_3$, methoxy, bromine, chlorine, isopropoxy, dimethylamino or a five-membered heterocyclic ring containing 1, 2 or 3 nitrogen atoms; and $R^y$ and $R^z$ are preferably absent When X is a substituted 5-membered heteroaromatic ring:
$R^x$ is preferably halogen, $R^3$ or a pyridyl, phenyl or benzyl ring which ring is optionally independently substituted by one, two or three halogen atoms or $C_{1-6}$alkyl or $CF_3$ groups and more preferably $R^x$ is methyl, $CF_3$, chlorine or a phenyl, pyridyl or benzyl ring which ring is unsubstituted or substituted by chlorine or $CF_3$; and $R^y$ and $R^z$ are preferably halogen or $R^3$, and more preferably methyl, $CF_3$ or chlorine.

Particularly aptly X is an unsubstituted six-membered heteroaromatic group containing one or two nitrogen atoms.

Apt values for Y include $CH_2$, $CH(CH_3)$, $CH_2CH_2$ and $CH_2CH_2CH_2$ optionally substituted by an oxo group, and $CH_2CH_2O$ and $CH_2CH_2CH_2O$. For example, Y can be $CH_2$, $CH_2CH_2$, $CH_2CH_2CH_2$, $CH_2CH_2O$ or $CH_2CH_2CH_2O$. Preferably Y is $CH_2$ or $CH_2CH_2$ and most preferably $CH_2$.

From the foregoing it will be understood that particularly suitable groups L-Y-X are $OCH_2X$ groups where X is pyridyl or pyridazinyl, particularly 2-pyridyl.

$R^v$ is suitably chlorine, $R^6$, thienyl, furyl, pyridyl or $NR^7R^8$, more particularly $R^6$, thienyl, furyl, pyridyl or $NR^7R^8$, for example $C_{1-6}$alkyl, $C_{3-6}$cycloalkyl, hydroxy$C_{1-6}$alkyl, pyridyl, thienyl or amino and more particularly methyl, ethyl, ethoxy, isopropyl, cyclopropyl, thienyl or pyridyl, and even more particularly methyl, ethyl, isopropyl, cyclopropyl, thienyl or pyridyl. A further example of $R^v$ is chlorine.

$R^w$ is suitably $R^6$, for example $C_{1-6}$alkyl, $CH_2F$ or hydroxy$C_{1-6}$alkyl, more particularly methyl, $CH_2F$ or hydroxymethyl. Generally $R^w$ is absent.

$R^x$ may be halogen, $R^3$, $OR^3$, $OCOR^3$, $NR^4R^5$, $NR^4COR^5$, CN or $R^9$.

Z is preferably a 5-membered heteroaromatic ring containing 1, 2 or 3 heteroatoms independently selected from oxygen, nitrogen and sulphur, at most one of the heteroatoms being oxygen or sulphur and providing that when two of the heteroatoms are nitrogen an oxygen or sulphur atom is also present and that when one of the atoms is oxygen or sulphur then at least one nitrogen atom is present, or a 6-membered heteroaromatic ring containing 2 or 3 nitrogen atoms, Z being optionally substituted by $R^v$ and/or $R^w$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heteroatoms independently selected from oxygen, nitrogen and sulphur, at most one of the other heteroatoms being oxygen or sulphur and $R^w$ is $R^6$ or CN.

Suitable values for Z include pyrimidinyl, pyrazinyl, pyrrolyl, oxazolyl, isoxazolyl, thiazolyl, isothiazolyl, oxadiazolyl and thiadiazolyl groups which groups are optionally substituted by $R^6$, thienyl, furyl, pyridyl or $NR^7R^8$ groups.

Z is very aptly a 5-membered heteroaromatic ring containing one oxygen and one or two nitrogen ring atoms and is optionally substituted by a group $R^6$. In such compounds $R^6$ is favourably a methyl group.

Favoured values for Z include optionally substituted isoxazoles and oxadiazoles.

Z may be unsubstituted.

Z may very aptly be substituted by methyl.

Particular values of Z are 3-methyloxadiazol-5-yl, 3-cyclopropyloxadiazol-5-yl, 5-methylisoxazol-3-yl, 5-(3-pyridyl)-isoxazol-3-yl, 5-hydroxymethylisoxazol-3-yl, 4,5-dimethylisoxazol-3-yl, 5-ethylisoxazol-3-yl, 5-cyclopropylisoxazol-3-yl, 5-isopropylisoxazol-3-yl, isoxazol-3-yl and 5-thienylisoxazol-3-yl. Further particular values for Z include 5-fluoromethylisoxazol-3-yl, 4-methylisoxazol-3-yl, 5-ethoxyisoxazol-3-yl, 4-methyl-5-chloroisoxazol-3-yl, 5-trifluoromethylisoxazol-3-yl, 5-(pyrid-2-yl)isoxazol-3-yl, 5-benzylisoxazol-3-yl, 5-chloroisoxazol-3-yl and 3-cyclopropyloxadiazol-5-yl. Still further particular values for Z include 5-methoxyisoxazol-3-yl, 5-methoxymethylisoxazol-3-yl, 5-methyloxadiazol-3-yl, pyrazin-2-yl and 3-methylisoxazol-5-yl.

$R^3$ may be $C_{1-6}$alkyl, $C_{2-6}$alkenyl $C_{2-6}$alkynyl, $C_{3-6}$cycloalkyl, hydroxy$C_{1-6}$alkyl or $CF_3$.

Generally $R^3$ is $C_{1-6}$alkyl, $C_{1-6}$alkoxy or $CF_3$. In particular $R^3$ is methyl, methoxy, isopropoxy or trifluoromethyl.

Generally $R^4$ and $R^5$ are independently hydrogen or $C_{1-6}$alkyl, in particular hydrogen or methyl, for example both can be methyl.

$R^6$ may be $C_{1-6}$alkyl, $C_{2-6}$alkenyl, $C_{2-6}$alkynyl, $C_{3-6}$cycloalkyl, hydroxy$C_{1-6}$alkyl, $C_{1-6}$alkoxy, $C_{2-6}$alkenyloxy, $C_{2-6}$alkynyloxy, $CH_2F$ or $CF_3$. Generally $R^6$ is $CH_2F$, $CF_3$, $C_{1-6}$alkoxy, $C_{3-6}$cycloalkoxy, $C_{1-6}$alkyl or hydroxy$C_{1-6}$alkyl, for example, $CH_2F$, $CF_3$, methyl, ethyl, isopropyl, cyclopropyl or hydroxymethyl, particularly methyl or cyclopropyl. Alternatively $R^6$ is $C_{1-6}$alkyl or hydroxy$C_{1-6}$alkyl, for example, methyl, ethyl, isopropyl, cyclopropyl or hydroxymethyl.

Generally $R^7$ and $R^8$ are independently hydrogen or $C_{1-6}$alkyl, particularly hydrogen or methyl.

Generally $R^9$ is pyrazolyl, imidazolyl, phenyl, benzyl or pyridyl optionally substituted by halogen, preferably chlorine, or $CF_3$. In particular $R^9$ can be imidazol-1-yl, 3-trifluoromethylpyrid-5-yl, benzyl and 4-chlorophenyl.

Generally $R^{10}$ is $C_{1-6}$alkyl or $CF_3$, in particular methyl or $CF_3$, for example $CF_3$.

A preferred subclass of compounds is that represented by formula I':

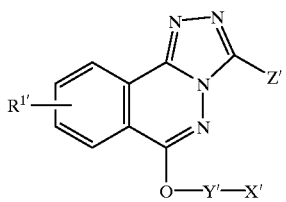

(I')

wherein:
$R^{1'}$ is hydrogen or fluorine;
X' is pyridyl, pyrazinyl, pyridazinyl or pyrimidinyl which is unsubstituted or substituted by methyl, $CF_3$, methoxy, bromine, chlorine, isopropoxy, dimethylamino or a 5-membered heterocyclic ring containing 1, 2 or 3 nitrogen atoms, and X' is optionally fused to a benzene ring, or X' is pyrazolyl, isothiazolyl, isoxazolyl, 1,2,4-triazolyl, thiazolyl, 1,2,3-triazolyl or imidazolyl any of which is unsubstituted or substituted by one, two or three groups independently chosen from methyl, $CF_3$ and chlorine or is substituted by a phenyl, benzyl or pyridyl ring which ring is unsubstituted or substituted by chlorine or $CF_3$, or X' is phenyl which is unsubstituted or substituted by chlorine;
Y' is $CH_2$ or $CH_2CH_2$; and
Z' is an isoxazole or oxadiazole optionally substituted by $CH_2F$, $C_{1-6}$alkyl, $C_{3-6}$cycloalkyl, hydroxy$C_{1-6}$alkyl, pyridyl, thienyl or amino; or a pharmaceutically acceptable salt thereof.

$R^{1'}$ is preferably hydrogen.

X' is preferably pyridazyl or pyridyl optionally substituted by methyl, and especially 2-pyridyl.

Y' is preferably $CH_2$.

Z' is preferably unsubstituted or substituted by methyl, $CH_2OH$ or $CH_2F$, in particular by methyl. Z is particularly 5-methylisoxazol-3-yl.

In a further preferred subclass of compounds of formula I or I', X or X' as the case may be is 1,2,4-triazolyl which is unsubstituted or substituted by one, two or three groups independently chosen from methyl, $CF_3$ and chlorine. Preferably L or L' as the case may be is O. Preferably Y or Y' as the case may be is $CH_2$. Preferably $R^1$ and $R^2$ or $R^{1'}$ and $R^{2'}$ as the case may be are both hydrogen. Preferably Z or Z' as the case may be is 5-methylisoxazol-3-yl or 3-methylisoxazol-5-yl, and particularly 5-methylisoxazol-3-yl. More particularly the 1,2,4-triazolyl is an unsubstituted or substituted 1,2,4-triazol-3-yl. Preferably the 1,2,4-triazolyl is substituted by methyl. A particularly favoured value of X or X' is 1-methyl-1,2,4triazol-3-yl.

In another preferred subclass of compounds of formula I or I', X or X' as the case may be is imidazolyl which is unsubstituted or substituted by one, two or three groups independently chosen from methyl, $CF_3$ and chlorine. Preferably L or L' as the case may be is O. Preferably Y or Y' as the case may be is $CH_2$. Preferably $R^1$ and $R^2$ or $R^{1'}$ and $R^{2'}$ as the case may be are both hydrogen. Preferably Z or Z' as the case may be is 5-methylisoxazol-3-yl. More particularly the imidazolyl is an unsubstituted or substituted imidazolyl-4-yl. Preferably the imidazolyl is substituted by methyl, for example it is 1-methylimidazol-4-yl.

In a further preferred subclass of compounds of formula I or I', X or X' as the case may be is 1,2,3-triazolyl which is unsubstituted or substituted by one, two or three groups independently chosen from methyl, $CF_3$ and chlorine. Preferably L or L' as the case may be is O. Preferably Y or Y' as the case may be is $CH_2$. Preferably $R^1$ and $R^2$ or $R^{1'}$ and $R^{2'}$ as the case may be are both hydrogen. Preferably Z or Z' as the case may be is 5-methylisoxazol-3-yl. More particularly the 1,2,3-triazolyl is an unsubstituted or substituted 1,2,3-triazol-4-yl. Preferably the 1,2,3-triazolyl is substituted by methyl. A particularly favoured value of X or X' is 1-methyl-1,2,3-triazol-4-yl.

For use in medicine, the salts of the compounds of formula I will be pharmaceutically acceptable salts. Hence in a favoured aspect this invention provides the compounds of the formula I and pharmaceutically acceptable salts thereof. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the present invention.

It will be understood by the skilled person that when a five-membered heterocyclic ring is referred to in the foregoing having four heteroatoms in the ring, then all these heteroatoms are nitrogen. It will further be understood that when a substituted five-membered heterocyclic ring is referred to having two nitrogen atoms and an oxygen or sulphur atom in the ring, then only one substituent may be present so that aromaticity is maintained. Thus, for example, in such a case X may only be substituted by $R^x$ and Z may only be substituted by $R^y$.

Specific compounds within the scope of the present invention include:

3-(5-Methylisoxazol-3-yl)-6-(2-pyridyl)methyloxy-1,2,4-triazolo[3,4-a]phthalazine, 3-(5-Methylisoxazol-3-yl)-6-(6-methylpyridin-2-yl)methyloxy-1,2,4-triazolo[3,4-a]phthalazine, 3-(5-Methylisoxazol-3-yl)-6-(3-pyridyl)methyloxy-1,2,4-triazolo[3,4-a]phthalazine, 3-(5-Methylisoxazol-3-yl)-6-(4pyridyl)methyloxy-1,2,4-triazolo[3,4-a]phthalazine, 6-(3,5-Dimethylpyrazol-1-yl)methyloxy-3-(5-methylisoxazol-3-yl)-1,2,4-triazolo[3,4-a]phthalazine, 6-(3-Methoxypyridin-2-yl)methyloxy-3-(5-methylisoxazol-3-yl)-1,2,4-triazolo[3,4-a]phthalazine, 6-(5-Methyhsoxazol-3-yl)methyloxy-3-(5-methylisoxazol-3-yl)-1,2,4-triazolo[3,4-a]phthalazine, 3-(5-Methylisoxazol-3-yl)-6-(pyrazol-1-yl)methyloxy-1,2,4-triazolo[3,4-a]phthalazine, 6-(6-Chloropyridin-2-yl)methyloxy-3-(5-methyhsoxazol-3-yl)-1,2,4-triazolo[3,4-a]phthalazine, 6-(6-Bromopyridin-2-yl)methyloxy-3-(5-methylisoxazol-3-yl)-1,2,4-triazolo[3,4-a]phthalazine, 6-(6-Methoxypyridin-2-yl)methyloxy-3-(5-methylisoxazol-3-yl)-1,2,4-triazolo[3,4-a]phthalazine, 6-(6-Isopropoxypyridin-2-yl)methyloxy-3-(5-methylisoxazol-3-yl)-1,2,4-triazolo[3,4-a]phthalazine, 6-(6-N,N-Dimethylpyrdin-2-yl)methyloxy-3-(5-methylisoxazol-3-yl)-1,2,4-triazolo[3,4-a]phthalazine, 6-[6-(Imidazol-1-yl)pyridin-2-yl]methyloxy-3-(5-methylisoxazol-3-yl)-1,2,4-triazolo[3,4-a]phthalazine, 3-(5-Methylisoxazol-3-yl)-6-(3-pyridazino)methyloxy-1,2,4-triazolo[3,4-a]phthalazine, 3-(5-Methylisoxazol-3-yl)-6-(4-pyrimidinyl)methyloxy-1,2,4-triazolo[3,4-a]phthalazine, 3-(5-Methylisoxazol-3-yl)-6-pyrazin-2-yl)methyloxy-1,2,4-triazolo[3,4-a]phthalazine, 3-(5-Methylisoxazol-3-yl)-6-(2-quinohinyl)methyloxy-1,2,4-triazolo[3,4-a]phthalazine, 3-(5-Methylisoxazol-3-yl)-6-(2-quinolilyl)methyloxy-1,2,4-triazolo[3,4-a]phthalazine, 3-(5-Methylisoxazol-3-yl)-6-(2-(4-trifluoromethyl)pyridyloxy)ethyloxy-1,2,4-triazolo[3,4-a]phthalazine, 3-(5-Methylisoxazol-3-yl)-6-(6-methylpyrid-2-yl)propyloxy-1,2,4-triazolo[3,4-a]phthalazine, 3-(5-Methylisoxazol-3-yl)-6-(5-(4-methylisothiazolyl)ethyloxy-1,2,4-triazolo[3,4-a]phthalazine, 3-(5-Methylisoxazol-3-yl)-6-(2,6-dichloropbenyl)methyloxy-1,2,4-triazolo-phthalazine, 3-(5-Methylisoxazol-3-yl)-6-(4-methylthiazol-5-yl)ethyloxy-1,2,4-triazolo-[3,4-a]phthalazine, 3-(5-Methylisoxazol-3-yl)-6-(2-methylthiazol-4-yl)ethyloxy-1,2,4-triazolo-[3,4-a]phthalazine, 3-(5-Methylisoxazol-3-yl)-6-(2-[1-(3-trifluoromethyl)pyrid-6-yl]imidazolyl)methyloxy-1,2,4-triazolo[3,4-a]phthalazine 3-(5-Methylisoxazol-3-yl)-6-[(1-benzyl)imidazol-2-yl]methyloxy-1,2,4-triazolo[3,4-a]phthalazine, 3-(5-Methylisoxazol-3-yl)-6-[1-(4-chlorophenyl)-1,2,3-triazol-4-yl]methyloxy-1,2,4-triazolo[3,4-a]phthalazine, 3-(5-Methylisoxazol-3-yl)-6-(3-chloro-2-methyl-5-trifluoromethylpyrazol-4-yl)methyloxy-1,2,4-triazolo[3,4-a]phthalazine, 3-(5-Isopropylisoxazol-3-yl)-6-(2-pyridyl)methyloxy-1,2,4-triazolo[3,4-a]phthalazine, 3-(5-Cyclopropylisoxazol-3-yl)-6-(2-pyridyl)methyloxy-1,2,4-triazolo[3,4-a]phthalazine, 3-(5-Ethylisoxazol-3-yl)-6-(2-pyridyl)methyloxy-1,2,4-triazolo[3,4-a]phthalazine, 3-(4,5-Dimethylisoxazol-3-yl)-6-(2-pyridyl)methyloxy-1,2,4triazolo[3,4-a]phthalazine, 3(3-Isoxazolyl)-6-(2-pyridyl)methyloxy-1,2,4-triazolo[3,4-a]phthalazine, 3-[5-(Pyridin-3-yl)isoxazol-3-yl]-6-(2-pyridinyl)methyloxy-1,2,4-triazolo[3,4-a]phthalazine, 6-(2-Pyridyl)methyloxy-3-[5-(2-thienyl)isoxazol-3-yl]-1,2,4triazolo[3,4-a]phthalazine, 3-(5-Methylisoxazol-3-yl)-6-(1-methyl-1,2,4-triazol-3-yl)methyloxy-1,2,4-triazolo[3,4a]phthalazine, 7,10-Difluoro-3-(5-methylisoxazol-3-yl)-6-(2-pyridyl)methyloxy-1,2,4-triazolo[3,4-a]phthalazine, 6,10-Bis[(2-pyridyl)methyloxy]-3-(5-methylisoxazol-3-yl)-1,2,4-triazolo[3,4-a]phthalazine, 7-Fluoro-3-(5-methylisoxazol-3-yl)-6-(2-pyridyl)methyloxy-1,2,4-triazolo[3,4-a]phthalazine, 10-Fluoro-3-(5-methylisoxazol-3-yl)-6-(2-pyridyl)methyloxy-1,2,4-triazolo[3,4-a]phthalazine;

and the pharmaceutically acceptable salts thereof

Further specific compounds within the scope of the present invention include:

6-(1-methylimidazol-4-yl)methyloxy-3-(5-methylisoxazol-3-yl)-1,2,4-triazolo[3,4-a]phthalazine;

6-(1-methylimidazol-5-yl)methyloxy-3-(5-methylisoxazol-3-yl)-1,2,4-triazolo[3,4-a]phthalazine;

3-(5-methylisoxazol-3-yl)-6-(2-methyl-1,2,4-triazol-3-yl)methyloxy-1,2,4-triazolo[3,4-a]phthalazine;

3-(5-methylisoxazol-3-yl)-6-(4-methyl-1,2,4-triazol-3-yl)methyloxy-1,2,4-triazolo[3,4-a]phthalazine;

3-(5-methylisoxazol-3-yl)-6-[2-{[2-(trimethylsilyl)ethoxy]methyl}-1,2,4-triazolyl]methyloxy-1,2,4-triazolo[3,4-a]phthalazine;

3-(5-methylisoxazol-3-yl)-6-(1,2,4-triazol-3-yl)methyloxy-1,2,4-triazolo[3,4-a]phthalazine;

3-(5-methylisoxazol-3-yl)-6-(1-isopropyl-1,2,4-triazol-3-yl)methyloxy-1,2,4-triazolo[3,4-a]phthalazine;

3-(5-methylisoxazol-3-yl)-6-(-1-ethyl-1,2,4-triazol-3-yl)methyloxy-1,2,4-triazolo[3,4-a]phthalazine;

3-(5-methylisoxazol-3-yl)-6-(1H-1,2,3-triazol-5-yl)methyloxy-1,2,4-triazolo[3,4-a]phthalazine;

3-(5-methylisoxazol-3-yl)-6-(1-methyl-1,2,3-triazol-5-yl)methyloxy-1,2,4-triazolo[3,4-a]phthalazine;

3-(5-methylisoxazol-3-yl)-6-(2-methyl-1,2,3-triazol-4-yl)methyloxy-1,2,4-triazolo[3,4-a]phthalazine;

3-(5-methylisoxazol-3-yl)-6-(1-methyl-1,2,3-triazol-4-yl)methyloxy-1,2,4-triazolo[3,4-a]phthalazine;

3-(5-methylisoxazol-3-yl)-6-[(5-trifluoromethyl)pyridin-2-yl]methyloxy-1,2,4-triazolo[3,4-a]phthalazine;

3-(5-methylisoxazol-3-yl)-6-[(3-trifluoromethyl)pyridin-2-yl]methyloxy-1,2,4-triazolo[3,4-a]phthalazine;

3-(5-methylisoxazol-3-yl)-6-[(4-trifluoromethyl)pyridin-2-yl]methyloxy-1,2,4-triazolo[3,4-a]phthalazine;

3-(5-methylisoxazol-3-yl)-6-(thiazol-4yl)-1,2,4-triazolo[3,4-a]phthalazine;

3-(isothiazol-3-yl)methyloxy-3-(5-methylisoxazol-3-yl)-1,2,4-triazolo[3,4-a]phthalazine;

3-(4-methylisoxazol-3-yl)-6-[(4tert-butyl)pyridazin-3-yl]methyloxy-1,2,4-triazolo[3,4-a]phthalazine;

3-(5-methylisoxazol-3-yl)-6-[(5-tert-butyl)pyridazin-3-yl]methyloxy-1,2,4-triazolo[3,4-a]phthalazine;

6-(imidazol-4-yl)methyloxy-3-(5-methylisoxazol-3-yl)-1,2,4-triazolo[3,4-a]phthalazine;

3-[(5-methylisoxazol-3-yl)-6-(1-methyl-1,2,4-triazol-3-yl)methylamino-1,2,4-triazolo[3,4-a]phthalazine;

3-(5-methylisoxazol-3-yl)-6-{(N-methyl),N-[(1-methyl-1,2,4-triazol-3-yl)methy]amino}-1,2,4-triazolo[3,4-a]phthalazine;

3-(5-isoxazol-3-yl)-6-(1-methyl-1,2,4-triazol-3-yl)methyloxy-1,2,4-triazolo[3,4-a]phthalazine;

3-(3-isoxazolyl)-6-(2-methyl-1,2,4-triazol-3-yl)methyloxy-1,2,4-triazolo[3,4-a]phthalazine;

3-(3-isoxazolyl)-6-(1-methylimidazol-4-yl)methyloxy-1,2,4-triazolo[3,4-a]phthalazine;

3-(5-hydroxymethylisoxazol-3-yl)-6-(2-pyridyl)methyloxy-1,2,4-triazolo-[3,4-a]phthalazine;

3-(5-hydroxymethylisoxazol-3-yl)-6-(1-methyl-1,2,4-triazol-3-yl)methyloxy-1,2,4-triazolo[3,4-a]phthalazine;

3-(5-fluoromethylisoxazol-3-yl)-6-(2-pyridyl)methyloxy-1,2,4-triazolo[3,4-a]phthalazine;

3-(5-fluoromethylisoxazol-3-yl)-6-(1-methyl-1,2,4-triazol-3-yl)methyloxy-1,2,4-triazolo[3,4-a]phthalazine;

3-(5-fluoromethylisoxazol-3-yl)-6-(1-methyl-1,2,4-triazol-5-yl)methyloxy-1,2,4-triazolo[3,4-a]phthalazine;

3-(5-fluoromethylisoxazol-3-yl)-6-(1,2,4-triazol-3-yl)methyloxy-1,2,4-triazolo[3,4-a]phthalazine;

3-(5-ethoxyisoxazol-3-yl)-6-(2-pyridyl)methyloxy-1,2,4-triazolo[3,4-a]phthalazine;

3-(5-ethoxyisoxazol-3-yl)-6-(1-methyl-1,2,4-triazol-3-yl)methyloxy-1,2,4-triazolo[3,4-a]phthalazine;

3-(5-ethoxyisoxazol-3-yl)-6-(2-methyl-1,24-triazol-3-yl)methyloxy-1,2,4-triazolo[3,4-a]phthalazine;

3-(5-ethoxyisoxazol-3-yl)-6-(1,2,4-triazol-3-yl)methyloxy-1,2,4-triazolo[3,4-a]phthalazine;

3-(5-ethoxyisoxazol-3-yl)-6-(1-methylimidazol-4-yl)methyloxy-1,2,4-triazolo[3,4-a]phthalazine;

3-(5-chloroisoxazol-3-yl)-6-(2-pyridyl)methyloxy-1,2,4-triazolo[3,4-a]phthalazine;

3-(5-chloroisoxazol-3-yl)-6-(1-methyl-1,2,4-triazol-3-yl)methyloxy-1,2,4-triazolo[4,3-a]phthalazine;

3-(5-chloroisoxazol-3-yl)-6-(2-methyl-1,2,4-triazol-3-yl)methyloxy-1,2,4-triazolo[4,3-a]phthalazine;

3-(5-chloroisoxazol-3-yl)-6-(1-methylimidazol-4-yl)methyloxy-1,2,4-triazolo[3,4-a]phthalazine;

3-(5-chloroisoxazol-3-yl)-6-(1,2,4-triazol-3-yl)methyloxy-1,2,4-triazolo[3,4-a]phthalazine;

3-(5-chloroisoxazol-3-yl)-6-(1-methylimidazol-5-yl)methyloxy-1,2,4-triazolo[3,4-a]phthalazine;

3-(5-chloroisoxazol-3-yl)-6-(4-methyl-1,2,4-triazol-3-yl)methyloxy-1,2,4-triazolo[3,4-a]phthalazine;

6-(2-pyridylmethyloxy)-3-(5-trifluoromethylisoxazol-3-yl)-1,2,4-triazolo[3,4-a]phthalazine;

3-(5-phenylmethylisoxazol-3-yl)-6-[(2-pyridyl)methyloxy]-1,2,4-triazolo[3,4-a]phthalazine;

3-[5-(2-pyridyl)isoxazol-3-yl]-6-(2-pyridyl)methyloxy-1,2,4-triazolo[3,4-a]phthalazine;

3-(4-methylisoxazol-3-yl)-6-(2-pyridyl)methyloxy-1,2,4-triazolo[3,4-a]phthalazine;

3-(5-chloro-4-methylisoxazol-3-yl)-6-(2-pyridyl)methyloxy-1,2,4-triazolo[3,4-a]phthalazine;

3-(3-methyloxadiazol-5-yl)-6-(2-pyridyl)methyloxy-1,2,4-triazolo[3,4-a]phthalazine;

3-(3-cyclopropyloxadiazol-5-yl)-6-(2-pyridyl)methyloxy-1,2,4-triazolo[3,4-a]phthalazine;

and the pharmaceutically acceptable salts thereof.

Still further specific compounds within the scope of the present invention are:

3-(3-Methyl-1,2,4-oxadiazol-5-yl)-6-(1-methyl-1,2,4-triazol-3-yl)methyloxy-1,2,4-triazolo[3,4-a]phthalazine;

6-(1-Benzyl-1,2,4-triazol-3-yl)-3-(5-methylisoxazol-3-yl)methyloxy-1,2,4-triazolo[3,4-a]phthalazine and 6-(2-Benzyl-1,2,4-triazol-3-yl)-3-(5-methylisoxazol-3-yl)methyloxy-1,2,4-triazolo[3,4-a]phthalazine;

6-(1-Butyl-1,2,4-triazol-3-yl)-3-(5-methylisoxazol-3-yl)methyloxy-1,2,4-triazolo[3,4-a]phthalazine;

6-(2-Ethyl-1,2,4-triazol-3-yl)-3-(5-methylisoxazol-3-yl)methyloxy-1,2,4-triazolo[3,4-a]phthalazine;

3-(5-Methylisoxazol-3-yl)-6-(1-propyl-1,2,4-triazol-3-yl)methyloxy-1,2,4-triazolo[3,4-a]phthalazine;

3-(5-Methylisoxazol-3-yl)-6-[1-(2,2,2-trifluoroethyl)-1,2,4-triazol-3-yl]methyloxy-1,2,4-triazolo[3,4-a]phthalazine;

6-(1-Ethylimidazol-5-yl)methyloxy-3-(5-methylisoxazol-3-yl)-1,2,4-triazolo[3,4-a]phthalazine;

6-(1-Ethylimidazol-4-yl)methyloxy-3-(5-methylisoxazol-3-yl)-1,2,4-triazolo[3,4-a]phthalazine;

6-(1-Ethyl-1,2,3-triazol-5-yl)methyloxy-3-(5-methylisoxazol-3-yl)-1,2,4-triazolo[3,4-a]phthalazine;

6-(1-Ethyl-1,2,3-triazol-4-yl)methyloxy-3-(5-methylisoxazol-3-yl)-1,2,4-triazolo[3,4-a]phthalazine;

6-(2-Ethyl-1,2,3-triazol-4-yl)methyloxy-3-(5-methylisoxazol-3-yl)-1,2,4-triazolo[3,4-a]phthalazine;

3-(5-Methylisoxazol-3-yl)-6-(1-methyltetrazol-5-yl)methyloxy-1,2,4-triazolo[3,4-a]phthalazine;

6-(Imidazol-2-yl)methyloxy-3-(5-methylisoxazol-3-yl)-1,2,4-triazolo[3,4-a]phthalazine;

3-(5-Methylisoxazol-3-yl)-6-(2-methylpyrazol-3-yl)methyloxy-1,2,4-triazolo[3,4-a]phthalazine;

3-(5-Methylisoxazol-3-yl)-6-(1-methylpyrazol-3-yl)methyloxy-1,2,4-triazolo[3,4-a]phthalazine;

3-(5-Methylisoxazol-3-yl)-6-(1-methylpyrazol-4-yl)methyloxy-1,2,4-triazolo[3,4-a]phthalazine;

3-(5-Ethylisoxazol-3-yl)-6-(2-methyl-1,2,4-triazol-3-yl)methyloxy-1,2,4-triazolo[3,4-a]phthalazine;

3-(5-Ethylisoxazol-3-yl)-6-(1-methyl-1,2,4-triazol-3-yl)methyloxy-1,2,4-triazolo[3,4-a]phthalazine;

3-(5-Ethylisoxazol-3-yl)-6-(pyrazin-2-yl)methyloxy-1,2,4-triazolo[3,4-a]phthalazine;

6-(1-Ethyl-1,2,3-triazol-4-yl)methyloxy-3-(3-isoxazolyl)-1,2,4-triazolo[3,4-a]phthalazine;

6-(1-Ethyl-1,2,4-triazol-3-yl)methyloxy-3-(3-isoxazolyl)-1,2,4-triazolo[3,4-a]phthalazine;

6-(1-Ethyl-1,2,3-triazol-5-yl)methyloxy-3-(3-isoxazolyl)-1,2,4-triazolo[3,4-a]phthalazine;

6-(1-Ethylimidazol-4-yl)-4-(3-isoxazolyl)methyloxy-1,2,4-triazolo[3,4-a]phthalazine;

6-(2-Ethyl-1,2,4-triazol-3-yl)-3-(3-isoxazolyl)methyloxy-1,2,4-triazolo[3,4-a]phthalazine;

3-(3-Isoxazolyl)-6-(2-propyl-1,2,4-triazol-3-yl)methyloxy-1,2,4-triazolo[3,4-a]phthalazine;

3-(3-Isoxazolyl)-6-(1-propyl-1,2,4-triazol-3-yl)methyloxy-1,2,4-triazolo[3,4-a]phthalazine;

6-(1-Benzylimidazol-2-yl)methyloxy-3-(3-isoxazolyl)-1,2,4-triazolo[3,4-a]phthalazine;

3-(5-Methoxymethylisoxazol-3-yl)-6-(1-methyl-1,2,4-triazol-3-yl)methyloxy-1,2,4-triazolo[3,4-a]phthalazine;

3-(5-Methoxymethylisoxazol-3-yl)-6-(2-methyl-1,2,4-triazol-3-yl)methyloxy-1,2,4-triazolo[3,4-a]phthalazine;

3-(5-Methoxyisoxazol-3-yl)-6-(1-methylimidazol-4-yl)methyloxy-1,2,4-triazolo[3,4-a]phthalazine;

3-(5-Methoxyisoxazol-3-yl)-6-(1-methy-1,2,4-triazol-3-yl)methyloxy-1,2,4-triazolo[3,4-a]phthalazine;

3-(3-Methylisoxazol-5-yl)-6-(2-pyridyl)methyloxy-1,2,4-triazolo[3,4-a]phthalazine;

3-(3-Methylisoxazol-5-yl)-6-(6-methylpyridin-2-yl)methyloxy-1,2,4-triazolo[3,4-a]phthalazine;

3-(3-Methylisoxazol-5-yl)-(pyrazin-2-yl)methyloxy-1,2,4triazolo[3,4-a]phthalazine;

3-(3-Methylisoxazol-5-yl)-6-(2-methyl-1,2,4-triazol-3-yl)methyloxy-1,2,4-triazolo[3,4-a]phthalazine;

3-(3-Methylisoxazol-5-yl)-6-(1-methyl-1,2,4-triazol-3-yl)methyloxy-1,2,4-triazolo[3,4-a]phthalazine;

3-(3-Ethoxyisoxazol-5-yl)-6-(1-methyl-1,2,4-triazol-3-yl)methyloxy-1,2,4-triazolo[3,4-a]phthalazine;

6-(2-Methyl-1,2,4-triazol-3-yl)methyloxy-3-(pyrazin-2-yl)-1,2,4-triazolo[3,4-a]phthalazine;

3-(Pyrazin-2-yl)-6-(pyrid-2-yl)methyloxy-1,2,4-triazolo[3,4-a]phthalazine;

3-(5-Methyl-1,2,4-oxadiazol-3-yl)-6-(1-methyl-1,2,4-triazol-3-yl)methyloxy-1,2,4-triazolo[3,4-a]phthalazine;

and the pharmaceutically acceptable salts thereof.

Particularly favoured compounds are:

3-(5-methylisoxazol-3-yl)-6-(2-pyridyl)methyloxy-1,2,4-triazolo[3,4-a]phthalazine and 3-(5-methylisoxazol-3-yl)-6-(3-pyridazinyl)methyloxy-1,2,4-triazolol[3,4-a]phthalazine or pharmaceutically acceptable salts thereof.

An especially favoured compound is 3-(5-methylisoxazol-3-yl)-6-(2-pyridyl)methyloxy-1,2,4-triazolo[3,4-a]phthalazine or a pharmaceutically acceptable salt thereof.

Another especially favoured compound is 3-(5-methylisoxazol-3-yl)-6-(1-methyl-1,2,4-triazol-3-yl)methyloxy-1,2,4-triazolo[3,4-a]phthalazine or a pharmaceutically acceptable salt thereof.

Another especially favoured compound is 3-(5-methylisoxazol-3-yl)-6-(1-methylimidazol-4-yl)methyloxy-1,2,4-triazolo[3,4-a]phthalazine or a pharmaceutically acceptable salt thereof.

Another especially favoured compound is 3-(5-methylisoxazol-3-yl)-6-(1-methyl-1,2,3-triazol-4-yl)methyloxy-1,2,4-triazolo[3,4-a]phthalazine or a pharmaceutically acceptable salt thereof.

Another especially favoured compound is 3-(3-methylisoxazol-5-yl)-6-(1-methyl-1,2,4-triazol-3-yl)methyloxy-1,2,4-triazolo[3,4-a]phthalazine or a pharmaceutically acceptable salt thereof.

Examples of pharmaceutically acceptable salts are hydrochlorides, sulfates, citrates, tartrates, acetates, methanesulfonates, phosphates, oxalates and benzoates.

The compounds of the present invention have a good binding affinity ($K_i$) for the α5 subunit. In a preferred embodiment the compounds of the invention are binding selective for the α5 subunit relative to the α1, α2 and α3 subunits. In another preferred embodiment the compounds are functionally selective for the α5 subunit as partial or full inverse agonists whilst substantially being antagonists at the α1, α2 and α3 subunits.

Cognition enhancement can be shown by testing the compounds in the Morris watermaze as reported by McNamara and Skelton, Psychobiology, 21:101–108. The functional efficacy at the various receptor subtypes can be calculated using the method disclosed in WO-A-9625948.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycel, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention for use in a method of treatment of the human body. Preferably the treatment is for a condition associated with GABA$_A$ receptors comprising the α5 subunit and/or for the enhancement of cognition. Preferably the condition is a neurological deficit with an associated cognitive disorder such as a dementing illness such as Alzheimer's disease. Other conditions to be treated include cognition deficits due to traumatic injury, stroke, Parkinson's disease, Downs syndrome, age related memory deficits, attention deficit disorder and the like.

Thus, for example, the compounds of the present invention can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS.

Those compounds which are not inverse agonists at the α5 subtype may be used as alcohol antagonists or to treat obesity.

The present invention further provides the use of a compound of the present invention in the manufacture of a medicament for the enhancement of cognition, preferably in a human suffering from a dementing illness such as Alzheimer's disease.

Also disclosed is a method of treatment of a subject suffering from a cognition deficit, such as that resulting from a dementing illness such as Alzheimer's disease, which comprises administering to that subject an effective amount of a compound according to the present invention.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For the enhancement of cognition, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

It is preferred that the compounds of the present invention are ground, for example using a pestle and mortar or industrial equivalent thereto, to a particle size of between 1 and 10 gM, and preferably less than 5 μM, before formulation. The compounds may be micronised or sonicised by methods known in the art or nanonised, for example by methods disclosed in U.S. Pat. No. 5,145,684.

The compounds in accordance with the present invention may be prepared by a process which comprises reacting a compound of formula III with a compound of formula IV:

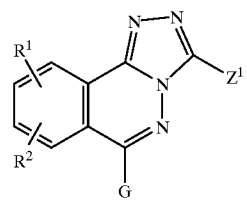

(III)

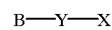

(IV)

wherein $R^1$, $R^2$, X and Y are as defined above, G is a leaving group such as chlorine, $OCH_2CF_3$ or para-sulphonyltoluene, B is LH where L is as defined above and $Z^1$ is a group Z as defined above or is a moiety which can be converted into a group Z by further reaction.

Compounds of formula III represent a further feature of the present invention. The groups Z which are preferred for compounds of formula I are preferred for these compounds likewise.

The reaction between compounds III and IV when L is 0 is conveniently effected by stirring the reactants in a suitable solvent, typically N,N-dimethylformamide, in the presence of a strong base such as sodium hydride or lithium bis (trimethylsilyl)amide, typically without heating and under an inert atmosphere such as nitrogen. When L is $NR^n$ the reaction is conveniently effected in the presence of a strong base such as $Et_3N$ or NaH and a solvent such as DMF or DMSO generally for 15 to 60 hours with heating to 50–120° C.

The intermediates of formula III above may be prepared by reacting a compound of formula V, which constitutes a further feature of the present invention, with a compound of formula VI:

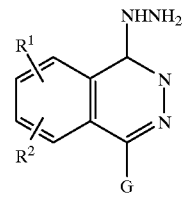

(V)

(VI)

wherein $R^1$, $R^2$, G and $Z^1$ are as defined above, and W represents a suitable leaving group such as $C_{1-6}$alkoxy, chlorine or hydroxy.

The reaction is advantageously conducted in an inert organic solvent, generally in the presence of an organic nitrogen base and preferably under an inert atmosphere such as nitrogen. Suitable solvents include xylene, dioxane, tetrahydrofuran and lower aliphatic halogenated and aromatic hydrocarbons. Suitable organic nitrogen bases that may be employed include trialkylamines and pyridine. The reaction is generally conducted at a temperature range of from −20° C. to the reflux temperature of the reaction mixture, for a period of time that depends on the reactants employed and the temperature at which the reaction is carried out. The compound of formula VI may be activated by reacting with a compound such as bis (2-oxo-3-oxazolidinyl)phosphinic chloride or 1,1'-dicarbonyldiimidazole before reaction with the hydrazine.

When $Z^1$ is not a group Z, it is, for example, an alkyl-formyloxime group which can be converted to a carboxaldehydeoxime using tetrakis(triphenylphosphine)palladium (0) generally under an inert atmosphere such as nitrogen in the presence of triethylammonium formate, in a solvent such as ethanol for about 18 hours. The carboxaldehydeoxime can be converted to a carboxaldehydechloroxime by reacting with a chlorinating agent such as N-chlorosuccinimide in a solvent such as DMF. The carboxaldehydechloroxime can be converted to the desired group Z by reacting with an unsaturated compound such a vinylidene chloride, methyl propargyl ether, 3-phenyl-1-propyne, 2-pyridylacetylene, triiluoromethylacetylene or ethoxyacetylene generally in the presence of a base such a triethylamine, and a solvent, such as dichloromethane. Alternatively, the carboxaldehydechloroxime can be converted to a group Z by reacting with ammonium hydroxide generally in a solvent such as ethanol for about 30 minutes and then acetic anhydride generally with heating to reflux for about 16 hours.

The reaction is advantageously conducted in an inert organic solvent, generally in the presence of an organic nitrogen base and preferably under an inert atmosphere such as nitrogen. Suitable solvents include xylene, dioxane, tetrahydrofuran and lower aliphatic halogenated and aromatic hydrocarbons. Suitable organic nitrogen bases that may be employed include trialkylamines and pyridine. The reaction is generally conducted at a temperature range of from −20° C. to the reflux temperature of the reaction mixture, for a period of time that depends on the reactants employed and the temperature at which the reaction is, carried out. The compound of formula VI may be activated by reacting with a compound such as bis (2-oxo-3-oxazolidinyl)phosphinic chloride or 1,1'-dicarbonyldiimidazole before reaction with the hydrazine.

Compounds of formula III in which G is $OCH_2CF_3$ can be prepared by reacting a compound of formula III in which G is chlorine with 2,2,2-trifluoroethanol in the presence of a base such as lithium bis(trimethylsilyl)amide generally in a solvent such as DMF, preferably With cooling to about −20° C.–0° C. for a period of about 30 minutes.

The compound of formula V is prepared by reaction of a compound of formula VII:

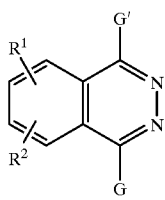

(VII)

where $R^1$, $R^2$ and G are as defined above, and G' is another suitable leaving group which may be the same as or different to G, with hydrazine, usually in the form of its monohydrate, generally in a solvent such as ethanol and generally by refluxing for a suitable period such as 15 minutes to 2 hours.

When the compound of formula VII is asymmetrical, that is $R^1$ and $R^2$ are different or if they are the same, the substitution pattern about the fused benzene ring is not symmetrical, the reaction between this compound and hydrazine will usually give rise to a mixture of isomeric products depending on whether group G or G' is displaced first. Thus in addition to the required product of formula V, the isomeric compound wherein the $R^1$ and $R^2$ moieties are reversed will usually be obtained to some extent. For this reason it will generally be necessary to separate the resulting mixture of isomers by conventional methods such as chromatography.

The compound of formula VII can be used to prepare a compound of formula III in a single step by reacting with the appropriate hydrazoic acid. This is generally carried out in the presence of a base, such as triethylamine, in a solvent such as xylene, at reflux under an inert atmosphere such as nitrogen.

The compound of formula VII can be prepared by reacting a compound of formula X:

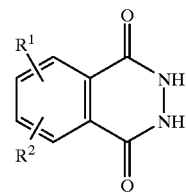

(X)

where $R^1$ and $R^2$ are as defined above, with a suitable reagent for introducing leaving groups G and $G^1$, for example where G and $G^1$ are both chlorine $POCl_3$ can be used generally with heating to reflux for about 16 hours.

The compound of formula X can be prepared by reacting a compound of formula XI with hydrazine hydrate $(H_2NNH_2 \cdot H_2O)$:

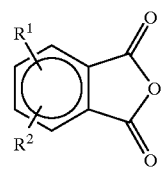

(XI)

where $R^1$ and $R^2$ are as defined above. The reaction is generally carried out in a protic solvent, such as 40% aqueous acetic acid, and in the presence of a buffering agent such as sodium acetate, generally with heating to reflux for about 16 hours.

The compound of formula XI can be prepared by reaction of a compound of formula XII:

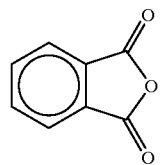

(XII)

with suitable reagents to introduce the substituents $R^1$ and $R^2$ where necessary. For example, when $R^1$ is phenyloxyor pyridyloxy or a derivative thereof, the corresponding hydroxy compound can be used as a reagent. The compound of formula XII is commercially available.

Alternatively, when $R^1$ is the same as L-Y-X in the compound of formula I, it can be introduced by displacing another group $R^1$ which can act as a leaving group, such as fluorine, in the reaction between the compounds of formulae III and IV.

In another procedure, the compounds according to the invention wherein L is O may be prepared by a process which comprises reacting a compound of formula VIII with a compound of formula IX:

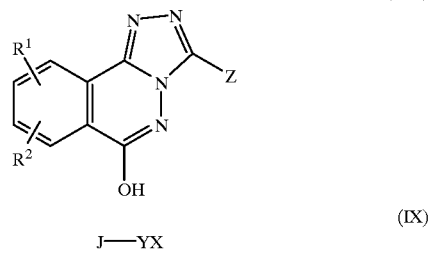

(VIII)

J——YX (IX)

wherein $R^1$, $R_2$, X, Y and Z are as defined above and J represents a suitable leaving group such as a halogen atom, typically chlorine. The reaction between compounds VIII and IX is conveniently effected by stirring the reactants in a suitable solvent, typically N,N-dimethylformamide, in the presence of a strong base such as sodium hydride.

The intermediates of formula VIII above may be conveniently prepared by reacting a compound of formula III as defined above with an alkaline hydroxide, e.g. sodium hydroxide. The reaction is conveniently effected in an inert solvent such as 1,4-dioxane, ideally at the reflux temperature of the solvent. A compound of formula III in which G is parasulphonyltoluene can be made by reacting a compound of formula VIII with 4-toluenesulphonylchloride.

Where they are not commercially available, the starting materials of formula IV, VI, VIII and IX may be prepared by methods analogous to those described in the accompanying Examples, or by standard methods known from the art.

It will be understood that any compound of formula I initially obtained from the above process may, where appropriate, subsequently be elaborated into a further compound of formula I by techniques known from the art.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (-)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The compounds in accordance with this invention potently inhibit the binding of [$^3$H]-flumazenil to the benzodiazepine binding site of human $GABA_A$ receptors containing the α5 subunit stably expressed in Ltk cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 1M in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e;g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]Ro 15-1788 from the α5 subunit of the human $GABA_A$ receptor of 100 nM or less, most were at 50 nM or less, many were at 10 nM or less and some were at 1 nM or less.

The compounds of the present invention have been shown to enhance cognition in the rat water maze test (Morris, Learning and Motivation, 1981, 12, 239ff). Further details of methodology for demonstrating that the present compounds enhance cognition can be found in WO-A-9625948.

The following Examples illustrate the present invention:

INTERMEDIATE 1

6-Chloro-3-(5-Methylisoxazol-3-yl)-1,2,4-triazolo[3,4-a]phthalazine a) 1-Chloro-4-hydrazinophthalazine 1,4-Dichlorophthalazine (20.0g, 0.100 mol) was added to a boiling isolution of hydrazine monohydrate (37.3 ml, 0.765 mol) in ethanol (500 ml) and the mixture heated at reflux for 0.5 h. The mixture was cooled to room temperature and the solid collected by filtration and washed with ether. The material was taken with n-butanol and ammonia solution (sp. gr. 0.91) and heated until the solid dissolved. The organic layer was separated, evaporated in vacuo and the residue azeotroped with xylene (×2) and dried in vacuo to give the title-hydrazine (11.5 g, 59%), $^1$H NMR (250 MHz, d$^6$DMSO) δ 7.84–8.04 (3H, m, Ar—H), 8.20 ($^1$H, m, Ar—H); MS (ES$^+$) m/e 194 [MH]$^+$.

b) 5-Methylisoxazole-3arboxyhic acid

A mixture of acetonylacetone (10 g, 88 mmol) and nitric acid (sp. gr. 1.42)/water (2:3) (50 ml) was cautiously brought to reflux under a stream of nitrogen and boiled for 1 h. The solution was cooled to room temperature and aged overnight. The resultant solid was collected by filtration, washed with chilled water (2×7 ml) and hexane, and dried in vacuo to give the title-acid (4.4 g, 40%), $^1$H NMR (CDCl$_3$) δ 2.50 (3H, d, J=0.8 Hz, Me), 6.41 (1H, d, J=0.8 Hz, Ar—H).

c) 6-Chloro-3-(5-Methylisoxazol-3-yl)-1,2,4-triazolo[3,4-a]phthalazine

5-Methylhsoxazole-3-carboxylic acid (5.24 g, 41.3 mmol), bis(2-oxo-3-oxazolidinyl)phosphinic chloride (10.5 g, 41.2 mmol) and triethylamine (11.5 ml, 82.5 mmol) were added successively to a stirred suspension of 1-chloro-4-hydrazinophthalazine (8.00 g, 41.2 mmol) in dichloromethane (1 l) at 0° C. under nitrogen. The mixture was'stirred at 0° C. for 2 h and at room temperature overnight. The solvent was evaporated in vacuo, the residue triturated with water and the solid filtered off, washed with hexane and dried in vacuo to give the ketohydrazine (11 g), MS (ES$^+$) m/e 304 [MH]$^+$. A solution of the ketohydrazine (11 g) and triethylamine hydrochloride (2.2 g, 20% w/w) in xylene (500 ml) was heated at reflux for 3 h. The mixture was cooled to room temperature and the solvent evaporated in vacuo. The residue was dissolved in dichloromethane, washed with water (×2), dried (MgSO$_4$) and evaporated in vacuo, and the solid recrystallised (dichloromethane/hexane) to give the title-compound (6.8 g, 58%), $^1$H NMR (360 MHz, CDCl$_3$) δ 2.59 (3H, s, Me), 6.90 (1H, s, Ar—H), 7.95 (1H, m, Ar—H), 8.07 (1H, m, Ar—H), 8.34 (1H, m, Ar—H), 8.78 (1H, s, Ar—H); MS (ES$^+$) m/e 286 [MH]$^+$.

EXAMPLE 1

3-(5-Methylisoxazol-3-yyl-6-(2-pyridyl)methyloxy-1,2,4-triazolo[3,4-a]phthalazine Sodium hydride (244 mg of a 60% dispersion in oil, 6.10 mmol) was added to a stirred solution of 2-pyridylcarbinol (470 mg, 4.27 mmol) in DMF (60 ml) at room temperature under nitrogen and the mixture stirred for 0.25 h. After this time, Intermediate 1 (1160 mg, 4.07 mmol) was added and the mixture stirred for 2 h. The solvent was removed in vacuo and the residue dissolved in dichloromethane, washed with water (×2), dried MgSO$_4$) and evaporated in vacuo. Flash chromatography on silica gel eluting with 3% methanol/dicloromethane followed by recrystallisation (dichloromethane/hexane) gave the title-product (640 mg, 44%), mp 234–236° C.; $^1$H NMR (360 MHz, CDCl$_3$) δ 2.59 (3H, d, J=0.8 Hz, Me), 5.77 (2H, s, CH$_2$), 6.82 (1H, d, J=0.8 Hz, Ar—H), 7.30 (1H, m, Ar—H), 7.74–7.85 (3H, m, Ar—H), 7.95 (1H, m, Ar—H), 8.33 (1H, d, J=7.8 Hz, Ar—H), 8.64–8.72 (2H, m, Ar—H); MS (ES$^+$) m/e 359 [MH]$^+$; Anal. Found. C, 62.93; H, 3.56; N, 22.94. C$_{19}$H$_{14}$N$_6$O$_2$ 0.05 (CH$_2$Cl$_2$) requires C, 63.10; H, 3.92; N, 23.17%.

EXAMPLE 2

3-(5-Methylisoxazol-3-yl)-6-(6-methylpyridin-2-yl)methyloxy-1,2,4-triazolo[3,4-a]phthalazine The title-compound was prepared from Intermediate 1 and 6-methyl-2-pyridylcarbinol using the procedure given for Example 1, $^1$H NMR (360 MHz, CDCl$_3$) δ 2.59 (3H, d, J=0.8 Hz, Me), 2.61 (3H, s, Me), 5.73 (2H, s, CH$_2$), 6.86 (1H, d, J=0.8 Hz, Ar—H), 7.16 (1H, d, J=7.6 Hz, Ar—H), 7.53 (1H, d, J=7.5 Hz, Ar—H), 7.66 (1H, t, J=7.7 Hz, Ar—H), 7.83 (1H, m, Ar—H), 7.97 (1H, t, J=8.2 Hz, Ar—H), 8.33 (1H, d, J=7.7 Hz, Ar—H), 8.70 (1H, d, J=7.7 Hz, Ar—H); MS (ES$^+$) m/e 373 [MH]$^+$; Anal. Found. C, 60.72; H, 4.15; N, 21.20. C$_{20}$H$_{16}$N$_6$O$_2$.1.15 (H$_2$O) requires C, 61.11; H, 4.69; N, 21.38%.

EXAMPLE 3

3-(5-Methylisoxazol-3-yl)-6-(3-pyridyl)methylox-1,2,4-triazolo[3,4-a]phthalazine The title-compound was prepared from Intermediate 1 and pyridine-3-methanol using the procedure given for Example 1, mp 226–228° C.; $^1$H NMR (360 MHz, CDCl$_3$) δ 2.59 (3H, d, J=0.6 Hz, Me), 5.69 (2H, s, CH$_2$), 6.83 (1H, d, J=0.8 Hz, Ar—H), 7.37 (1H, m, Ar—H), 7.79 (1H, t, J=8.4 Hz, Ar—H), 7.95 (1H, t, J=8.6 Hz, Ar—H), 8.08 (1H, d, J=7.8 Hz, Ar—H), 8.22 (1H, d, J=8.5 Hz, Ar—H), 8.65 (1H, d, Ar—H), 8.70 (1H, d, Ar—H), 8.93 (1H, br s, Ar—H); MS (ES$^+$) m/e 359 [MH$^+$; Anal, Found. C, 63.54; H, 3.70; N, 23.10. C$_{19}$H$_{14}$N$_6$O$_2$ requires C, 63.68; H, 3.94, N 23.45%.

EXAMPLE 4

3-(5-Methylisoxazol-3-yl)-6-(4-pyridyl)methyloxy-1,2,4-triazolo[3,4-a]phthalazine The title-compound was prepared from Intermediate 1 and pyridine-4-methanol using the procedure given for Example 1, mp 244–246° C.; $^1$H NMR (360 MHz, CDCl$_3$) δ 2.58 (3H, s, Me), 5.68 (2H, s, CH$_2$), 6.79 (1H, s, Ar—H), 7.57 (2H, br s, Ar—H), 7.85 (1H, t, J=7.3 Hz, Ar—H), 7.98 (1H, t, J=7.9 Hz, Ar—H), 8.29 (1H, d, 8.0 Hz, Ar—H), 8.70 (2H, d, Ar—H); MS (ES$^+$) m/e 359 [MH]$^+$; Anal. Found C, 62.81; H, 3.93; N, 22.78. C$_{19}$H$_{14}$N$_6$O$_2$. 0.3 (H$_2$O) requires C, 62.74; H, 4.04; N, 23.10%.

EXAMPLE 5

6-(3.5-Dimethylpyrazol-1-yl)methyloxy-3-(5-methylisoxazol-3-yl)-1,2,4-triazolo[3,4-a]phthalazine The title-compound was prepared from Intermediate 1 and 3,5-dimethylpyrazole-1-methanol using the procedure given in Example 1 mp 229–231° C.; $^1$H NMR (360 MHz, CDCl$_3$) δ 2.27 (3H, s, Me), 2.41 (3H, s, Me), 2.61 (3H, s, Me), 5.98 (1H, s, Ar—H), 6.49 (2H, s, CH$_2$), 6.96 (1H, d, J=0.8 Hz, Ar—H), 7.83 (1H, t, J=8.4 Hz, Ar—H), 8.02 (1H, t, J=8.3 Hz, Ar—H), 8.20 (1H, d, J=7.8 Hz, Ar—H), 8.70 (1H, d, Ar—H); MS (ES$^+$) m/e 376 [MH]$^+$, Anal. Found. C, 59.65; H, 4.13; N, 25.26. C$_{19}$H$_{17}$N$_7$O$_2$.0.1 (CH$_2$Cl$_2$) requires C, 59.76; H, 4.51, N, 25.54%.

EXAMPLE 6

6-(3-Methoxypyridin-2-yl)methyloxy-3-(5-methylisoxazol-3-yl)-1,2,4-triazolo[3,4-a]phthalazine a) 3-Methoxy(2-hydroxymethyl)pyridine To a mixture of ground potassium hydroxide (10.2 g, 0.186 mol) in dimethylsulphoxide (15 ml) under nitrogen was added 3-hydroxy(2-hydroxymethyl)pyridine hydrochloride (5.0 g, 0.031 mol) in dimethylsulphoxide (15 ml) over 0.25 h. The reaction was stirred at room temperature for 1 h before the addition of methyl iodide (1.92 ml, 0.0309 mol) and then stirred at room temperature overnight. Water (100 ml) was added and the solution acidified to pH 1 with 2N hydrochloric acid, washed with dichloromethane (×3) and then basified-with solid potassium carbonate until pH 12 was attained. The aqueous was extracted with dichloromethane (×3), dried (MgSO$_4$), evaporated in vacuo and the residue purified by chromatography on silica gel, eluting with dichloromethane/methanol/ammonia (90:5:0.5), to give the title-compound (300 mg, 7%). $^1$H NMR (360 MHz, CDCl$_3$) δ 3.85 (3H, s, CH$_3$), 4.74 (2H, s, CH$_2$), 7.12 (1H, d, J 8.3 Hz, Ar—H), 7.21 (1H, m, Ar—H), 8.15 (1H, d, J=4.8 Hz, Ar—H).

b) 3-(5-Methylisoxazol-3-yl)-6-(3-methoxypyridin-2-yl)methyloxy-1,2,4-triazolo[3,4-a]phthalazine The title-compound was prepared from Intermediate 1 and the preceding alcohol using the procedure given for Example 1, mp 243–245° C.; $^1$H NMR δ (360 MHz, CDCl$_3$) δ 2.59 (3H, d, J=0.5 Hz, Me), 3.90 (3H, s, OMe), 5.79 (2H, s, CH$_2$), 6.87 (1H, d, J=0.8 Hz, Ar—H), 7.34 (2H, m, Ar—H), 7.76 (1H, t, J=8.2, Ar—H), 7.93 (1H, t, J=8.1 Hz, Ar—H), 8.25 (1H, m, Ar—H), 8.70 (1H, d, Ar—H); MS (ES$^+$) m/e 389 [MH]$^+$; Anal. Found. C, 62.03; H, 3.68; N, 21.52. C$_{20}$H$_{16}$N$_6$O$_3$ requires C, 61.85; H, 4.15; N, 21.18%.

EXAMPLE 7

6-(5-Methylisoxazol-3-yl)methyloxy-3-(5-methylisoxazol-3-yl)-1,2,4-triazolo[3,4-a]phthalazine The title-compound was prepared from Intermediate 1 and 5-methylisoxazole-3-methanol using the procedure given for Example 1, mp 243–245° C.; $^1$H NMR (360 MHz, CDCl$_3$) δ 2.45 (3H, s, Me), 2.60 (3H, s, Me), 5.70 (2H, s, CH$_2$), 6.43 (1H, s, Ar—H), 6.88 (1H, d, J=0.7 Hz, Ar—H), 7.81 (1H, t, J=8.2 Hz, Ar—H), 7.98 (1H, t, J=8.1 Hz, Ar—H), 8.24 (1H, d, J=7.9 Hz, Ar—H), 8.70 (1H, d, Ar—H); MS (ES$^+$) m/e 347 [MH]$^+$; Anal. Found. C, 59.45; H, 3.62; N, 22.80. C$_{18}$H$_{14}$N$_6$O$_2$ requires C, 59.67; H 3.89; N, 23.19%.

EXAMPLE 8

3-(5-Methylisoxazol-3-yl)-6-(pyrazol-1-yl)methyloxy-1,2,4-triazolo [3,4-a]phthalazine a) Pyrazole-1-methanol To a solution of pyrazole (1.0 g, 0.015 mol) in tetrahydrofuran (40 ml) at room temperature was added formaldehyde (37% aq) (1.19 g, 0.0147 mol) and the mixture stirred for 16 h. The solvent was removed in vacuo to give the title-alcohol (1.36 g, 94%). $^1$H NMR (250 MHz, CDCl$_3$) δ 5.53 (2H, s, CH$_2$), 6.30 (1H, t, J=3.1 Hz, Ar—H), 7.58–7.60 (2H, m, Ar—H).

b) 3-(5-Methylisoxazol-3-yl)-6-(pyrazol-1-yl)methyloxy-1,2,4-triazolo[3,4-a]phthalazine The title-compound was prepared from Intermediate 1 and pyrazole-1-methanol using the procedure given for Example 1, mp 235–237° C.; $^1$H NMR (360 MHz, CDCl$_3$) δ 2.60 (3H, d, J=0.7 Hz, Me), 6.29 (1H, t, J=2.5 Hz, Ar—H), 6.61 (2H, s, CH$_2$), 6.91 (1H, d, J=0.8 Hz, Ar—H), 7.61 (1H, s, Ar—H), 7.81 (1H, t, J=10.4 Hz, Ar—H), 7.95 (1H, t, J=7.5 Hz, Ar—H), 8.25 (1H, d, J=7.8 Hz, Ar—H), 7.70 (2H, m, Ar—H); MS (ES$^+$) m/e 348 [MH]$^+$.

EXAMPLE 9

6-(6-Chloropyridin-2-yl)methyloxy-3-(5-methylisoxazol-3-yl)-1,2,4-triazolo[3 4-a]phthalazine a) 2-Chloropyridine-6-methanol m-Chloroperbenzoic acid (50%) (16.2 g, 94 mmol) was added over 0.75 h to a solution of 2-chloro-6-methylpyridine (5 g, 39 mmol) in dichloromethane (100 ml) at 0° C., and the mixture stirred at room temperature overnight. Further mCPBA (2.7 g, 15 mmol) in dichloromethane (20 ml) was added and stirred for 2 h.

Sodium hydroxide solution (4M, 15 ml) was added and the organic layer separated, dried (MgSO$_4$) and evaporated in vacuo to give the N-oxide (5.13 g). The N-oxide (7.74 g,) was added slowly to acetic anhydride (15 ml) at 110° C. with stirring. The mixture was heated at 110° C. for 2 h, cooled to room temperature and distilled in vacuo to give the acetate (4.8 g), bp 98–104° C. at 1.8 mbar. A solution of the acetate (4.8 g) in methanol/HCl solution (1:1) was stirred for 5 h at room temperature. The mixture was basified by addition of sodium hydroxide solution (1M), and extracted into dichloromethane. The organic extracts were washed with brine (×1), dried (MgSO$_4$) and evaporated in vacuo and the residue flash chromatographed on silica gel, eluting with 2% methanol/dichloromethane to give the title-alcohol (2.02 g), $^1$H NMR (250 MHz, CDCl$_3$), δ 4.75 (2H, s, CH$_2$), 7.24 (2H, m, 2 of Ar—H) 7.66 (1H, t, J=7.7 Hz, Ar—H); MS (ES$^+$) m/e 144 [MH]$^+$.

b) 6-(6-Chloropyridin-2-yl)methyloxy-3-(5-methylisoxazol-3-yl)-1,2,4-triazolo[3,4-a]phthalazine The title-compound was prepared from the preceding alcohol and Intermediate 1 following the procedure given for Example 1, mp 240–242° C.; $^1$H NMR (360 MHz, CDCl$_3$) δ 2.60 (3H, d, J=0.6 Hz, Me), 5.73 (2H, s, CH$_2$), 6.82 (1H, d, J=0.7 Hz, Ar—H), 7.33 (1H, m, Ar—H), 7.72–7.74 (2H, m, Ar—H), 7.84 ((1H, t, J=8.3 Hz, Ar—H), 7.99 (1H, t, J=8.2 Hz, Ar—H), 8.31 (1H, d, J=7.8 Hz, Ar—H), 8.70 (1H, d, Ar—H); MS (ES$^+$) m/e 393 [MH]$_+$; Anal. Found. C, 58.58; H, 3.11; N, 21.32. C$_{19}$H$_{13}$N$_6$O$_2$Cl requires C, 58.10; H, 3.34; N, 21.39%.

EXAMPLE 10

6-(6-Bromopyridin-2-yl)methyloxy-3-(5-methylisoxazol-3-yl)-1,2,4-triazolo[3,4-a]phthalazine The title-compound was prepared from Intermediate 1 and 2-bromopyridine-6-methanol (*Tetrahedron Lett.*, 1996, 50, 2537) following the procedure given for Example 1. The product was isolated by addition of water to the reaction mixture and the resulting precipitate was filtered off. Flash chromatography on silica gel, eluting with ethyl acetate, and recrystallisation (ethyl acetate-methanol) gave the title-phthalazine, mp 247.5–249° C.; $^1$H NMR (360 MHz, CDCl$_3$) δ 2.61 (3H, d, J=0.7 Hz, Me), 5.73 (2H, s, CH$_2$), 6.82 (1H, d, J=0.7 Hz, Ar—H), 7.48 (1H, d, J=7.8 Hz, Ar—H), 7.63 (1H, t, J=7.7 Hz, Ar—H), 7.76 (1H, d, J=7.4 Hz, Ar—H), 7.84 (1H, t, J=8.4 Hz, Ar—H), 7.98 (1H, t, J=8.4 Hz, Ar—H), 8.31 (1H, d, J=8.5 Hz, Ar—H), 8.70 (1H, d, Ar—H); MS (ES$^+$) m/e 437 [MH]$^+$; Anal. Found C, 52.27; H, 2.85; N, 19.14. C$_{19}$H$_{13}$N$_6$O$_2$ Br. 0.1 (H$_2$O) requires C, 51.98; H, 3.03; N, 18.60%.

EXAMPLE 11

6-(6-Methoxypyridin-2-yl)methyloxy-3-(5-methylisoxazol-3-yl)-1,2,4-triazolo[3,4-a]phthalazine a) 6-Bromo-2-[(tetrahydropyran-2-yl)oxmethyl]pyridine 2-Bromopyridine-6-methanol (prepared as described in *Tetrahedron Lett.*, 1996, 50, 2537) (5 g, 26.5 mmol) was added to a solution of dihydropyran (2.65 ml, 29.2 mmol), and p-toluenesulfonic acid (506 mg, 2.7 mmol) in dichloromethane (150 ml) at room temperature under nitrogen.

After 24 h, the mixture was washed with sodium carbonate solution (×1) and water (×1), dried (MgSO$_4$), evaporated in vacuo and the residue flash chromatographed on silica gel, eluting with 10% ethyl acetate/hexane to give the title-compound (6.04 g, 84%), $^1$H NMR (250 MHz, CDCl$_3$) δ 1.5–1.9 (6H, m, 3 of CH$_2$), 3.56 (1H, m, CH$_2$O), 3.88 (1H, m, CH$_2$O), 4.62 (1H, d, J=14.2 Hz, CH$_2$O), 4.76 (1H, t, J=3.4 Hz, CHO), 4.93 (1H, d, J=14.6 Hz, CH$_2$O), 7.37 (1H, d, J=7.6 Hz, Ar—H), 7.46 (1H, d, J=6.6 Hz, Ar—H), 7.56 (1H, t, J=7.6 Hz, Ar—H); MS (ES$^+$) m/e 272 [MH]$^+$.

b) 6-Methoxy-2-[(tetrahydropyran-2-yl)oxymethyl]pyridine

Methanol (467 mg, 14.5 mmol) was added to a stirred mixture of sodium hydride (595 mg of a 60% dispersion in oil, 14.9 mmol) in N,N-dimethylformamide (20 ml) at room temperature under nitrogen, and the mixture stirred for 0.75 h. The preceding bromide was added in N,N-dimethylformamide (5 ml) and the reaction mixture stirred for 24 h. The solvent was removed in vacuo and the residue partitioned between water and ethyl acetate. The aqueous phase was extracted with ethyl acetate (×3) and the combined extracts dried (MgSO$_4$) and evaporated in vacuo to give the title-compound (666 mg). $^1$H NMR (250 MHz, CDCl$_3$), δ 1.5–1.9 (6H, m, 3 of CH$_2$), 3.57 (1H, m, CH$_2$O), 3.95 (4H, m, CH$_2$O and OMe), 4.55 (1H, d, J=13.7 Hz, CH$_2$O), 4.78 (2H, m, CH, CH$_2$O), 6.61 (1H, d, J=8.2 Hz, Ar—H), 7.02 (1H, d, J=7.3 Hz, Ar—H), 7.56 (1H, m, Ar—H); MS (ES$^+$) m/e 224 [MH]$^+$.

c) 2-Methyloxypyridine-6-methanol

Pyridinium p-toluenesulphonate (75 mg, 0.3 mmol) was added to a solution of the preceding product (666 mg, 3.0 mmol) in ethanol (2 ml) at room temperature under nitrogen. The mixture was heated at 55° C. for 3 h then cooled and the solvent removed in vacuo. Flash chromatography of the residue on silica gel, eluting with 30% ethyl acetate/hexane, gave the title-compound (204 mg, 50%) $^1$H NMR (250 MHz, CDCl$_3$) δ 3.52 (1H, br s, OH), δ 3.96 (3H, s, Me), 4.68 (2H, s, CH$_2$), 6.64 (1H, d, J=8.2 Hz, Ar—H), 6.80 (1H, d, J=7.2 Hz, Ar—H), 7.56 (1H, dd, J=8.2 and 7.3 Hz, Ar—H); MS (ES$^+$) m/e 140 [MH]$^+$.

d) 6-(6-Methoxypyridin-2-yl)methyloxy-3-(5-methylisoxazol-3-yl)-1,2,4-triazolo[3,4-a]phthalazine The title-compound was prepared from Intermediate 1 and the preceding alcohol using the procedure described for Example 10, mp 211–213° C.; $^1$H NMR (360 MHz, CDCl$_3$), δ 2.57 (3H, d, J=0.7 Hz, Me), 3.95 (3H, s, OMe), 5.65 (2H, s, CH$_2$), 6.72 (1H, d, J=8.4 Hz, Ar—H), 6.78 (1H, d, J=0.8 Hz, Ar—H), 7.20 (1H, m, Ar—H), 7.62 (1H, m, Ar—H), 7.83 (1H, m, Ar—H), 7.97 (1H, m, Ar—H), 8.32 (1H, d, J=8.6 Hz, Ar—H), 8.70 (1H, d, Ar—H); MS (ES$^+$) m/e 389 [MH]$^+$; Anal. Found. C, 62.13; H, 3.88; N, 21.83. C$_{20}$H$_{16}$N$_6$O$_3$ requires C, 61.85; H, 4.15; N, 21.64%.

EXAMPLE 12

6-(6-Isopropoxylpyridin-2-yl)methyloxy-3-(5-methylisoxazol-3-yl)-1,2,4-triazolo[3,4-a]phthalazine a) 6-Isopropoxy-2-[(tetrahydropyran-2-yl)oxymethyl]pyridine The title-compound was prepared from 6-bromo-2-[(tetrahydropyran-2-yl)oxymethyl]pyridine prepared following the procedure given for Example 11 part a and isopropyl alcohol following the procedure given for Example 11 part b, $^1$H NMR (250 MHz, CDCl$_3$), δ 1.32 (6H, d, J=6.2 Hz, 2 of CH$_3$), 1.6–1.9 (6H, Me, 3 of CH$_2$), 3.56 (1H, m, CH$_2$O), 3.91 (1H, m, CH$_2$O), 4.53 (1H, d, J=13.7 Hz, CH$_2$O), 4.76 (1H, d, J=13.6 Hz, CH$_2$O), 4.79 (1H, m, CHO), 5.29 (1H, septet, J=6.2 Hz, CH), 6.55 (1H, d, J=8.2 Hz, Ar—H), 6.96 (1H, d, J=7.3 Hz, Ar—H), 7.53 (1H, dd, J=8.2 and 7.3 Hz, Ar—H); MS (ES$^+$) m/e 252 [MH]$^+$.

b) 2-Isopropoxypyridine-6-methanol

The title-compound was prepared from the preceding isopropoxypyridine using the procedure given for Example 11 part c, $^1$H NMR (250 MHz, CDCl$_3$), δ 1.36 (6H, d, J=6.2 Hz, 2 of CH$_3$), 3.51 (1H, br t, OH), 4.65 (2H, d, J=3.5 Hz, CH$_2$), 5.31 (1H, septet, J=6.2 Hz, CH), 6.58 (1H, dd, J=8.2 and 0.6 Hz, Ar—H), 6.74 (1H, dd, J=7.3 and 0.8 Hz, Ar—H), 7.54 (1H, dd, J=8.2 and 7.3 Hz, Ar—H); MS (ES$^+$) m/e 168 [MH]$^+$.

c) 6-(6-Isopropoxypyridin-2-yl)methyloxy-3-(5-methylisoxazol-3-yl)-1,2,4-triazolo[3,4-a]phthalazine The title-compound was prepared from Intermediate 1 and the preceding alcohol using the procedure described for Example 10, mp 188–190° C.: $^1$H NMR (360 MHz. CDCl$_3$) δ 1.32 (6H, d, J=6.2 Hz, 2 of CH$_3$), 2.57 (3H, d, J=0.7 Hz, Me), 5.30 (1H, septet, J=6.5 Hz, CH), 5.63 (2H, s, CH$_2$), 6.66 (1H, d, J=8.3 Hz, Ar—H), 6.80 (1H, s, Ar—H), 7.15 (1H, d, J=7.5 Hz, Ar—H), 7.60 (1H, t, J=8.3 Hz, Ar—H), 7.83 (1H, t, J=8.4 Hz, Ar—H), 7.97 (1H, t, J=8.6 Hz, Ar—H), 8.31 (1H, d, J=7.8 Hz, Ar—H), 8.70 (1H, d, Ar—H); MS (ES$^+$) m/e 417 [MH]$^+$; Anal. Found. C, 63.84; H, 4.57; N, 19.96%; C$_{22}$H$_{20}$N$_6$O$_2$ requires C, 63.45; H, 4.84; N, 20.18%.

EXAMPLE 13

6-(6-N,N-Dimethylpyridin-2-yl)methyloxy-3-(5-methylisoxazol-3-yl)-1,2,4-triazolo[3,4-a]phthalazine a) (6-N,N-Dimethyl-2-[-(tetrahydropyran-2-yl)oxymethyl]pyridine A mixture of 6-bromo-2-[(tetrahydropyran-2-yl)oxymethyl]pyridine (400 mg, 15 mmol) prepared following the procedure given for Example 11 part a and dimethylamine (10 ml of a 33% solution in ethanol) was heated at reflux for 48 h and then heated in a sealed tube at 120° C. for 18 h. The solvent was removed in vacuo and the residue taken up in ethyl acetate, washed with sodium carbonate solution (×1), dried (MgSO$_4$) and evaporated in vacuo. Flash chromatography of the residue on silica gel, eluting with 15% diethyl ether/hexane, gave the title-compound (298 mg, 86%), $^1$H NMR (250 MHz, CDCl$_3$), δ 1.5–1.8 (6H, m, 3 of CH$_2$), 3.07 (6H, s, 2 of CH$_3$), 3.55 (1H, m, CH$_2$O), 3.95 (1H, m, CH$_2$O), 4.51 (1H, d, J=13.5 Hz, CH$_2$O), 4.74 (1H, d, J=13. 5 Hz, CH$_2$O), 4.80 (1H, m, CH), 6.40 (1H, d, J=8.5 Hz, Ar—H), 6.69 (1H, d, J=7.2 Hz, Ar—H), 7.44 (1H, dd J=8.3 and 7.4 Hz, Ar—H); MS (ES$^+$) m/e 237 [MH]$^+$.

b) 6-N,N-dimethylpyridine-2-methanol

The title-compound was prepared from the preceding pyridine using the procedure given for Example 11 part c, $^1$H NMR (250 MHz, CDCl$_3$), δ 3.91 (6H, s, 2 of CH$_3$), 4.21 (1H, br s, OH), 4.61 (2H, s, CH$_2$), 6.40 (2H, t, J=7.9 Hz, Ar—H), 7.43 (1H, t, J=7.8 Hz, Ar—H); MS (ES$^+$) m/e 153 [MH]$^+$.

c) 6-N,N-Dimethylpyridin-2-yl)methyloxy-3-(5-methylisoxazol-3-yl)-1,2,4-triazolo[3,4-a]phthalazine The title-compound was prepared from Intermediate 1 and the preceding alcohol following the procedure described for Example 10, mp 188–190° C.; $^1$H NMR (360 MHz, CDCl$_3$), δ 2.56 (3H, d, J=0.6 Hz, CH$_3$), 3.09 (6H, s, 2 of CH$_3$), 5.59 (2H, S, CH$_2$), 6.48 (1H, d, J=8.5 Hz, Ar—H), 6.79 (1H, s, Ar—H), 6.81 (1H, d, J=7.3 Hz, Ar—H), 7.49 (1H, t, J=7.8 Hz, Ar—H), 7.82 (1H, m, Ar—H), 7.95 (1H, m, Ar—H), 8.33 (1H, d, J=7.8 Hz, Ar—H), 8.70 (1H, d, Ar—H); MS (ES$^+$) m/e 402 [MH]$^+$; Anal. Found. C, 63.09; H, 4.49; N, 24.18%; C$_{21}$H$_{19}$N$_7$O$_2$ requires C, 62.83; H, 4.77; N, 24.42%.

EXAMPLE 14

6-[6-(Imidazol-1-yl)pyridin-2-yl]methyloxy-3-(5-methylisoxazol-3-yl)-1,2,4-triazolo[3,4-a]phthalazine a) 6-(Imidazol-1-yl)-2-[(tetrahydropyran-2-yl)oxymethyl]pyridine Imidazole (500 mg, 74 mmol) was added to a stirred mixture of sodium hydride (300 mg of a 60% dispersion in oil, 75 mmol) and dimethylformamide (20 ml), at room temperature under nitrogen. After 0.75 h, 6-bromo-2-[(tetrahydropyran-2-yl)oxymethyl]pyridine (400 mg 14.6 mmol) prepared following the procedure given for Example 11 part a in dimethylformamide (5 ml) was added. The mixture was heated at 80° C. for 24 h then in a sealed tube at 120° C. for 4 h. The solvent was evaporated in vacuo and the residue partitioned between water and ethyl acetate. The aqueous phase was separated and extracted with ethyl acetate (×3). The combined extracts were dried ($MgSO_4$), and evaporated in vacuo and the residue flash chromatographed on silica gel, eluting with 5% methanol/dichloromethane to give the title-compound (280 mg, 73%), $^1$H NMR (250 MHz, $CDCl_3$), δ 1.5–1.8 (6H, m, 3 of $CH_2$), 3.58 (1H, m, $CH_2O$), 3.93 (1H, m, $CH_2O$), 4.66 (1H, d, J=14.1 Hz, $CH_2O$), 4.82 (1H, d, CH), 4.90 (1H, d, J=14.1 Hz, $CH_2O$), 7.19 (1H, br s, Ar—H), 7.24 (1H, d, J=8.2 Hz, Ar—H), 7.43 (1H, dd, J=7.6 Hz and 7.1 Hz, Ar—H), 7.64 (H, t, J=1.2 Hz, Ar—H), 7.83 (1H, t, J=7.9 Hz, Ar—H), 8.35 (1H, s, Ar—H); MS ($ES^+$) m/e 260 $[MH]^+$.

b) 2-(Imidazol-1-yl)pyridine-6-methanol

The title-compound was prepared from the preceding pyridine following the procedure given for Example 11 part c. $^1$H NMR (250 MHz, $CDCl_3$), δ 4.81 (2H, s, $CH_2$), 7.20 (1H, s, Ar—H), 7.24–7.29 (2H, m, 2 of Ar—H), 7.64 (1H, t, J=1.3 Hz, Ar—H), 7.84 (1H, t, J=7.9 Hz, Ar—H), 8.35 (1H, s, Ar—H); MS ($ES^+$) m/e 176 $[MH]^+$.

c) 6-[6-(Imidazol-1-yl)pyridin-2-yl methyloxy-3-(5-methylisoxazol-3-yl)-1,2,4-triazolo[3,4a]phthalazine The title-compound was prepared from Intermediate 1 and the preceding alcohol using the procedure described for Example 10, mp 126–127° C.; $^1$H NMR (360 MHz, $CDCl_3$), δ 2.53 (3H, d, J=0.7 Hz, Me), 5.78 (2H, s, $CH_2$), 6.78 (1H, d, J=0.8 Hz, Ar—H), 7.22 (1H, s, Ar—H), 7.34 (1H, d, J=8.1 Hz, Ar—H), 7.66 (2H, s, 2 of Ar—H), 7.80–7.90 (2H, m, 2 of Ar—H), 7.98 (1H, t, J=7.5 Hz, Ar—H), 8.33 (1H, d, J=8.4 Hz, Ar—H), 8.40 (1H, s, Ar—H), 8.70 (1H, d, Ar—H); MS ($ES^+$) m/e 425 $[MH]^+$; Anal. Found. C, 62.48; H, 3.49; N, 25.97. $C_{22}H_{16}N_8O_2 \cdot 0.05 H_2O$ requires C, 62.13; H, 3.82; N, 26.35%.

INTERMEDIATE 2

6-Hydroxy-3-(5-Methylisoxazol-3-yl)-1,2,4-triazolo[3,4-a]phthalazine

A solution of sodium hydroxide (0.67 g, 17 mmol) in water (7.5 ml) was added to a stirred solution of Intermediate 1 (1.0 g, 3.5 mmol) in dioxane (37.5 ml) and the mixture heated at reflux for 4 h. The solvent was evaporated in vacuo and the residue partitioned between water and diethyl ether. The aqueous layer was separated, washed with ether (×1) and then acidified with 2N hydrochloric acid until $pH_2$ was attained. The solid which precipitated out of solution was filtered off and the aqueous filtrate extracted with dichloromethane (×3). The combined extracts were dried ($MgSO_4$) and evaporated in vacuo and combined with the precipitate to give the title-product (0.45 g, 48%), $^1$H NMR (250 MHz, $d^6$-DMSO) δ 2.58 (3H, d, J=0.7 Hz, Me), 7.07 (1H, d, J=0.9 Hz, Ar—H), 7.94 (1H, m, Ar—H), 8.08 (1H, m, Ar—H), 8.24 (1H, d, J=7.4 Hz, Ar—H), 8.54 (1H, d, J=7.4 Hz, Ar—H), 13.32 (1H, br s, NHM; MS ($ES^+$) m/e 268 $[MH]^+$.

EXAMPLE 15

3-(5-Methylisoxazol-3-yl)-6-(3-pyridazino)methyloxy-1,2,4-triazolo[3,4-a]phthalazine a) 3-Chloromethylpyridazine Trichloroisocyanuric acid (1.04 g, 4.46 mmol) was added to a boiling solution of 3-methylpyridazine (1.00 g, 10.6 mmol) in chloroform (30 ml) under nitrogen and the mixture heated at reflux overnight. The mixture was cooled to room temperature, diluted with dichloromethane and filtered through a pad of celite. The filtrate was washed with 1N sodium hydroxide solution (2×100 ml) and brine (×2), dried $MgSO_4$) and evaporated in vacuo to give 3chloromethylpyridazine.

b) 3-(5-Methylisoxazol-3yl)-6-(pyridazino)methyloxy-1,2,4-triazolo[3,4-a]phthalazine Sodium hydride (27 mg, 0.67 mmol) was added to a stirred solution of Intermediate 2 (150 mg, 0.561 mmol) in DMF (20 ml) at room temperature under nitrogen. The mixture was heated at 80° C. for 0.3 h, cooled to room temperature and a solution of 3-chloromethylpyridazine (143 mg, 1.12 mmol) in DMF (2 ml) added. The reaction mixture was stirred at room temperature for 0.5 h and at 80° C. for 4 h. After cooling to room temperature, water (100 ml) was added and the resulting precipitate filtered off, dissolved in dichloromethane, washed with water (×3), dried ($MgSO_4$) and evaporated in vacuo. Flash chromatography of the residue on silica gel, eluting with 3% methanol/dichloromethane, followed by recrystallisation (dichloromethane/ethyl acetate) gave the title-product (78 mg, 41%) mp 222–224° C.; $^1$H NMR (360 MHz, $CDCl_3$) δ 2.60 (3H, d, J=0.7 Hz, Me), 6.00 (2H, s, $CH_2$), 6.83 (1H, s, Ar—H), 7.57 (1H, dd, J=8.4 and 5.0 Hz, Ar—H), 7.83 (1H, m, Ar—H), 7.97 (1H, m, Ar—H), 8.18 (1H, dd, J=8.4 and 1.6 Hz, Ar—H), 8.30 (1H, d, J=7.8 Hz, Ar—H), 8.68 (1H, d, J=7.8 Hz, Ar—H), 9.20 (1H, m, Ar—H); MS ($ES^+$) m/e 360 $[MH]^+$; Anal. Found. C, 60.31; H, 3.27; N, 27.15. $C_{18}H_{13}N_7O_2$ requires C, 60.16; H, 3.64; N, 27.28%.

EXAMPLE 16

3-(5-Methylisoxazol-3-yl)-6-(4-pyrimidinyl)methyloxy-1,2,4-triazolo[3,4-a]phthalazine The title-compound was prepared from Intermediate 2 and 4-chloromethylpyrimidine, prepared following the procedure given for Example 15 part a, using the procedure given for Example 15 part b, mp 222–224° C. $^1$H NMR (360 MHz, $CDCl_3$) δ 2.58 (3H, d, J=0.6 Hz, Me), 5.75 (2H, s, $CH_2$), 6.77 (1H, s, Ar—H), 7.77 (1H, d, J=4.5 Hz, Ar—H), 7.88 (1H, t, J=7.7 Hz, Ar—H), 7.99 (1H, t, J=7.4 Hz, Ar—H), 8.33 (1H, d, J=7.9 Hz, Ar—H), 8.70 (1H, d, J=7.7 Hz, Ar—H), 8.82 (1H, d, J=5.1 Hz, Ar—H), 9.26 (1H, s, Ar—H); MS ($ES^+$) m/e 360 $[MH]^+$; Anal. Found. C, 60.41; H, 3.41; N, 27.05. $C_{18}H_{13}N_7O_2$ requires C, 60.16; H, 3.64; N, 27.28%.

EXAMPLE 17

3-(5-Methylisoxazol-3-yl)-6-(pyrazin-2-yl)methyloxy-1,2,4-triazolo[3,4-a]phthalazine The title-compound was prepared from Intermediate 2 and 2-chloromethylpyrazine, prepared following the procedure of Example 15 part a, using the procedure given for Example 15 part b, $^1$H NMR (360 MHz, CDCl$_3$) δ 2.59 (3H, d, J=0.7 Hz, CH$_3$), 5.82 (2H, s, CH$_2$), 6.83 (1H, d, J=0.8 Hz, Ar—H), 7.83 (1H, t, J=8.1 Hz, Ar—H), 7.97 (1H, t, J=8.3 Hz, Ar—H), 8.30 (1H, d, J=7.8 Hz, Ar—H), 8.60 (2H, d, Ar—H), 8.70 (1H, d, Ar—H), 9.15 (1H, s, Ar—H); MS (ES$^+$) m/e 360 [MH]$^+$; Anal. Found. C, 60.29; H, 3.31; N, 27.09. C$_{18}$H$_{13}$N$_7$O$_2$ requires C, 60.16; H, 3.64; N, 27.28%.

EXAMPLE 18

3-(5-Methylisoxazol-3-yl)-6-(2-guinolinyl) methyloxy-1,2,4-triazolo[3,4-a]phthalazine The title-compound was prepared from Intermediate 2 and 2-chloromethylquinoline, prepared following the procedure of Example 15 part a, using the procedure given for Example 15 part b, mp 223–225° C.; $^1$H NMR (360 MHz, CDCl$_3$) δ 2.53 (3H, d, J=0.6 Hz, Me), 5.94 (2H, s, CH$_2$), 6.76 (1H, d, J=0.7 Hz, Ar—H), 7.58 (1H, t, J=7.1 Hz, Ar—H), 7.80–7.86 (4H, m, Ar—H), 7.87 (1H, m, Ar—H), 8.15 (1H, d, Ar—H), 8.25 (1H, d, J=8.5 Hz, Ar—H), 8.35 (1H, d, J=7.8 Hz, Ar—H), 8.70 (1H, d, Ar—H); MS (ES$^+$) m/e 409 [MH]$^+$; Anal. Found. C, 67.70; H, 3.54; N, 20.35. C$_{23}$H$_{16}$N$_6$O$_2$ requires C, 67.64; H, 3.94; N, 20.57%.

EXAMPLE 19

3-(5-Methylisoxazol-3-yl)-6-(2-quinolilyl) methyloxy-1,2,4-triazolo[3,4-a]phthalazine The title-compound was prepared from Intermediate 2 and 2-chloromethylquinoxaline, prepared following the procedure of Example 15 part a, using the procedure given for Example 15 part b, mp 243–245° C.; $^1$H NMR (360 MHz, CDCl$_3$) δ 2.58 (3H, s, Me), 6.00 (2H, s, CH$_2$), 6.82 (1H, s, Ar—H), 7.80–7.85 (3H, m, Ar—H), 7.97 (1H, t, Ar—H), 8.11–8.14 (2H, m, 2 of Ar—H), 8.32 (1H, d, J=7.8 Hz, Ar—H), 8.70 (1H, d, Ar—H), 9.39 (1H, s, Ar—H); MS (ES$^+$) m/e 410 [MH]$^+$; Anal. Found. C, 63.75; H, 3.31; N, 23.32. C$_{22}$H$_{15}$N$_7$O$_2$·0.1 (CH$_2$Cl$_2$) requires C, 63.52; H, 3.66; N, 23.46%.

DESCRIPTION 1

Rapid Analogue Synthesis of 6-(aryl)alkyloxy-3-(5-methylisoxazol-3-yl)-1,2,4-triazolo[3,4-a] phthalazines To 0.1 g of appropriate alcohol in each tube with a stirrer under dry nitrogen was added a solution of Intermediate 1 in dimethylformamide (1.5 ml, 33 mg/ml) followed by 0.35 ml of a 1 M solution of lithium bis(trimethylsilyl) amide in tetrahydrofuran. The reactions were stirred for 16 h, diluted with methanol/water (1:4) (15 ml) and poured onto separate C18 Mega Bond Elut® cartridges (20 ml, 5 g). The cartridges were eluted with a gradient of 50 to 100% methanol/water and the fractions containing product were evaporated to yield the title-compounds.

The following examples were prepared by the method of Description 1.

EXAMPLE 20

3-(5-Methylisoxazol-3-yl)-6-(2-(4-trifluoromethyl) pyridyloxy)ethyloxy-1,2,4-triazolo[3,4-a]phthalazine $^1$H NMR (250 MHz, CDCl$_3$) δ 2.59 (3H, s), 4.88–5.03 (4H, m)>6.86 (1H, s), 7.04 (1H, s), 7.13 (1H, d, J=5 Hz), 7.84 (1H, t, J=8 Hz), 7.98 (1H, t, J=8 Hz), 8.23 (1H, d, J=8 Hz), 8.32(1H, d, J=5 Hz), 8.70(1H, d, J=8 Hz); MS (ES$^+$) m/e 457 [MH]$^+$.

EXAMPLE 21

3-(5-Methylisoxazol-3-yl)-6-(6-methylpyrid-2-yl) propyloxy-1,2,4-triazolo[3,4-a]phthalazine $^1$H NMR (250 MHz, CDCl$_3$) δ 2.37–2.47 (2H, m), 2.54 (3H, s), 2.58 (3H, s), 3.07 (2H, t, J=8 Hz), 4.69 (2H, t, J=6 Hz), 6.85 (1H, s), 7.01 (2H, t, J=8 Hz), 7.50 (1H, t, J=7.5 Hz), 7.80 (1H, t, J=7 Hz), 7.96 (1H, t, J=8 Hz), 8.17 (1H, d, J=7.5 Hz), 8.68 (1H, d, J=7.5 Hz); MS (ES$^+$) m/e 401 [MH]$^+$.

EXAMPLE 22

3-(5-Methylisoxazol-3-yl)-6-(5-(4-methylisothiazolyl)ethyloxy-1,2,4-triazolo[3,4-a] phthalazine $^1$H NMR (360 MHz, CDCl$_3$) δ 2.51 (3H, s), 2.58 (3H, s), 3.46 (2H, t, J=6 HZ), 4.81 (2H, t, J=6 Hz), 6.83 (1H, s), 7.83 (1H, t, J=8 Hz), 7.96 (1H, t, J=7 Hz), 8.21 (1H, d, J=8 Hz), 8.62 (1H, s), 8.69 (1H, d, J=8 Hz); MS (ES$^+$) m/e 393 [MH]$^+$.

EXAMPLE 23

3-(5-Methylisoxazol-3-yl)-6-(2,6-dichrophenly) methyloxy-1,2,4-triazolophthalazine $^1$H NMR (250 MHz, CDCl$_3$), δ 2.60 (3H, s), 5.91 (2H, s), 6.91 (1H, s), 7.26–7.46 (3H, m), 7.77 (1H, t, J=7 Hz), 7.95 (1H, t, J=8 Hz), 8.15 (1H, d, J=8 Hz), 8.70 (1H, d, J,=8 Hz). MS (ES$^+$) m/e 426 [MH]$^+$.

EXAMPLE 24

3-(5-Methylisoxazol-3-yl)-6-(4-methylthiazol-5-yl ethyloxy-1,2,4-triazolo-[3,4-a]phthalazine $^1$H NMR (250 MHz, CDCl$_3$), δ 2.51 (3H, s), 2.58 (3H, s), 3.47 (2H, t, J=6 Hz), 4.81 (2H, t, J=6 Hz), 6.84 (1H, s), 7.84 (1H, t, J=7 Hz), 7.97 (1H, t, J=7 Hz), 8.21 (1H, d J=8 Hz), 8.64 (1H, s), 8.70 (1H, d, J=8 Hz); MS (ES$^+$) m/e 393 [MH]$^+$.

EXAMPLE 25

3-(5-Methylisoxazol-3-yl-6-(2-methylthiazol-4-yl) ethyloxy-1,2,4-triazolo-[3,4-a]phthalazine $^1$H NMR (250 MHz, CDCl$_3$) δ 2.59 (3H, s), 2.71 (3H, s), 3.42 (2H, t, J=6 Hz), 4.93 (2H, t, J=6 Hz), 6.88 (1H, s), 7.00 (1H, s), 7.79 (1H, t, J=7 Hz), 7.94 (1H, t, J=7 Hz), 8.16 (1H, d, J=7 Hz), 8.67 (1H, d, J=7 Hz); MS (ES$^+$) m/e 393 [MH]$^+$.

EXAMPLE 26

3-(5-Methylisoxazol-3-yl)-6-(2-[1-(3-trifluoromethyl)pyrid-6-yl]imidazolyl) methyloxy-1,2,4-triazolo[3,4-a]phthalazine MS (ES$^+$) m/e 493 [MH]$^+$.

EXAMPLE 27

3-(5-Methylisoxazol-3-yl)-6-[(1-benzyl)imidazol-2-yl]methyloxy-1,2,4-triazolo[3,4-a]phthalazine $^1$H NMR (250 MHz), CDCl$_3$) δ 2.57 (3H, s), 5.39 (2H, s), 5.76 (2H, s), 6.87–7.19 (8H, m), 7.64 (1H, t, J=8 Hz), 7.78

(1H, d, J=8 Hz), 7.89 (1H, t, J=7 Hz), 8.62 (1H, d, J=7 Hz); MS (ES$^+$) m/e 438 [MH]$^+$.

EXAMPLE 28

3-(5-Methylisoxazol-3-yl)-6-[1-(4chlorophenyl)-1,2,3-triazol-4-yl]methyloxy-1,2,4-triazolo[3,4-a]phthalazine $^1$H NMR (250 MHz, CDCl$_3$) δ 2.64 (3H, s), 5.83 (2H, s), 6.92 (1H, s), 7.46 (2H, d, J=9 Hz), 7.79–7.85 (3H, m), 7.96 (1H, t, J=8 Hz), 8.29 (1H, d, 7 Hz), 8.66 (1H, d, J=7 Hz), 9.72 (1H, s); MS (ES$^+$) m/e 459 [MH]$^+$.

EXAMPLE 29

3-(5-Methylisoxazol-3-yl)-6-(3-chloro-2-methyl-5-trifluoromethylpyrazol-4-yl)methyloxy-1,2,4-triazolo[3,4-a]phthalazine $^1$H NMR (250 MHz, CDCl$_3$) δ 2.59 (3H, s), 3.97 (3H, s), 5.58 (2H, s), 6.86 (1H, s), 7.79 (1H, t, J=8 Hz), 7.96 (1H, t, J=7 Hz), 8.14 (1H, d, J=8 Hz), 8.70 (1H, d, J=7 Hz); MS (ES$^+$) m/e 464 [MH]$^+$.

EXAMPLE 30

3-(5-Isopropylisoxazol-3-yl)-6-(2-pyridyl)methyloxy-1,2,4-triazolo[3,4-a]phthalazine a) Ethyl 2,4-dioxo-5-methylhexanoate Sodium (2.63 g, 0.116 mol) was added in small portions to ethanol (65 ml) under nitrogen and the mixture heated until at reflux to aid dissolution. The solution was cooled to 0° C. and diethyl oxalate (16.98 g, 0.116 mol) and 3-methyl-2-butanone (10.0 g, 0.116 mol) added. The resulting solid was allowed to stand at room temperature for 1 h and then heated at 80° C. for 0.75 h. The solid mass was cooled to room temperature, acidified to pH 2 using dilute sulphuric acid, and water added. The mixture was extracted with ether (×2) band the combined ethereal extracts dried (MgSO$_4$), evaporated in vacuo and the residue distilled under reduced pressure to give the title-ester (14.4 g, 67%); $^1$H NMR (360 MHz, CDCl$_3$) δ 1.19 (6H, d, J=6.8 Hz, 2 of Me), 1.38 (3H, t, J=7.1 Hz, Me), 2.67 (1H, septet, J=7.0 Hz, CHMe$_2$), 4.36 (2H, q, J=7.1 Hz, CH$_2$), 6.41 (1H, s, CH), 14.53 (1H, br s, OH) (enol form).

b) Ethyl 5-isopropylisoxazole-3-carboxylate

A mixture of the preceding ester (5.0 g, 27 mmol) and hydroxylamine hydrochloride (5.6 g, 81 mmol) in ethanol (100 ml) was heated at reflux under nitrogen for 1 h. The mixture was cooled to room temperature, the solvent evaporated in vacuo and the residue partitioned between ethyl acetate and water. The aqueous layer was separated and extracted further with ethyl acetate (×1). The combined extracts were dried (MgSO$_4$), evaporated in vacuo and the residue chromatographed on silica gel, eluting with 40% ethyl acetate/hexane, to give the title-product (3.60 g, 73%); $^1$H NMR (360 MHz, CDCl$_3$) 1.34 (6H, d, J=6.9 Hz, 2 of Me), 1.41 (3H, t, J=7.1 Hz, Me), 3.13 (1H, septet, J=7.1 Hz, CHMe$_2$), 4.43 (2H, q, J=7.1 Hz, CH$_2$), 6.39 (1H, d, J=0.8 Hz, Ar—H).

c) 5-Isopropylisoxazole-3-carboxylic acid

A solution of sodium hydroxide (1.76 g, 44.0 mmol) in water (5 ml) was added to a stirred solution of the preceding product (2.00 g, 10.9 mmol) in methanol (10 ml). After 3 h at room temperature, the methanol was evaporated in vacuo and the aqueous solution cooled and acidified to pH 2 with 2N hydrochloric acid. The solution was extracted with dichloromethane (×2) and the combined extracts dried (MgSO$_4$) and evaporated in vacuo to give the title-acid (1.39 g, 82%), $^1$H NMR (250 MHz, CDCl$_3$) δ 1.36 (6H, d, J=6.9 Hz, 2 of Me), 3.16 (1H, septet, J=7.0 Hz, CHMe$_2$), 6.47 (1H, d, J=0.5 Hz, Ar—H).

d) 3-(5-Isopropylisoxazol-3-yl)-6-(2-pyridyl methyloxy-1,2,4-triazolo[3,4-a]phthalazine The title-compound was prepared from the preceding acid, 1-chloro-4-hydrazinophthalazine and 2-pyridylcarbinol, using the procedures given for Intermediate 1 part c and Example 1, $^1$H NMR (360 MHz, CDCl$_3$) δ 1.42 (6H, d, J=7.0 Hz, 2 of Me), 3.23 (1H, septet, J=7.0 Hz, CHMe2), 5.78 (2H, s, CH$_2$O), 6.82 (1H, d, J=0.7 Hz, Ar—H), 7.29 (1H, m, Ar—H), 7.74–7.85 (3H, m, 3 of Ar—H), 7.96 (1H, m, Ar—H), 8.32 (1H, d, J=7.8 Hz, Ar—H), 8.65–8.74 (2H, m, Ar—H); MS (ES$^+$) m/e 387 [MH]$^+$; Anal. Found. C, 65.08. H, 4.46; N, 21.91. C$_{21}$H$_{18}$N$_6$O$_2$ requires C, 65.27; H, 4.69; N, 21.75%.

EXAMPLE 31

3-(5-Cyclopropylisoxazol-3-yl)-6-(2-pyridyl)methyloxy-1,2,4-triazolo[3,4-a]phthalazine The title-compound was prepared as described in Example 30 with cyclopropylmethyl ketone being used instead of 3-methyl-2-butanone in step a), $^1$H NMR (360 MHz, CDCl$_3$) δ 1.09–1.20 (4H, m, 2 of CH$_2$), 2.19 (1H, m, CH), 5.77 (2H, s, CH$_2$O), 6.75 (1H, s, Ar—H), 7.29 (1H, m, Ar—H), 7.74–7.84 (3H, m, 3 of Ar—H), 7.96 (1H, m, Ar—H), 8.32 (1H, d, J=8.5 Hz. Ar—H), 8.68–8.72 (2H, m, Ar—H); MS (ES$^+$) m/e 385 [MH]$^+$; Anal. Found C, 65.43; H, 3.89; N, 21.75. C$_{21}$H$_{16}$N$_6$O$_2$ requires C, 65.62; H, 4.19; N, 21.86%.

EXAMPLE 32

3-(5-Ethylisoxazol-3-yl)-6-(2-pyridyl)methyloxy-1,2,4-triazolo[3,4-a]phthalazine a) 6-Chloro-3-(5-ethylisoxazol-3-yl)-1,2,4-triazolo[3,4-a]phthalazine and 6-chloro-3-(4,5-dimethylisoxazol-3-yl)-1,2,4-triazolo[3,4-a]phthalazine The title compounds were prepared as described in Example 30 with 2-butanone being used instead of 3-methyl-2-butanone in step a). Separation of the title compounds was achieved by chromatography on alumina eluting with dichloromethane/hexane (9:1).

6-chloro-3-(5-ethylisoxazol-3-yl)-1,2,4-triazolo[3,4-a]phtlhalazine: $^1$H NMR (250 MHz, CDCl$_3$) δ 1.42 (3H, t, J=7.6 Hz, Me), 2.98 (2H, q. J=7.6 Hz, CH$_2$), 6.89 (1H, s, Ar—H), 7.95 (1H, m, Ar—H), 8.07 (1H, m, Ar—H), 8.34 (1H, dd, J=8.2 and 0.6 Hz, Ar—H), 8.78 (1H, m, Ar—H); MS (ES$^+$) m/e 300 [MH]$^+$.

6-chloro-3-(4,5-dimethylisoxazol-3-yl)-1,2,4-triazolo[3,4-a]phthalazine: $^1$H NMR (250 MHz, CDCl$_3$) δ 2.33 (3H, d, J=0.5 Hz, Me), 2.49 (3H, d, J=0.4 Hz, Me), 7.95 (1H, m, Ar—H), 8.07 (1H, m, Ar—H), 8.34 (1H, d, J=7.6 Hz, Ar—H), 8.78 (1H, m, Ar—H); MS (ES$^+$) m/e 300 [MH]$^+$.

b) 3-(5-Ethylisoxazol-3-yl)-6-(2-pyridyl)methyloxy-1,2,4-triazolo[3,4-a]phthalazine The title-compound was prepared from 6-chloro-3-(5-ethylisoxazol-3-yl)-1,2,4-triazolo[3,4-a]phthalazine and 2-pyridylcarbinol using the procedure given for Example 1, $^1$H NMR (360 MHz, CDCl$_3$) δ 1.42 (3H, t, J=7.6 Hz, Me), 2.93 (2H, q, J=7.5 Hz, CH$_2$), 5.78 (2H, s, CH$_2$O), 6.83 (1H, s, Ar—H), 7.29 (1H, m, Ar—H), 7.75–7.85 (3H, m, 3 of Ar—H), 7.99 (1H, m, Ar—H), 8.33 (1H, d, J=7.8 Hz, Ar—H), 8.64–8.72 (2H, m, Ar—H); MS (ES$^+$) m/e 373 [MH]$^+$.

EXAMPLE 33

3-(4,5-Dimethylisoxazol-3-yl)-6-(2-pyridyl)methyloxy-1,2,4-triazolo[3,4-a]phthalazine The title-compound was prepared from 6-chloro-3-(4,5-dimethylisoxazol-3-yl)-1,2,4-triazolo[3,4-a]phthalazine prepared in Example 32 part a and 2-pyridylcarbinol using the procedure given for Example 1, $^1$H NMR (360 MHz, CDCl$_3$) δ 2.30 (3H, s, Me), 2.49 (3H, s, Me), 5.73 (2H, s, CH$_2$O), 7.29 (1H, m, Ar—H), 7.70–7.83 (3H, m, 3 of Ar—H), 7.96 (1H, m, Ar—H), 8.31 (1H, d, J=8.3 Hz, Ar—H, 8.64–8.70 (2H, m, 2 of Ar—H); MS (ES$^+$) m/e 373 [MH]$^+$; Anal. Found C, 64.38; H, 4.05; N,22.60. C$_{20}$H$_{16}$N$_6$O$_2$ requires C, 64.50; H, 4.33; N, 22.57%.

EXAMPLE 34

3-(3-Isoxazolyl)-6-(2-pyridyl)methyloxy-1,2,4-triazolo[3,4-a]phthalazine a) Ethyl isoxazole-3-carboxylate A solution of triethylamine (5.5 ml, 40 mmol) in diethyl ether (35 ml) was added over 0.3 h to a vigorously stirred solution of carbethoxychloraldoxime (5.00 g, 33.0 mmol) (prepared as described in J. Org. Chem., 1983, 48, 366) and vinyl acetate (30.5 ml, 33.1 mmol) in ether (65 ml) at reflux under nitrogen. The mixture was heated at reflux for a further 1 h and then allowed to cool to room temperature. Water (50 ml) was added and the ethereal layer separated, dried (MgSO$_4$) and evaporated in vacuo to give ethyl (5acetoxy-Δ$^2$-isoxazlin-3-yl)carboxylate (6.28 g, 95%). This material was heated at 180° C. under nitrogen for 1 h and then distilled under reduced pressure to give the title-ester (3.23 g, 73%) bp 62° C./1 mm Hg; $^1$H NMR (250 MHz, CDCl$_3$) δ 1.43 (3H, t, J=7.2 Hz, CH$_3$), 4.47 (2H, q, J=7.1 Hz, CH$_2$), 6.80 (1H, d, J=1.7 Hz, Ar—H), 8.62 (1H, d, J=1.7 Hz, Ar—H).

b) 6-Chloro-3-(3-isoxazolyl)-1,2,4-triazolo[3,4-a]phthalazine

Lithium hydroxide monohydrate (0.327 g, 7.79 mmol) was added to a stirred solution of the preceding ester (1.00 g, 7.09 mmol) in THF/H$_2$O (1:1) (6 ml) at 0° C. After 2 h at 0° C., the solvent was evaporated in vacuo and the residue dissolved in water and acidified to pH 1 with 2N hydrochloric acid. Ethanol was added, the solvents evaporated in vacuo and the residue azeotroped with ethanol and dried in vacuo to give isoxazole-3-carboxylic acid contaminated with lithium chloride.

The title-compound was prepared from this material reacting with 1-chloro-4-hydrazinophthalazine using the procedure described for Intermediate 1, step c, $^1$H NMR (250 MHz, CDCl$_3$) δ 7.30 (1H, d, J=1.1 Hz, Ar—H), 7.96 (1H, m, Ar—H), 8.09 (1H, m, Ar—H), 8:36 (1H, d, Ar—H), 8.68 (1H, s, Ar—H), 8.80 (1H, d, Ar—H); MS (ES$^+$) m/e 272 [MH]$^+$.

c) 3-(3-Isoxazolyl)-6-(2-pyridyl)methyloxy-1,2,4-triazolo[3,4-a]phthalazine

The title-compound was prepared from the preceding product and 2-pyridylcarbinol using the procedure given for Example 1, $^1$H NMR (360 MHz, CDCl$_3$) δ 5.78 (2H, s, CH$_2$), 7.24 (1H, d, J=1.6 Hz, Ar—H), 7.30 (1H, m, Ar—H), 7.72–7.88 (3H, m, 3 of Ar—H), 7.97 (1H, m, Ar—H), 8.33 (1H, d, J=7.9 Hz, Ar—H), 8.60–8.72 (3H, m, 3 of Ar—H); MS (ES$^+$) m/e 345 [MH]$^+$.

EXAMPLE 35

3-[5-(Pyridin-3-yl)isoxazol-3-yl]-6-(2-pyridinyl)methyloxy-1,2,4-triazolo[3,4-a]phthalazine a) Ethyl 5-(tri-n-butylstannyl)isoxazole-3-carboxylate A solution of triethylamine (2.68 g, 26.5 mmol) in diethyl ether (40 ml) was added over 5 h to a vigorous stirred solution of carbethoxychloraldoxime (4.01 g, 26.5 mmol) and tri-n-butylethynyltin (10.0 g, 31.7 mmol) in diethyl ether (64 ml) at room temperature under nitrogen. The mixture was stirred overnight at room temperature, then diluted with ether, washed with water (×2), dried (MgSO$_4$) and evaporated in vacuo. Flash chromatography of the residue on silica gel, eluting with 8% methanol/dichloromethane, gave the title-ester (6.75 g, 59%), $^1$H NMR (250 MHz, CDCl$_3$) δ 0.89 (9H, t, J=7.0 Hz, 3 of CH$_3$), 1.06–1.72 (21H, m, CH$_3$ and 9 of CH$_2$), 4.45 (2H, q, J=7.1 Hz, CH$_2$O), 6.80 (1H, t, J=1.4 Ar—H); MS (ES$^+$) m/e 428 [MH]$^+$.

b) Ethyl 5-(pyridin-3-yl)isoxazole-3-carboxylate

A mixture of the preceding ester (3.50 g, 8.14 mmol), 3-bromopyridine (0.53 ml, 5.5 mmol) and Pd (PPh$_3$)$_2$Cl$_2$ (0.105 g) in dioxane (40 ml) was heated at reflux under nitrogen for 4 h. The solvent was evaporated in vacuo and the residue partitioned between dichloromethane and water. The aqueous layer was separated and extracted further with dichloromethane (×2). The combined extracts were dried (MgSO$_4$) and evaporated in vacuo, and the residue chromatographed on silica gel, eluting with 50% ethyl acetate/hexane, to give the required product (1.07 g, 60%), $^1$H NMR (250 MHz, CDCl$_3$) 1.46 (3H, t, J=7.2 Hz, CH$_3$), 4.49 (2H, q, J=7.2 Hz, CH$_2$), 7.05 (1H, s, Ar—H), 7.48 (1H, m, Ar—H), 8.14 (1H, m, Ar—H), 8.72 (1H, m, Ar—H), 9.07 (1H, d, J=1.6 Hz, Ar—H); MS (ES$^+$) m/e 219 [MH]$^+$.

c) 5-(Pyridin-3-yl)isoxazole-3-hydrazoic acid

Hydrazine monohydrate (0.56 ml, 11.5 mmol) was added to a stirred solution of the preceding ester (0.852 g, 3.90 mmol) in methanol (9 ml) at room temperature. After 2 h, the solvent was evaporated in vacuo and the residue azeotroped with ethanol to give the title-hydrazoic acid (0.804 g, 100%), $^1$H NMR (250 MHz, d$^6$-DMSO) δ 4.66 (2H, br s, NH$_2$), 7.51 (1H, s, Ar—H), 7.60 (1H, m, Ar—H), 8.32 (1H, m, Ar—H), 8.72 (1H, m, Ar—H), 9.15 (1H, m, Ar—H), 10.10 (1H, br s, NH); MS (ES$^+$) m/e 205 [MH]$^+$.

d) 6-Chloro-3-[5-(pyridin-3-yl)isoxazol-3-yl]-1,2,4-triazolo[3,4-a]phthalazine

A mixture of the preceding hydrazoic acid (798 mg, 3.91 mmol), 1,4-dichlorophthalazine (778 mg, 3.91 mmol) and triethylamine (0.54 ml, 3.9 mmol) in xylene (28 ml) was heated at reflux under nitrogen for 20.5 h. The mixture was cooled to room temperature, the solvent evaporated in vacuo and the residue partitioned between dichloromethane and water. The aqueous was separated and re-extracted with dichloromethane (×2). The combined extracts were dried (MgSO$_4$), evaporated in vacuo and the residue chromatographed on silica gel eluting with ethyl acetate, then 5% methanol/dichloromethane to afford the title-phthalazine (77 mg, 6%), $^1$H NMR (360 MHz, CDCl$_3$/d$^6$-DMSO) δ 7.51 (1H, m, Ar—H), 7.55 (1H, s, Ar—H), 7.99 (1H, m, Ar—H), 8.11 (1H, m, Ar—H), 8.24 (1H, m, Ar—H), 8.38 (1H, d, J=7.8 Hz, Ar—H), 8.78 (1H, m, Ar—H), 8.83 (1H, m, Ar—H), 9.18 (1H, br s, Ar—H); MS (ES$^+$) m/e 349 [MH]$^+$.

e) 3-[5-(Pyridin-3-yl)isoxazol-3-yl]-6-(2-pyridinyl)methyloxy-1,2,4-triazolo[3,4-a]phthalazine The title-compound was prepared from the preceding product and 2-pyridylcarbinol using the procedure given for Example 1, $^1$H NMR (360 MHz, CDCl$_3$) δ 5.83 (2H, s, CH$_2$), 7.29 (1H, m, Ar—H), 7.50 (1H, d, J=8.0 and 4.8 Hz, Ar—H), 7.57 (1H, s, Ar—H), 7.74–7.77 (2H, m, 2 of Ar—H), 7.87 (1H, m, Ar—H), 7.97 (1H, m, Ar—H), 8.26 (1H, m, Ar—H), 8.36 (1H, d, J=7.8 Hz, Ar—H), 8.62–8.76 (3H, m, 3 of Ar—H), 9.22 (1H, d, J 1.7 Hz, Ar—H); MS (ES$^+$) m/e 422 [MH]$^+$.

EXAMPLE 36

6-(2-Pyridyl)methyloxy-3-[5-(2-thienyl)isoxazol-3-yl]-1,2,4-triazolo[3,4-a]phthalazine The title-compound was prepared from ethyl 5-(2-thienyl)isoxazole-3-carboxylate (J. Org. Chem., 1961, 26, 1514)

using the procedure given for Example 1, mp 213–215° C.; $^1$H NMR (360 MHz, CDCl$_3$), δ 5.81 (2H, s, CH$_2$O), 7.20 (1H, m, Ar—H), 7.28–7.29 (2H, m, 2 of Ar—H), 7.52 (1H, m, Ar—H), 7.68 (1H, m, Ar—H), 7.75–7.77 (2H, m, 2 of Ar—H), 7.84 (1H, m, Ar—H), 7.95 (1H, m, Ar—H), 8.34 (1H, d, J=7.9 Hz, Ar—H), 8.65–8.72 (2H, m, 2 of Ar—H); MS (ES$^+$) m/e 427 [MH]$^+$. Anal. Found. C, 62.30; H, 3.07; N, 19.34. C$_{22}$H$_{14}$N$_6$O$_2$S requires C, 61.96; H, 3.31; N, 19.71%.

EXAMPLE 37

3-(5-Methylisoxazol-3-yl)-6-(1-methyl-1,2,4-triazol-3-yl)methyloxy-1,2,4-triazolo[3,4-a]phthalazine The title compound was prepared from Intermediate 1 and 1-methyl 1,2,4-triazole-3-methanol (prepared using the conditions of Itoh and Okongi, EP-A-421210) following the procedure given in Example 1, mp 249–251° C.; $^1$H NMR (360 MHz, CDCl$_3$), δ 2.59 (3H, d, J=0.7 Hz, Me), 3.97 (3H, s, Me), 5.71 (2H, s, CH$_2$), 6.98 (1H, d, J=0.7 Hz, Ar—H), 7.80 (1H, t, J=7.2 Hz, Ar—H), 7.94 (1H, t, J=8.2 Hz, Ar—H), 8.09 (1H, s, Ar—H), 8.26 (1H, d, J=7.7 Hz, Ar—H); 8.70 (1H, d, J 7.0 Hz, Ar—H); MS (ES$^+$) m/e 363 [MH]$^+$.

EXAMPLE 38

7,10-Difluoro-3-[5-methylisoxazol-3-yl)-6-(2-pyridyl)methyloxy-1,2,4-triazolo[3,4-a]phthalazine a) 5,8-Difluorophthalazine-1,4-dione 3,6-Difluorophthalic anhydride (10 g, 54 mmol) was added to a mixture of sodium acetate trihydrate (10 g, 73 mmol) and hydrazine hydrate (5 ml, 156 mmol) in 40% aqueous acetic acid. The reaction was heated under reflux conditions for 16 h and the reaction was filtered to give the title-compound as a white solid (10.5 g, 98%), $^1$H NMR (250 MHz, d$^6$-DMSO) δ 8.01 (2H, t, J=9 Hz), 11.50–11.80 (2H, br s).

b) 1.4-Dichloro-5,8-difluorophthalazine

The preceding dione (10.5 g, 18.9 mmol) was suspended in phosphorus oxychloride (200 ml) and then heated to reflux for 16 h. The solvent was removed by evaporation and the residue was treated with ice and basified with solid sodium hydrogen carbonate. The reaction was extracted with dichloromethane (3×100 ml), dried (MgSO$_4$), filtered and evaporated to yield the title-compound as a yellow solid (10.1 g) used without further purification in the next step.

c) 6-Chloro-7,10-difluoro-3-(5-methylisoxazol-3-yl)-1,2,4-triazolo[3,4-a]phthalazine The title compound was prepared from the preceding dichlorophthalazine according to the procedure given for Intermediate 1, $^1$H NMR (250 MHz, d$^6$-DMSO) δ 2.59 (3H, d, J=1 Hz), 7.00 (1H, d, J=1 Hz), 7.95 (1H, dt, J=9 and 4 Hz); MS (ES$^+$) m/e 322 [MH]$^+$.

d) 7,10-Difluoro-3-(5-methylisoxazol-3-yl)-6-(2-pyridyl)methyloxy-1,2,4-triazolo[3,4-a]phthalazine The title compound was prepared from the preceding chlorophthalazine and 2-pyridyl carbinol according to the procedure given for Example 1. $^1$H NMR (250 MHz, CDCl$_3$/CD$_3$OD 1:1) δ 2.63 (3H, d, J=1 Hz), 5.78 (2H, s), 6.92 (1H, d, J=1 Hz), 7.40–7.45 11E, m), 7.70 (1H, dt, J=9 and 4 Hz), 7.84–7.92 (3H, m) 8.94 (1H, d, J=5 Hz); MS (ES$^+$) m/e 395 [MH]$^+$.

INTERMEDIATE 3

6-Chloro-7-fluoro-3-(5-methylisoxazol-3-yl)-1,2,4-triazolo[3,4-a]phthalazine and 6-chloro-10-fluoro-3-(5-methylisoxazol-3-yl)-1,2,4-triazolo[3,4-a]phthalazine The title compounds were prepared from 3-fluorophthalic anhydride according to the procedure given for Example 38 part c. Intermediate 3 was separated into its constituent isomers by column chromatography on silica gel using dichloromethaneltoluene/ethyl acetate (2:2:1) to yield Intermediate 3(a) (less polar isomer): 6-chloro-7-fluoro-3-(5-methylisoxazol-3-yl)-1,2,4triazolo[3,4-a]phthalazine: $^1$H NMR (250 MHz, CDCl$_3$) δ 2.59 (3H, d, J=1 Hz), 6.90 (1H, d, J=1 Hz), 7.26 (1H, s), 7.80 (1H, t, J=9 Hz), 7.89–7.98 (1H, m), 8.19 (1H, d, J=9 Hz); MS (ES$^+$) m/e 304 [MH]$^+$ and Intermediate 3(b) (more polar isomer): 6-chloro-10-fluoro-3-(5-methylisoxazol-3-yl)-1,2,4-triazolo[3,4-a]phthalazine; $^1$H NMR (250 MHz, CDCl$_3$) δ 2.59 (3H, d, J=1 Hz), 6.89 (1H, d, J=1 Hz), 7.61 (1H, dd, J=13, 8 and 1 Hz), 8.03 (1H, dt, J=8 and 5 Hz), 8.67 (1H, d, J=13 Hz).

EXAMPLE 39

6,10-Bis[(2-pyridyl)methyloxy]-3-(5-methylisoxazol-3-yl)-1,2,4-triazolo[3,4-a]phthalazine Intermediate 3(b) (0.1 g, 0.33 mmol) was added to a mixture of 2-pyridylmethanol (0.1 g, 0.9 mmol) and lithium hexamethydisilazane (1 M in THF, 1 ml, 1 mmol) in DMF (5 ml) and stirred for 16 h. The reaction mixture was poured into water, extracted with dichloromethane, dried (MgSO$_4$), filtered and evaporated to yield an oil which was purified by chromatography on silica using 3% methanol/dichloromethane to yield the title-product as a pale yellow powder (47 mg, 30%); $^1$H NMR (250 MHz, CDCl$_3$) δ 2.59 (3H, s), 5.41 (2H, s), 5.78 (2H, s), 6.83 1H,.d, J=1 Hz), 7.18–7.38 (2H, m), 7.36 (1H, d, J=8 Hz), 7.49–7.68 (4H, m), 7.87 (1H, t, J=8 Hz), 8.36 (1H, d, J=8 Hz), 8.58–8.64 (2H, m); MS (ES$^+$) m/e 466 [MH]$^+$.

EXAMPLE 40

7-Fluoro-3-(5-methylisoxazol-3-yl)-6-(2-pyridyl)methyloxy-1,2,4-triazolo[3,4-a]phthalazine and 10-fluoro-3-(5-methylisoxazol-3-yl)-6-(2-pyridyl)methyloxy-1,2,4-triazolo[3,4-a]phthalazine The title compounds were prepared from Intermediate 3 and 2-pyridyl carbinol according to the procedure given for Example 1. The mixture was separated into its component isomers by column chromatography on silica to yield less polar isomer: 7-fluoro-3-(5-methylisoxazol-3-yl)-6-(2-pyridyl)methyloxy-1,2,4triazolo [3,4-a]phthalazine: $^1$H NMR (250 MHz, CDCl$_3$) δ 2.61 (3H, s), 5.78 (2H, s), 6.84 (1H, s), 7.26–7.31 (1H, m), 7.49–7.56 (1H, m), 7.79–7.81 (2H, m), 7.91–7.99 (1H, m), 8.54 (1H, d, J=8 Hz), 7.86–7.88 (1H, m); MS (ES$^+$) 377 [MH]$^+$ and the more polar isomer: 10-fluoro3-(5-methylisoxazol-3-yl)-6-(2-pyridyl)methyloxy-1,2,4triazolo[3,4-a]phthalazine; $^1$H NMR (250 MHz, CDCl$_3$) δ 2.59 (3H, s), 5.77 (2H, s), 6.83 (1H, s), 7.24–7.32 (1H, s), 7.63–7.85 (4H, m), 8.15 (1H, d, J=8 Hz), 8.64–8.66 (1H, m); MS (ES$^+$) 377 [MH]$^+$.

EXAMPLE 41

6-(1-Methylimidazol-4-yl)methyloxy-3-(5-methylisoxazol-3-yl)-1,2,4-triazolo[3,4-a]phthalazine The title-compound was prepared from Intermediate 1 and 1-methyl-4-hydroxymethylimidazole (J. Org. Chem., 1968, 33, 3758) using the procedure given for Example 1, mp 207.5–209° C.; $^1$H NMR (360 MHz, CDCl$_3$) δ 2.59 (3H, s, Me), 3.69 (3H, s, Me), 5.60 (2H, s, CH$_2$), 6.91 (1H, d, J=0.8 Hz, Ar—H), 7.43 (1H, s, Ar—H), 7.58 (1H, s, Ar—H), 7.76 (1H, td, J=7.7 and 1.1 Hz, Ar—H), 7.91 (1H, td, J=7.5 and 1.1 Hz, Ar—H), 8.26 (1H, d, J=8.0 Hz, Ar—H), 8.65 (1H, d, J=8.0 Hz, Ar—H); MS (ES$^+$) m/e 362 [MH]$^+$; Anal. Found. C, 59.73; H, 3.85; N, 27.48. $C_{18}15N_7O_2$ requires C, 59.83; H, 4.18; N, 27.13%.

EXAMPLE 42

6-(1-Methylimidazol-5-yl)methyloxy-3-(5-methylisoxazol-3-yl)-1,2,4-triazolo[3,4-a]phthalazine a) 5-(tert-Butyldimethylsilyloxymethyl)-1-methylimidazole To a solution of 4-(tert-butyldimethylsilyloxymethyl) imidazole (Amino, Y.; Eto, H; Eguchi, C. Chem. Pharm. Bull. 1989, 37, 1481–1487) (3.158 g, 14.9 mmol) in anhydrous THF (25 ml), cooled to −78° C. under nitrogen, was added a 1.6M solution of butyl-lithium in hexanes (10.2 ml, 16.4 mmol). The mixture was stirred under nitrogen at −78° C. for 30 min, then iodomethane (0.97 ml, 15.6 mmol) was added. The mixture was allowed to warm to room temperature and stirred for 5 h. Water (150 ml) was added and the mixture extracted with diethyl ether (150 ml). The organic extract was washed with brine, dried (MgSO$_4$) and evaporated in vacuo. The product isomers were separated by flash chromatography on alumina, eluting with 40% ethyl acetate/hexane to yield the title-imidazole (1.463 g, 43%), $^1$H NMR (250 MHz, CDCl$_3$), δ 0.05 (6H, s), 0.88 (9H, s), 3.67 (3H, m), 4.65 (2H, s), 6.90 (1H, s), 7.41 (1H, s).

b) 5-Hydroxymethyl-1-methylimidazole

To a solution of 5-tert-butyldimethylsilyloxymethyl-1-methyl imidazole (from step a) (0.100 g, 0.442 mmol) in ethanol (0.5 ml) and methanol (1 ml) was added 4M aqueous NaOH (0.165 ml, 0.66 mmol) and the mixture heated at 50° C. for 16 hrs. The mixture was evaporated in vacuo and the residue was purified by flash chromatography on silica gel eluting with dichloromethane/methanol/ammonia (aq), (80:20:2) to give (31.3 mg, 63%) of the title-alcohol, $^1$H NMR (250 MHz, CDCl$_3$) δ 3.71 (3H, s), 4.62 (2H, s), 6.87 (1H, s), 7.38 (1H, s).

c) 6-(1-methylimidazol-5-yl)methyloxy-3-(5-methylisoxazol-3-yl)-1,2,4-triazolo[3,4-a]phthalazine The title compound was prepared from the preceding alcohol and Intermediate 1 using the procedure given for Example 1, mp 236.5–237.5° C.; $^1$H NMR (360 MHz, CDCl$_3$) δ 2.59 (3H, d, J=0.7 Hz; CH$_3$), 3.77 (3H, s, CH$_3$), 5.69 (2H, s, CH$_2$), 6.86 (1H, d, J=0.8 Hz, Ar—H), 7.38 (1H, s, Ar—H), 7.55 (1H, s, Ar—H), 7.80 (1H, m, Ar—H), 7.96 (1H, m, Ar—H), 8.15 (1H, d, J=7.8 Hz; Ar—H), 8.80 (1H, d, Ar—H); MS (ES$^+$) m/e 362 [MH]$^+$; Anal. Found. C, 59.67; H, 3.84; N, 26.97. $C_{18}H_{15}N_7O_2$ required C, 59.83; H, 4.18; N, 27.13%.

EXAMPLE 43

3-(5-Methylisoxazol-3-yl-6-(2-methyl-1,2,4-triazol-3-yl methyloxy-1,2,4-triazolo[3,4-a]phthalazine The title-compound was prepared from Intermediate 1 and 1-methyl-1,2,4-triazole-5-methanol (prepared using the conditions of Itoh and Okongi, EP-A-421210) following the procedure given in Example 10, mp 256–258° C.; $^1$H NMR (360 MHz, CDCl$_3$) δ 2.57 (3H, s, CH$_3$), 4.11 (3H, s, CH$_3$), 5.83 (2H, s, CH$_2$), 6.85 (1H, s, Ar—H), 7.84 (1H, t, J=7.3 Hz, Ar—H) 7.92 (1H, s, Ar—H), 7.97 (1H, t, J=7.1 Hz, Ar—H), 8.24 (1H, d, J=8.1 Hz, Ar—H), 8.70 (1H, d, J=7.3 Hz, Ar—H). MS (ES$^+$) m/e 363 [MH]$^+$; Anal. Found. C, 56.30; H, 3.49; N, 30.53. $C_{17}H_{14}N_8O_2$ C, 56.35; H, 3.89; N, 30.92%.

EXAMPLE 44

3-(5-Methylisoxazol-3-yl)-6-(4-methyl-1,2,4-triazol-3-yl)methyloxy-1,2,4-triazolo[3,4-a]phthalazine The title-compound was prepared from Intermediate 1 and 4-methyl-1,2,4-triazole-3-methanol (prepared using the conditions of Itoh and Okongi, EP-A-421210) following the procedure given in Example 10, mp 261–263° C.; $^1$H NMR (360 MH$_2$, CDCl$_3$) δ 2.58 (3H, s, Me), 3.90 (3H, s, Me), 5.90 (2H, s, CH$_2$), 6.90 (1H, s, Ar—H), 7.82 (iH, m, Ar—H), 7.98 (1H, m, Ar—H), 8.14 (1H, s Ar—H), 8.20 (1H, s, Ar—H), 8.70 (1H, d, J=7.4 Hz, Ar—H); MS (ES$^+$) m/e 363 [MH]$^+$; Anal. Found. C, 50.22; H, 4.23; N, 15 27.45. $C_{17}H_{14}N_8O_2$ requires 50.68; H, 4.62; N, 27.81%.

EXAMPLE 45

3-(5-Methylisoxazol-3-yl)-6-[2-{[2-(trimethylsilyl)ethoxy]methyl}-1,2,4-triazolyl]methyloxy-1,2,4-triazolo[3, a]phthalazine a) 1-[2-(Trimethylsilyl)ethoxy]methyl-1,2,4-triazole To a suspension of sodium hydride (4.63 g, 0.12 mol) in tetrahydrofuran (150 ml) was added 1,2,4-triazole (8.0 g, 0.12 mol) at room temperature under nitrogen. The mixture was cooled to 0° C. and 2-(trimethylsilyl)ethoxymethylchloride (20.5 ml, 0.12 mol) added dropwise. The mixture was stirred at room temperature overnight, water (100 ml) was added and the mixture diluted with ethyl acetate. The organic layer was dried ((MgSO$_4$) and evaporated in vacuo and the residue distilled to give the title-compound (14.6 g, 63%), bp 110° C. at 5mm Hg; $^1$H NMR (250 MHz, CDCl$_3$) δ 0.01–0.03 (9H, s, 3 of CH$_3$), 0.93 (2H, m, CH$_2$), 3.63 (2H, m, CH$_2$), 5.52 (2H, s, CH$_2$), 7.99 (1H, s, Ar—H), 8.26 (1H, s Ar—H).

b) 2-[2-(Trimethylsilyl)ethoxymethyl]-1,2,4-triazole-3-carboxaldehyde

To a solution of the preceding triazole (10.0 g, 0.05 mol) in tetrahydrofuran (160 ml) was added n-butyl lithium (36.1 ml, 0.06 mol of a 1.6M solution in hexane) at −78° C. under nitrogen. The mixture was stirred for 0.25 h and N,N-dimethylformamide (3.88 ml, 0.05 mol) added. The mixture was left to warm to 0° C. over 2 h. Saturated ammonium chloride solution was added (25 ml) and the mixture extracted with ethyl acetate (3×100 ml), dried (Na2SO$_4$) and evaporated in vacuo. The residue was flash chromatographed on silica gel, eluting with 35% ethyl acetate/hexane, to give the title-product (7.70 g, 68%), $^1$H NMR (250 MHz, CDCl$_3$) δ 0.02–0.03 (9H, s, 3 of CH$_3$), 0.95 (2H, m, CH$_2$), 3.68 (2H, m CH$_2$), 5.89 (2H, s, CH$_2$), 8.12 (1H, s, Ar—H), 10.07 (1H, s, CHO).

c) 3-(Hydroxymethyl)-2-{[2-(trimethylsilyl)ethoxy]methyl}-1,2,4triazole

To a solution of the preceding aldehyde (7.70 g, 0.034 mol) in methanol (120 ml) at room temperature under nitrogen was added sodium borohydride (1.2 g, 0.034 mol) portionwise. After 1 h, the mixture was diluted with dichloromethane (150 ml) and washed with water (3×), dried (MgSO$_4$) and evaporated in vacuo. The residue was flash chromatographed on silica gel, eluting with 70% ethyl acetate/hexane, to give the title-product (4.0 g, 52%), $^1$H NMR (360 MHz. CDCl$_3$) δ 0.06–0.10 (9H, s, 3 of CH$_3$), 0.93 (2H, m, CH$_2$), 3.63 (2H, m, CH$_2$), 4.16 (1H, br s, OH), 4.87 (2H, br s, CH$_2$), 5.58 (2H, s, CH$_2$), 7.85 (1H, s, Ar—H).

d) 3-(5-Methylisoxazol-3-yl)-6-[2-{[2-(trimethylsilyl) ethoxy[methyl}-1,2,4-triazolyl]methyloxy-1,2,4triazolo[3,4-a]phthalazine The title-compound was prepared from Intermediate 1 and the preceding alcohol using the procedure given for Example 1, mp 153–155° C.; $^1$H NMR (360 MHz, CDCl$_3$) δ 0.04 (9H, s, 3 of CH$_3$), 0.89 (2H, t, J=8.2 Hz, CH$_2$), 2.61 (3H, s, me), 3.67 (2H, t, J=8.0 Hz, CH$_2$), 5.83 (2H, s, CH$_2$), 5.90 (2H, s, CH$_2$), 6.89 (1H, d, J=0.7 Hz, Ar—H), 7.85 (1H, t, J=7.2 Hz, Ar—H), 7.98 (1H, s, Ar—H), 8.01 (H, t, J=7.3 Hz, Ar—H), 8.33 (1H, d, J=8.0 Hz, Ar—H), 8.78 (1H, d, J=7.4 Hz, Ar—H); MS (ES$^+$) m/e 479 [MH]$^+$; Anal. Found. C, 55.38; H, 5.16; N, 23.26; C$_{22}$H$_{26}$N$_8$O$_3$Si requires C, 55.21; H, 5.48; N, 23.41%.

EXAMPLE 46

3-(5-Methylisoxazol-3-yl)-6-(1,2,4-triazol-3-yl) methyloxy-1,2,4-triazolo[3,4-a]phthalazine To a solution of 3-(5-methylisoxazol-3-yl)-6-[2-{[2-(trimethylsilyl)ethoxy]methyl}-1,2,4-triazolyl]methyloxy-1,2,4-triazolo-[3,4-a]phthalazine (1.20 g, 2.5 mmol) in ethanol (20 ml) was added 2N hydrochloric acid (40 ml) at room temperature. The mixture was heated at 60° C. for 5 h, saturated potassium carbonate solution wad added and the solvent evaporated in vacuo. The solid was triturated with ethanol, filtered and the filtrate evaporated in vacuo. The residue was flash chromatographed on silica gel, eluting with 4% methanol/dichloromethane, to give the title-product (140 mg, 16%), mp 260–262° C.; $^1$H NMR (360 MHz, d$^6$-DMSO) δ 2.56 (3H, s, me), 5.75 (2H, s, CH$_2$), 7.24 (1H, s, Ar—H), 8.00 (1H, t, J=8.1 Hz, Ar—H), 8.14 (1H, t, J=7.7 Hz, Ar—H), 8.26 (1H, d, J=8.0 Hz, Ar—H), 8.60 (1H, br s, NH), 8.65 (1H, d, J=7.4 Hz, Ar—H); MS (ES$^+$) m/e 349 [MH]$^+$.

EXAMPLE 47

3-(5-Methylisoxazol-3-yl)-6-(1-isopropyl-1,2,4-triazol-3-yl)methyloxy-1,2,4triazolo[3,4-a] phthalazine To a stirred solution of 3-(5-methylisoxazol-3-yl)-6-(1,2,4-triazol-3-yl)methyloxy.1,2,4-triazolo[3,4-a]phthalazine (100 mg, 0.29 mmol) in N,N-dimethylformamide (6 ml) at room temperature under nitrogen was added sodium hydride (17 mg, 0.41 mmol). The mixture was cooled to 0° C. and 2-iodopropane (0.04 ml, 0.36 mmol) added after 0.26 h. The mixture was left to stir at room temperature overnight, water was added and the precipitate filtered off. The crude product was flash chromatographed on silica gel, eluting with ethyl acetate→4% methanol/ethyl acetate, to give the title-product (25 mg, 22%), mp 179–181° C.; $^1$H NMR (360 MHz, CDCl$_3$) δ 1.58 (6H, d, J=6.7 Hz, 2 of CH$_3$), 2.59 (3H, s, CH$_3$), 4.58 (1H, septet, J=6.7 Hz, CH), 5.72 (2H, s, CH$_2$), 7.01 (1H, s, Ar—H), 7.78 (1H, t, J=7.2 Hz, Ar—H), 7.94 (1H, t, J=7.6 Hz, Ar—H), 8.13 (1H, s, Ar—H), 8.28 (1H, J=7.9 Hz, Ar—H), 8.80 (1H, d, J=7.4 Hz, Ar—H); MS (ES$^+$) m/e 391 [MH]$^+$; Anal. Found. C, 56.81; H, 4.68; N, 27.89; C$_{19}$H$_{18}$N$_8$O$_2$.0.7H$_2$O requires C, 56.62; H, 4.85; N, 27.80%.

EXAMPLE 48

3-(5-Methylisoxazol-3-yl)-6-(-1-ethyl-1,2,4-triazol-3-yl)methyloxy-1,2,4-triazolol3,4-a]phthalazine The title-compound was prepared from 3-(5-methylisoxazol-3-yl)-6-(1,2,4-triazol-3-yl)methyloxy-1,2,4-triazolo[3,4-a]phthalazine and iodoethane following the procedure given for Example 47, $^1$H NMR (360 MHz, CDCl$_3$) δ 1.56 (3H, t, J=7.3 Hz, Me), 2.59 (3H, s, Me), 4.26 (2H, q, J=7.3 Hz, CH$_2$), 5.72 (2H, s, CH$_2$), 7.00 (1H, s, Ar—H), 7.78 (1H, t, J=7.3 Hz, Ar—H), 7.94 (1H, t, J=7.7 Hz, Ar—H), 8.11 (1H, s, Ar—H), 8.29 (1H, d, J=8.1 Hz, Ar—H), 8.70 (1H, d, J=7.4 Hz, Ar—H); MS (ES$^+$) m/e 377 [MH]$^+$.

EXAMPLE 49

3-(5-Methylisoxazol-3-yl)-6-(1H-1,2,3-triazol-5-yl) methyloxy-1,2,4-triazolo[3,4-a]phthalazine a) 5-Formyl-1-[2-(trimethylsilyl)ethoxy]methyl-1,2,3-triazole n-Butyl lithium (6.8 ml of a 1.6M solution in hexanes, 10.9 mmol) was added dropwise over 0.08 h to a stirred solution of 1-[2-(trimethyl-silyl)ethoxy]methyl-1,2,3-triazole (J. Heterocycl. Chem., 1992, 29, 1203) (2.077 g, 10.42 mmol) in THF (30 ml) at −78° C. under nitrogen. The solution was allowed to warm to −60° C. over 0.67 h, then recooled to −78° C. and DMF (0.9 ml, 11.6 mmol) added. The mixture was allowed to warm to room temperature and stirred for 16.5 h. Saturated ammonium chloride solution (50 ml) was added and the reaction mixture extracted with diethyl ether (3×80 ml). The combined ethereal extrants were dried MgSO$_4$), evaporated in vacuo, and the residue chromatographed on silica gel, eluting with 30% ethyl acetate/hexane, to give the title-triazole (1.713 g, 72%), $^1$H NMR (360 MH$_2$, CDCl$_3$) δ 0.01 (9H, s, Me$_3$Si), 0.92–0.99 (2H, m, CH$_2$), 3.64–3.69 (2H, m, CH$_2$), 6.05 (2H, s, CH$_2$), 8.31 (1H, s, Ar—H), 10.12 (1H, s, CHO).

b) 5-Hydroxymethyl-1-[2-(trimethylsilyl)ethoxy]methyl-1,2,3-triazole

Sodium borohydride (0.284 g, 7.51 mmol) was added to a stirred solution of the preceding triazole (1.704 g, 7.495 mmol) in methanol (8 ml) at 0° C. under nitrogen. The mixture was stirred at 0° C. for 0.5 h and at room temperature for 0.5 h. Water was added and the mixture partitioned between dichloromethane and saturated brief. The aqueous layer was separated and further extracted with dichloromethane (×2). The combined organic layers were dried ((MgSO$_4$) and evaporated in vacuo and the residue chromatographed on silica gel, eluting with 70% ethyl acetate/hexane, to give the title-product (1.34 g, 78%), $^1$H NMR (360 MHz, CDCl$_3$) δ 0.00 (9H, s, Me$_3$Si), 0.90–0.95 (2H, m, CH$_2$), 3.58–3.63 (2H, m, CH$_2$), 4.84 (2H, s, CH$_2$), 5.80 (2H, s, CH$_2$), 7.68 (1H, s, Ar—H).

c) 3-(5-Methylisoxazol-3-yl)-6-{1-[2-(trimethylsilyl) ethoxy]methyl-1,2,3-triazol-5-yl}methylox-1,2,4-triazolo [3,4-a]phthalazine The title-compound was prepared from Intermediate 1 and the preceding alcohol following the procedure described for Example 10, 360 MHz (360 MHz, CDCl$_3$) δ 0.00 (9H, s, Me$_3$Si), 0.88–0.93 (2H, m, CH$_2$), 2.63 (3H, s, Me), 3.61–3.66 (2H, m, CH$_2$), 5.92 (2H, s, CH$_2$), 5.97 (2H, s, CH$_2$), 6.89 (1H, s, Ar—H), 7.86 (1H, m, Ar—H), 8.02 (1H, t, J=7.7 Hz, Ar—H), 8.18 (1H, s, Ar—H), 8.23 (1H, d, J=8.0 Hz, Ar—H), 8.76 (1H, d, J=8.0 Hz, Ar—H); MS (ES$^+$) m/e 479 [MH]$^+$.

d) 3-(5-Methylisoxazol-3-yl)-6-(1H-1,2,3-triazol-5-yl) methyloxy-1,2,4-triazolo[3,4-a]phthalazine A mixture of the preceding product, ethanol (10 ml) and 2N HCl (20 ml) was heated at 50° C. for 15.25 h. The solution was basified to pH 12 with saturated sodium carbonate solution and the solvents evaporated in vacuo. The residue was azeotroped with ethanol (×2) and chromatographed on silica gel, eluting with 0–4% methanol/dichloromethane (gradient elution), to give the title-product, ¹H NMR (400 MHz, CDCl₃) δ 2.65 (3H, s, Me), 5.73 (2H, s, CH₂), 7.02 (1H, s, Ar—H), 7.87 (1H, t, J=7.8 Hz, Ar—H), 7.99–8.03 (2H, m, 2 of Ar—H), 8.24 (1H, d, J=8.2 Hz, Ar—H) 8.72 (1H, d, J=7.9 Hz, Ar—H); MS (ES⁺) m/e 349 [MH]⁺.

EXAMPLE 50

3-(5-Methylisoxazol-3-yl)-6-(1-methyl-1,2,3-triazol-5-yl)methyloxy-1,2,4-triazolo[3,4-a]phthalazine, 3-(5-methylisoxazol-3-yl)-6-(2-methyl-1,2,3-triazol-4-yl)methyloxy-1,2,4-triazolo[3,4-a]phthalazine and 3-(5-methylisoxazol-3-yl)-6-(1-methyl-1,2,3-triazol-4-yl)methyloxy-1,2,4-triazolo[3,4-a]phthalazine Lithium hexamethyldisilazide (1.63 ml of a 1M solution in THF, 1.63 mmol) was added dropwise to a stirred solution of 3-(5-methylisoxazol-3-yl)-6-(1H-1,2,3-triazol-5-yl) methyloxy-1,2,4-triazolo[3,4-a]phthalazine (241 mg, 0.626 mmol) in DMF (50 ml) at −31° C. under nitrogen. The mixture was warmed to −23° C. over 1.5 h, methyl iodide (0.10 ml, 1.6 mmol) added dropwise and the reaction mixture allowed to warm to room temperature overnight. Water was added and the solvent evaporated in vacuo. The residue was partitioned between dichloromethane and water and the aqueous phase separated and re-extracted with dichloromethane (×1). The combined organic extrants were washed with brine (×1), dried (MgSO₄) and evaporated in vacuo. Chromatography of the residue on silica gel, eluting with 0–5% methanol/dicloromethane (gradient elution), followed by preparative HPLC (YMC Sil column, 250×20 mm) eluting with 5% methanol/1-chlorobutane, separated the triazole isomers:

Least polar isomer (HPLC solvent system): 3-(5-methylisoxazol-3-yl)-6-(2-methyl-1,2,3-triazol-4-yl)methyloxy-1,2,4-triazolo[3,4-a]phthalazine ¹H NMR (400 MHz, CDCl₃) δ 2.59 (3H, s, Me), 4.21 (3H, s, Me), 5.73 (2H, s, CH₂), 6.89 (1H, s, Ar—H), 7.79 (1H, m, Ar—H), 7.94 (1H, m, Ar—H), 8.10 (1H, s, Ar—H), 8.22 (1H, d, J=8.0 Hz, Ar—H), 8.67 (1H, d, J=8.0 Hz, Ar—H); MS (ES⁺) m/e 363 [MH]⁺.

Intermediate polarity isomer: 3-(5-methylisoxazol-3-yl)-6-(1-methyl-1,2,3-triazol-4-yl)methyloxy-1,2,4-triazolo[3,4-a]phthalazine ¹H NMR (400 MHz, CDCl₃) δ 2.60 (3H, s, Me), 4.09 (3H, s, Me), 5.78 (2H, s, CH₂), 6.90 (1H, d, J=0.8 Hz, Ar—H), 7.80 (1H, m, Ar—H), 7.94 (1H, m, Ar—H); 8.25 (1H, d, J=8.0 Hz, Ar—H), 8.65 (1H, d, J=8.0 Hz, Ar—H), 8.73 (1H, s, Ar—H); MS (ES⁺) m/e 363 [MH]⁺.

Most polar isomer (HPLC solvent system): 3-(5-methylisoxazol-3-yl)-6-(1-methyl-1,2,3-triazol-5-yl)methyloxy-1,2,4-triazolo[3,4-a]phthalazine ¹H NMR (400 MHz, CDCl₃) δ 2.56 (3H, s, Me), 4.19 (3H, s, Me), 5.76 (2H, s, CH₂), 6.82 (1H, s, Ar—H), 7.80 (1H, m, Ar—H), 7.96 (1H, m, Ar—H), 8.04 (1H, s, Ar—H), 8.12 (1H, d, J=8.8 Hz, Ar—H), 8.67 (1H, d, J=8.0 Hz, Ar—H); MS (ES⁺) m/e 363 [MH]⁺.

EXAMPLE 51

3-(5-Methylisoxazol-3-yl)-6-[(5-trifluoromethyl)pyridin-2-yl]methyloxy-1,2,4-triazolo[3,4a]phthalazine The title-compound was prepared from Intermediate 2 and 2-chloromethyl-5-trifluoromethylpyridine (prepared from 2-methyl-5-trifluoromethylpyridine (Chem. Pharm. Bull. 1990, 38(9) 2446–58) following the procedure given for Example 15 part a) using the procedure given for Example 15 part b, mp 236–238° C.; ¹H NMR (360 MHz, CDCl₃) δ 2.58 (3H, d, J=0.6 Hz, Me), 5.83 (2H, s, CH₂), 6.80 (1 h, d, J=0.7 Hz, Ar—H), 7.84 (1H, t, J=7.3 Hz, Ar—H), 8.00–8.03 (4H, m, Ar—H), 8.31 (1H, d, J=8.4 Hz, Ar—H), 8.70 (1H, d, J=8.0 Hz, Ar—H). MS (ES⁺) m/e 427 [H]+.

EXAMPLE 52

3-(5-Methylisoxazol-3-yl)-6-[(3-trifluoromethyl)pyridin-2-yl]methyloxy-1,2,4-triazolo[3,4-a]phthalazine The title-compound was prepared from Intermediate 2 and 2-chloromethyl-3-trifluoromethylpyridine (prepared from 2-methyl-3-trifluoromethylpyridine (Chem. Pharm. Bull. 1990, 38(9) 2446–58) following the procedure given for Example 15 part a) using the procedure given for Example 15 part b, mp 244–246° C.; ¹H NMR (360 MHz, CDCl₃) δ 2.56 (3H, d, J=1.1 Hz, Me), 5.94 (2H, s, CH₂), 6.79 (1H, d, J=1.2 Hz, Ar—H), 7.50 (1H, dd, J=11.3 Hz and 11.0 Hz, Ar—H), 7.80 (1H, t, J=10.4 Hz, Ar—H), 7.96 (1H, t, J=9.8 Hz, Ar—H), 8.01 (1H, d, J=11.4 Hz, Ar—H), 8.27 (1H, d, J=11.1 Hz, Ar—H), 8.75 (1H, d, J=9.4 Hz, Ar—H), 8.81 (1H, s, Ar—H); MS (ES⁺) m/e 427 [MH]⁺; Anal Found. C, 56.06; H, 2.80; N, 19.53. $C_{20}H_{13}N_6O_2F_3$ requires C, 56.34; H, 3.07; N, 19.71%.

EXAMPLE 53

3-(5-Methylisoxazol-3-yl-6-[(4-trifluoromethyl)pyridin-2-yl]methyloxy-1,2,4-triazolo[3,4-a]phthalazine The title-compound was prepared from Intermediate 2 and 2-chloromethyl-4-trifluoromethylpyridine (prepared from 2-methyl-4-trifluoromethylpyridine (Chem. Pharm. Bull. 1990, 38(9) 2446–58) following the procedure given for Example 15 part a) using the procedure given for Example 15 part b, mp 224–226° C.; ¹H NMR (360 MHz, CDCl₃) δ 2.59 (3H, d, J=0.8 Hz, CH₃), 5.84 (2H, s, CH₂), 6.82 (1H, d, J=0.8 Hz, Ar—H), 7.51 (1H, d, J=4.3 Hz, Ar—H), 7.83 (1H, t, J=8.3 Hz, Ar—H), 8.00 (1H, t, J=8.3 Hz, Ar—H), 8.12 (1H, s, Ar—H), 8.33 (1H, d, J=7.7 Hz, Ar—H), 8.70 (1H, d, J=8.0 Hz, Ar—H), 8.80 (1H, d, J=8.0 Hz, Ar—H). MS (ES⁺) m/e 427 [MH]⁺; Anal. Found, C, 56.42; H, 2.86; N, 19.47. $C_{20}H_{13}N_6O_2F_3$ requires C, 56.34; H, 3.07; N, 19.71%.

EXAMPLE 54

3-(5-Methylisoxazol-3-yl)-6-(thiazol-4-yl)-1,2,4-triazolo[3,4-a]phthalazine a) 4-Hydroxymethylthiazole A solution of in-chloroperbenzoic acid (57–58%, 61.1 g, 0.2 mol) in dichloromethane (500 ml) was added dropwise to a stirred solution of 4-methylthiazole (20 g, 0.2 mol) in dichloromethane (200 ml) at 0° C. When addition was complete the mixture was allowed to warm to room temperature and stirred for 18 h. The solvent was evaporated in vacuo to half its volume and the m-chlorobenzoic acid filtered off. This was repeated five times to give the crude N-oxide (31 g). The N-oxide (33 g) was added slowly to acetic anhydride (60 ml) at 110° C. with stirring. The mixture was heated at this temperature for 18 h, then cooled to room temperature and concentrated in vacuo. The residue was distilled in vacuo to give the crude acetate (9.58 g), bp 106–110° C. at 4 Torr. A solution of the acetate (9.58 g) in methanol/HCl solution (1:1) was stirred at room temperature for 4 h. The solvent was evaporated in vacuo and the residue partitioned between sodium hydroxide solution (4M) and dichloromethane. The aqueous phase was extracted into dichloromethane (6×) and the combined extracts were dried (MgSO$_4$) and evaporated in vacuo. Flash chromatography on silica gel, eluting with 3% methanol/dicloromethane, gave the title-alcohol (1.22 g, 23%), $^1$H NMR (250 MHz, CDCl$_3$) δ 4.85 (2H, s, CH$_2$), 7.27 (1H, m, Ar—H), 8.81 (1H, m, Ar—H); MS (ES$^+$) m/e 115 [MH]$^+$.

b) 3-(5-Methylisoxazol-3-yl)-6-(thiazol-4-yl)methyloxy-1,2,4-triazolo[3,4-a]phthalazine The title-compound was prepared from the preceding alcohol and Intermediate 1 using the procedure given for Example 10, mp 227–229° C.; $^1$H NMR (360 MHz, CDCl$_3$) δ 2.60 (3H, s, CH$_3$), 5.85 (2H, s, CH$_2$), 6.89 (1H, s, Ar—H), 7.80 (1H, m, Ar—H), 7.94 (1H, m, Ar—H), 8.13 (1H, d, J=2.0 Hz, Ar—H), 8.28 (1H, d, J=8.4 Hz, Ar—H), 8.60 (1H, d, J=2 Hz, Ar—H), 8.83 (1H, d, J=2.0 Hz, Ar—H); MS (ES$^+$) m/e 365 [MH]$^+$; Anal. Found. C, 55.67; H, 3.08; N, 22.47; C$_{17}$H$_{12}$N$_6$O$_2$S.0.25 H$_2$O requires C, 55.35; H, 3.42; N, 22.78%.

EXAMPLE 55

3-(Isothiazol-3-yl)methyloxy-3-(5-methylisoxazol-3-yl)-1,2,4-triazolo[3,4-a]phthalazine a) 3-Hydroxymethylisothiazole Lithium aluminum hydride (1M solution in tetrahydrofuran), (0.93 ml, 0.9 mmol) was added dropwise to a solution of ethyl isothiazole-3-carboxylate (J. Org. Chem., 1975, 40, 3381) (195 mg, 0.1 mmol) in tetrahydrofuran at −40° C. under N$_2$. The mixture was stirred at −40° C. for 45 min. Saturated sodium sulfate solution (1 ml) was added keeping the temperature below −30° C. The mixture was allowed to warm to room temperature, stirred for 1 h, then filtered and the filtrate evaporated in vacuo. The residue was purified by flash chromatographed on silica gel, using 30% ethyl acetate/hexane as eluant, to give the title-alcohol (47 mg, 33%); $^1$H NMR (250 MHz, CDCl$_3$) δ 4.86 (2H, s, CH$_2$), 7.22 (1H, d, J=4.7 Hz, Ar—H), 8.67 (1H, d, J=5 Hz, Ar—H); MS (ES$^+$) m/e 115 [MH]$^+$.

b) 6-(Isothiazol-3-yl)methyloxy-3-(5-methylisoxazol-3-yl)-1,2,4triazolo[3,4-a]phthalazine The title-compound was prepared from the preceding alcohol and Intermediate 1 using the procedure given for Example 1, mp 230–231° C.; $^1$H NMR (360 MHz, CDCl$_3$) δ 2.60 (3H, s, CH$_3$), 5.84 (2H, s, CH$_2$), 6.85 (1H, d, J=0.7 Hz, Ar—H), 7.68 (1H, d, J=4.6 Hz, Ar—H), 7.82 (1H, m, Ar—H), 7.96 (1H, m, Ar—H), 8.28 (1H, d, J=7.8 Hz, Ar—H), 8.70 (1H, d, J=8 Hz, Ar—H), 8.80 (1H, d, J=4 Hz, Ar—H); MS (ES$^+$) m/e 365 [MH]$^+$; Anal. Found. C, 56.11; H, 3.20; N, 22.59. C$_{17}$H$_{12}$N$_6$O$_2$S.0.1H$_2$O requires C, 55.76; H, 3.36; N, 22.95%.

EXAMPLE 56

3-(4-Methylisoxazol-3-yl)-6-[(4-tert-butyl)pyridazin-3-yl]methyloxy-1,2,4-triazolo[3,4-a]phthalazine The title-compound was prepared from Intermediate 2 and 3-chloromethyl-4-tert-butylpyridazine (prepared from 3-methyl-4-tert-butyl pyridazine (Acta Chemica, 1967, 21, 2104–2210) following the procedure given for Example 15 part a) using the procedure given for Example 15 part b, mp 230–232° C.; $^1$H NMR (360 MHz, CDCl$_3$) δ 1.51 (9H, s, 3 of CH$_3$), 2.57 (3H, s, CH$_3$), 6.18 (2H, s, CH$_2$), 6.87 (1H, d, J=0.7 Hz, Ar—H), 7.55 (1H, d, J=5.6 Hz, Ar—H), 7.74 (1H, t, J=1 Hz, Ar—H), 7.93 (1H, t, J=8.2 Hz, Ar—H), 8.18 (1H, d, J=7.6 Hz, Ar—H), 8.90 (1H, d, J37.4 Hz, Ar—H), 9.11 (1H, d, J=5.7 Hz, Ar—H); MS (ES$^+$) m/e 416 [MH]$^+$; Anal. Found. C, 60.75; H, 4.91; N, 22.19; C$_{22}$H$_{21}$N$_7$O$_2$0.4H$_2$O.0.2CH$_2$Cl$_2$ requires C, 60.65; H, 5.09; N, 22.30%.

EXAMPLE 57

3-(5-Methylisoxazol-3-yl)-6-[(5-tert-butyl)pyridazin-3-yl]methyloxy-1,2,4-triazolo[3,4-a]phthalazine The title-compound was prepared from Intermediate 2 and 3-chloromethyl-5-tert-butylpyridine (prepared from 3-methyl-4-tert-butyl pyridazine (Acta Chemica, 1967, 21, 2104–2210) following the procedure given for Example 15 part a) using the procedure given for Example 15 part b, mp 219–221° C.; $^1$H NMR (360 MHz, CDCl$_3$) δ 1.33 (9H, s, 3 of CH$_3$), 2.59 (3H, s, CH$_3$), 5.97 (2H, s, CH$_2$), 6.87 (1H, d, J=0.8 Hz, Ar—H), 7.83 (1H, t, J=8.2 Hz, Ar—H), 7.94 (1H, t, J=8.8 Hz, Ar—H), 8.06 (1H, d, J=2.3 Hz, Ar—H), 8.31 (1H, d, J=7.7 Hz, Ar—H), 8.70 (1H, d, J=7.4 Hz, Ar—H), 9.23 (1H, d, J=2.5 Hz, Ar—H); MS (ES$^+$) m/e 416 [MH]$^+$; Anal. Found. C, 63,75; H, 5.04; N, 23.53; C$_{22}$H$_{21}$N$_7$O$_2$ requires C, 63.60; H, 5.10; N, 23.60%.

EXAMPLE 58

6-(Imidazol-4-yl)methyloxy-3-(5-methylisoxazol-3-yl)-1,2,4-triazolo[3,4-a]phthalazine a) 4- and 5-Hydroxymethyl-1-{[2-(trimethylsilyl)ethoxy]methyl}imidazole 4-Hydroxymethylimidazole (formed from the commercially available hydrochloride salt by treatment with saturated potassium carbonate solution and extraction into butanol) (1.08 g, 11 mmol) was added to a stirred suspension of sodium hydride (60% dispersion in oil) (441 mg, 11 mmol) in N,N-diimethylformamide at 0° C. under nitrogen. The mixture was stirred at 0° C. for 1 h then 2-(trimethylsilyl)ethoxymethyl chloride (1.95 ml, 11 mmol) was added dropwise. The mixture was stirred for 15 min then warmed to room temperature and stirred for 2 h. The solvent was evaporated in vacuo and the residue taken up in water and extracted into ethyl acetate (3×). The combined extracts were dried (MgSO$_4$) and evaporated in vacuo. Purification of the residue by flash chromatography on silica gel, eluting with 8% methanol/dicloromethane, gave a 1:1 mixture of the title-alcohols (1.5 g, 60%), $^1$H NMR (250 MHz, d$^6$-DMSO δ 0.00 (9H, s), 0.88 (2H, m), 3.49 (2H, m), 4.37 and 4.51 (2H, d, J=5.5 and 5.3 Hz, ), 4.92 and 5.15 (1H, t, J=5.5 and 5.3 Hz), 5.32 and 5.40 (2H, s), 6.87 and 7.12 (1H, s), 7.73 and 7.77 (1H, s); MS (ES$^+$) m/e 229 [MH]$^+$.

b) 3-[(5-Methylisoxazol-3-yl)-6-[2-(trimethylsilyl)ethyloxy]methyl imidazol-4-yl]methyloxy-1,2,4-triazolo[3,4-a]phthalazine and 3-[(5-methylisoxazol-3-yl)-6-[2-(trimethylsily)ethyloxy]methylimidazol-5-yl]methyloxy-1,2,4-triazolo[3,4-a]phthalazine The title-compounds were prepared from the preceding mixture of alcohols and Intermediate 1 using the procedure given in Example 1 and using lithium bis(trimethylsilyl) amide (1.0M solution in tetrahydrofuran) as base, $^1$H NMR (250 MHz, CDCl$_3$) δ 0.00 (9H, s), (0.91 (2H, m), 2.65 (3H, d, J=0.6 Hz), 3.55 (2H, m), 5.32 and 5.51 (2H, s), 5.69 and 5.81 (2H, s), 6.93 and 6.96 (1H, s), 7.50 and 7.87 (1H, s), 7.71 and 7.66 (1H, s), 7.84 (1H, m), 7.99 (1H, m), 8.22 and 8.33 (1H, d, J=8.0 and 7.4 Hz), 8.74 (1H, m); MS (ES$^+$) m/e 478 [MH]$^+$.

c) 6-(Imidazol-4-yl)methyloxy-3-[(5-methylisoxazol-3-yl)-1,2,4-triazolo[3,4-a]phthalazine The preceding mixture of compounds (180 mg, 0.4 mmol) was treated with 2M HCl solution (20 ml) and ethanol (10 ml) and the mixture heated under reflux for 5 h. After cooling to room temperature, the mixture was basified to pH 9 using saturated potassium carbonate solution and evaporated in vacuo. Purification of the residue by flash chromatography on silica gel using 4% methanol/dichloromethane as eluant, followed by recrystallisation from dichloromethane gave the title-compound (69 mg, 53%); mp 179–181° C.; $^1$H NMR (360 MHz, d$^6$-DMSO), δ 2.60 (3H, s, CH$_3$), 5.54 (2H, s, CH$_2$), 7.18 (1H, s, Ar—H), 7.44 (1H, br s, Ar—H), 7.72 (1H, s, Ar—H), 7.93 (1H, m, Ar—H), 8.08 (1H, m, Ar—H), 8.16 (1H, d, J=7.9 Hz, Ar—H), 8.56 (1H, d, J=8.0 Hz, Ar—H); MS (ES$^+$) m/e 348 [MH]$^+$; Anal. Found. C, 55.10; H, 3.90; N, 26.23. C$_{17}$H$_{13}$N$_7$O$_2$.0.35 CH$_2$Cl$_2$ requires C, 55.27; H, 3.66; N, 26.00%.

EXAMPLE 59

3-[(5-Methylisoxazol-3-yl)-6-(1-methyl-1,2,4-triazol-3-yl)methylamino-1,2,4-triazolo[3,4-a]phthalazine a) 1-Methyl-1,2,4-triazole-3-methylamine hydrochloride 1-Methyl-1,2,4-triazole-3-methanol (500 mg, 4.4 mmol) was added to ice-cold thionyl chloride (5 ml, 69 mmol). The mixture was heated at reflux for 0.75 h, then cooled to room temperature and evaporated in vacuo. The residue was partitioned between dichloromethane and aqueous sodium bicarbonate solution and the aqueous layer separated and further extracted with dichloromethane (×2). The combined organic extracts were dried (MgSO$_4$) and evaporated in vacuo. The residue was treated with 33% w/w aqueous ammonia (5 ml) and the mixture heated in a sealed tube at 80° C. for 16 h. After cooling to room temperature, the reaction mixture was evaporated in vacuo and azeotroped with ethanol to give the title-amine (600 mg, 92%), $^1$H NMR (250 MHz, d$^6$-DMSO) δ 3.88 (3H, s, Me), 4.04 (2H, s, CH$_2$), 8.36 (2H, br s, NH$_2$), 8.58 (1H, s, Ar—H).

b) 3-(5-Methylisoxazol-3-yl)-6-(1-methyl-1,2,4-triazol-3-yl)methylamino-1,2,4-triazolo[3,4-a]phthalazine A mixture of Intermediate 1 (200 mg, 0.700 mmol), the preceding amine hydrochloride (125 mg, 0.841 mmol) and triethylamine (0.7 ml, 5.0 mmol) in DMSO (11 ml) was heated at 100° C. under nitrogen for 48 h. The mixture was cooled to room temperature, water added and the solvents evaporated in vacuo. The residue was partitioned between dichloromethane and water and the organic layer separated, washed with water (×2), dried (MgSO$_4$) and evaporated in vacuo. Flash chromatography of the residue on silica gel, eluting with 1–10% methanol/dichloromethane (gradient elution) followed by recrystallisation (ethyl acetate) gave the title-product (5 mg, 2%), $^1$H NMR (360 MHz, CDCl$_3$/d$^6$-DMSO) δ 2.60 (3H, s, Me), 3.93 (3H, s, Me), 4.85 (2H, d, J=4.8 Hz, CH$_2$), 6.93 (1H, m, NH), 7.10 (1H, s, Ar—H), 7.78 (1H, m, Ar—H), 7.89 (1H, m, Ar—H), 8.07–8.10 (2H, m, 2 of Ar—H), 8.70 (1H, d, J=8 Hz, Ar—H); MS (ES$^+$) m/e 362 [MH]$^+$.

EXAMPLE 60

3-(5-Methylisoxazol-3-yl)-6-{(N-methyl),N-1(1-methyl-1,2,4-triazol-3-yl)methyl]amino}-1,2,4-triazolo[3,4-a]phthalazine a) (N-Methyl),[N-(1-methyl-1,2,4-triazol-3-yl)methyl]amine 1-Methyl-1,2,4-triazole-3-methanol (500 mg, 4.4 mmol) was added to ice-cooled thionyl chloride (5 ml, 69 mmol) and the mixture warmed to room temperature before being heated at reflux for 0.75 h. After cooling to room temperature, the mixture was evaporated in vacuo and the residue taken up in 40 w/w aqueous methylamine (5 ml, 68 mmol) and dioxan (5 ml) and heated in a sealed tube at 80° C. overnight. After cooling to room temperature, the mixture was evaporated in vacuo and azeotroped with ethanol, and the residue purified by chromatography on silica gel, eluting with dichloromethane/methanol/ammonia (60:80:1 to 40:8:1, gradient elution), to give the title-amine (440 mg, 80%), $^1$H NMR (250 MHz, d$^6$-DMSO) δ 2.28 (3H, s, Me), 3.62 (2H, s, CH$_2$), 3.81 (3H, s, Me), 8.35 (1H, s, Ar—H).

b) 3-(5-Methylisoxazol-3-yl)-6-[(N-methyl),[N-(1-methyl-1,2,4-triazol-3-yl)methyl]amino-1,2,4-triazolo[3,4-a]phthalazine Sodium hydride (57 mg of a 60% dispersion in oil, 1.4 mmol) was added to a stirred solution of the preceding amine (117 mg, 0.927 mmol) in DMF (8 ml) at room temperature under nitrogen and the mixture stirred for 1 h. After this time, Intermediate 1 (204 mg, 0.714 mmol) was added and the mixture heated at 60° C. for 22 h. The mixture was cooled to room temperature, water was added and the solvent was evaporated in vacuo. The residue was partitioned between dichloromethane and water, and the aqueous phase separated and re-extracted with dichloromethane (×1). The combined organic extracts were washed with brine (×1), dried (MgSO$_4$) and evaporated in vacuo. Chromatography of the residue on silica gel, eluting with methanol/dicloromethane (1% to 10%, gradient elution), followed by recrystallisation (ethyl acetate) gave the title-product (20 mg, 7.1) $^1$H NMR (360 MHz, CDCl$_3$3/d$^6$-DMSO) δ 2.58 (3H, s, Me), 3.16 (3H, s, Me), 3.97 (3H, 8, Me), 4.63 (2H, s, CH$_2$), 6.92 (1H, s, Ar—H), 7.82 (1H, dd, J=8.4 and 7.1 Hz, Ar—H), 7.91 (1H, ad, J=8.2 and 7.0 Hz, Ar—H), 8.10 (1H, s, Ar—H), 8.60 (1H, d, J=7.1 Hz, Ar—H), 8.74 (1H, d, J=7.1 Hz, Ar—H); MS (ES$^+$) m/e 376

EXAMPLE 61

3-(5-Isoxazol-3-yl)-6-(1-methyl-1,2,4triazol-3-yl)methyloxy-1,2,4-triazolo[3,4-a]phthalazine Prepared from the product of Example 34 part c (10 mg, 0.55 mmol) and 3-hydroxymethyl-1-methyl-1,2,4-triazole using the method of Example 1 to yield a pale yellow solid (73 mg, 38%), $^1$H NMR (360 MHz, CDCl$_3$) δ 3.97 (3H, s), 5.73 (2H, s), 7.40 (H, d, J=2 Hz), 7.82 (1H, t, J=7 Hz), 7.96 (1H, t, J=7 Hz), 8.08 (1H, s), 8.29 (1H, d, J=7 Hz), 8.64 (1H, d, J=2 Hz), 8.72 (1H, d, J=7 Hz); MS (ES$^+$) m/e 349 [MH]$^+$.

INTERMEDIATE 4

3-(Carboxaldehydechloroxime)-6-(2,2,2-trifluoroethyloxy)-1,2,4-triazolo-[3,4-a]phthalazine a) 3-Allyloxyformyloxime-6-(2,2,2-trifluoroethyloxy)-1,2,4-triazolo-[3,4-a]phthalazine The product of Example 70 part a (20 g, 70 mmol) was dissolved in dry DMF (350 ml) and cooled to −20° C. 2,2,2-Trifluoroethanol in dry DMF was cooled to 0° C. and lithium bis(trimethylsilyl)amide was added dropwise. The anion thus produced was added to the preceding solution maintaining the internal temperature below −20° C. The reaction was warmed to 0° C. After 0.5 h, the reaction was poured into saturated ammonium chloride solution, filtered, washed with water and dried to An yield a pale green solid (22 g, 89%), $^1$H NMR (250 MHz, CDCl$_3$) δ 4.82–4.86 (2H, m), 4.93 (2H, q, J=8 Hz), 5.28–5.45 (2H, m), 6.03–6.19 (1H, m), 7.89 (1H, dt, J=1 and 8 Hz), 8.22 (1H, dt, J=1 and 8 Hz), 8.24 (1H, dd, J=1 and 8 Hz), 8.58 (1H, s), 8.73 (1H, dd, J=I and 8 Hz); MS (ES$^+$) m/e 352 [MH]$^+$.

b) 3-Carboxaldehydeoxime-6-(2,2,2-trifluoroethyloxy)-1,2,4-[3,4-a]phthalazine

The preceding alkyl ether was suspended in a solution of triethylammonium formate in ethanol (1M), the suspension was purged with nitrogen, tetrakis (triphenylphosphine) palladium (0) (0.5 g) was added and the reaction was heated to reflux for 16 h. Most of the solvent was removed by evaporation and the residue was poured into water. The precipitate was filtered off, washed with water and then boiled in ethanol and allowed to cool and age 16 h before filtering and drying to yield a brown solid (18 g, 83%A) $^1$H NMR (250 MHz, d$^6$-DMSO) δ 5.30 (2H, q, J=9 Hz), 7.95–8.20 (3H, m), 8.52–8.58 (2H, m), 12.25 (1H, s); MS (ES$^+$) m/e 312 [MH]$^+$.

c) 3-Carboxaldehydechloroxime-6-(2,2,2-trifluoroethyloxy)-1,2,4-[3,4-a]phthalazine The preceding oxime (18 g, 60 mmol) was dissolved in DMF (500ml) and N-chlorosuccinimide (8.01 g, 60 mmol) was added. The reaction mixture was heated to 50° C. and wet hydrogen chloride was bubbled through the mixture. The reaction was allowed to cool and poured into cold, saturated brine. The product was filtered, washed with water and dried to yield a pale yellow solid (18 g, 87%) $^1$H NMR (250 MHz, CDCl$_3$) δ 5.20 (2H, q, J=8 Hz), 8.01–8.21 (3H, m), 8.58–8.61 (1H, m), 13.27 (1H, s); MS (ES$^+$) m/e 346 [MH]$^+$.

INTERMEDIATE 6

3-(Isoxazol-3-yl)-6-(2,2,2-trifluoroethyloxy)-1,2,4-triazolo-[3,4-a]phthalazine

Intermediate 4 (1.73 g, 5.01 mmol) was suspended in a stirred solution of vinyl acetate (2.0 ml) in dichloromethane (250 ml). A solution of triethylamine was added dropwise to the reaction mixture over a period of 0.5 h. The mixture was stirred for 1 h then the solvent was removed by evaporation and replaced with xylene (200 ml) and heated at its reflux for 16 h. The solvent was removed and the residue was purified by column chromatographed on silica gel using ethyl acetate/dichloromethane (1:4) as eluent, to yield the title-product (1.01 g, 60%); $^1$H NMR (250 MHz, d$^6$-DMSO) δ 5.31 (2H, q, J=9 Hz), 7.53 (1H, d, J=2 Hz), 8.02–8.23 (3H, m), 8.62 (1H, m), 9.30 (1H, d, J=2 Hz); MS (ES$^+$) m/e 336 [MH]$^+$.

EXAMPLE 62

6-(3-Isoxazolyl)-6-(2-methyl-1,2,4-triazol-3-yl)methyloxy-1,2,4-triazolo[3,4-a]phthalazine The title-compound was prepared from Intermediate 5 and 2-methyl-1,2,4-triazole-3-methanol (prepared using the conditions of Itoh and Okongi, EP-A-421210) following the procedure given in Example 1, $^1$H NMR (360 MHz, d$^6$-DMSO) δ 4.01 (3H, s, Me), 5.83 (2H, s, CH$_2$), 7.57 (1H, d, J=1.7 Hz, Ar—H), 7.96 (1H, m, Ar—H), 8.00 (1H, s, Ar—H), 8.12 (1H, t, J=7.3 Hz, Ar—H), 8.25 (1H, d, J=8.2 Hz, Ar—H), 8.58 (1H, d, J=7 Hz, Ar—H); MS (ES$^+$) m/e 349 [MH]$^+$.

EXAMPLE63

3-(3-Isoxazolyl)-6-(1-methylimidazol-4-yl)methyloxy-1,2,4-triazolo[3,4-a]phthalazine The title-compound was prepared from Intermediate 5 (150 mg, 0.45 mmol) and 4-hydroxymethyl-1-methylimidazole (55 mg, 5.0 mmol) using the procedure described in Example 1 (18 mg, 12%), mp 191–192° C.; $^1$H NMR (360 MHz, CDCl$_3$) δ 3.68 (3H, s, CH$_3$), 5.62 (2H, s, CH$_2$), 7.32 (1H, d, J=1.6 Hz, Ar—H), 7.43 (1H, s, Ar—H), 7.55 (1H, s, Ar—H), 7.78 (1H, t, J=8.2 Hz, Ar—H), 7.93 (1H, t, J=8.2 Hz, Ar—H), 8.27 (1H, d, J=7.9 Hz, Ar—H), 8.64 (1H, d, J=1.6 Hz, Ar—H), 8.68 (1H, d, J=7.9 Hz, Ar—H); MS (ES$^+$) m/e 348 [MH]$^+$.

EXAMPLE 64

3-(5-Hydroxymethylisoxazol-3-yl)-6-(2-pyridyl)methyloxy-1,2,4-triazolo-[3,4-a]phthalazine a) 5-Hydroxymethylisoxazole-3-carboxylic acid ethyl ester A solution of triethylamine (7.36 ml, 53 mmol) in diethyl ether (40 ml) was added dropwise over 4 h (syringe pump; 10 ml/hr) to a vigorously stirred solution of carbethoxychloraldoxime (8 g, 53 mmol) (prepared as described in J. Org. Chem., 1983, 48, 366) and propargyl alcohol (3.69 ml, 63 mmol) in diethyl ether (120 ml) at room temperature under nitrogen. The mixture was stirred for 48 h then diluted with diethyl ether (100 ml) and poured into water (100 ml). The organics were separated, washed with water (×1) then dried (MgSO$_4$) and the solvent evaporated in vacuo. Flash chromatography of the residue on silica gel, eluting with 1:1 ethyl acetate/hexane, gave the title-compound (6.9 g, 74%A), $^1$H NMR (250 MHz, CDCl$_3$) δ 1.42 (3H, t, J=7.1 Hz, CH$_3$), δ 2.34 (1H, br s, OH) δ 4.45 (2H, q, J=7.1 Hz, CH$_2$) δ 4.84 (2H, s, CH$_2$) δ 6.69 (1H, s, Ar—H); MS (ES$^+$) ml 172 [MH]$^+$.

b) 5-(Tetrahydropyran-2yl oxymethyl)-isoxazol-3-carboxylic acid ethyl ester 3,4-Dihydro-2H-pyran (2.07 ml, 23 mmol) and p-toluene sulfonic acid monohydrate (333 mg, 1.7 mmol) were added to a solution of the preceding ester (3 g, 17 mmol) in dichloromethane (60 ml), and the mixture stirred at room temperature under nitrogen for 18 h. The mixture was diluted with dichloromethane (50 ml), then washed with aqueous sodium carbonate solution (×1) and with water (×1). The organic phase was dried (MgSO$_4$) and the solvent evaporated in vacuo. Flash chromatography of the residue on silica gel, eluting with 25% ethyl acetate/hexane, gave the title-compound (3.24 g, 72%), $^1$H NMR (250 MHz, CDCl$_3$) δ 1.42 (3H, t, J=7.1 Hz, CH$_3$), 1.60–1.70) (6H, m, 3 of CH$_2$), 3.58 (1H, m, CH of CH$_2$), 3.84 (1H, m, CH of CH$_2$), 4.45 (2H, q, J=7.1 Hz, CH$_2$), 4.69 (11H, d, J=13.9 Hz, CH$_2$), 4.75 (1H, t, J=3.3 Hz, CH), 4.84 (1H, d, J=14.0 Hz, CH$_2$), 6.69 (1H, s, Ar—H); MS (ES$^+$) m/e 256 [MH]$^+$.

c) 5-(Tetrahydropyran-2-yloxymethyl)-isoxazol-3-carboxylic acid

Sodium hydroxide (2.01 g, 50 mmol) in water (20 ml) was added to a solution of the preceding ester (3.24 g, 13mmol) in methanol (12 ml). The mixture was stirred at room temperature for 0.67 h then the methanol evaporated in vacuo and the aqueous residue cooled using an ice/water bath. 2M Hydrochloric acid (19 ml, 38 mmol) was added slowly, keeping the temperature below 5° C. Ethanol (20 ml) was added and the mixture evaporated in vacuo. The solid formed was dissolved in water and acetic acid added (1 ml). The mixture was extracted into ethyl acetate (6×) and the combined extracts were dried MgSO$_4$) and evaporated to give the title-compound (1.93 g, 67%); $^1$H NMR (360 MHz, d$^6$-DMSO) δ 1.40–1.60 (6H, m, 3 of CH$_2$), 3.49 (1H, m, CH of CH$_2$), 3.75 (1H, m, CH of CH$_2$), 4.68 (1H, d, J=13.7 Hz, CH$_2$), 4.73 (1H, m, CH), 4.78 (1H, d, J=13.8 Hz, CH$_2$), 6.82 (1H, s, Ar—H).

d) 6-Chloro-3-{[5-(tetrahydropyran-2-yloxy)methyl]-isoxazol-3-yl}-1,2,4-triazolo[3,4-a]phthalazine The title-compound was prepared from the preceding acid using the procedure described in Example 1 part c; $^1$H NMR (250 MHz, CDCl$_3$) δ 1.60–1.80 (6H, m, 3 of CH$_2$), 3.61 (1H, m, CH of CH$_2$), 3.92 (1H, m, CH of CH$_2$), 4.75 (2H, m, CH and CH of CH$_2$), 4.95 (1H, d, J=13.9 Hz, CH$_2$), 7.18 (1H, s, Ar—H), 7.99 (1H, m, Ar—H), 8.05 (1H, m, Ar—H), 8.33 (1H, m, Ar—H), 8.82 (1H, m, Ar—H); MS (ES$^+$) m/e 386 [MH]$^+$.

e) 3-{[5-(Tetrahydropyran-2-yloxy)methyl]-isoxazol-3-yl}-6-(2-pyridylmethyloxy-1,2,4triazolo[3,4-a]phthalazine The title-compound was prepared from 6-hydroxy-3-{[5-(tetrahydropyran-2-yloxy)methyl]isoxazol-3-yl}-1,2,4-triazolo[3,4-a]phthalazine and picolyl chloride following the procedure given for Example 15, $^1$H NMR (250 MHz, CDCl$_3$) δ 1.60–1.80 (6H, m, 3 of CH$_2$), 3.60 (1H, m, CH of CH$_2$), 3.91 (1H, m, CH of CH$_2$), 4.80 (1H, d, J=13.8 Hz, CH of CH$_2$), 4.84 (1H, m, CH), 4.95 (1H, d, J=13.7 Hz, CH of CH$_2$), 5.77 (2H, s, CH$_2$), 7.13 (1H, s, Ar—H), 7.29 (1H, m, Ar—H), 7.83 (2H, m, 2 of Ar—H), 7.86 (1H, m, Ar—H), 7.98 (1H, m, Ar—H), 8.33 (1H, m, Ar—H), 8.70 (2H, m, 2 of Ar—H); MS (ES$^+$) m/e 459 [MH]$^+$.

f) 3-(5-Hydroxymethylisoxazol-3-yl)-6-(2-pyridyl)methyloxy-1,2,4-triazolo[3,4-a]phthalazine Pyridinium-p-toluenesulfonate (16 mg, 0.6 mmol) was added to the preceding phthalazine (295 mg, 6 mmol) in ethanol (10 ml) and the mixture heated at 55° C. under nitrogen for 24 h. A further portion of pyridinium-p-toluenesulfonate (16 mg, 0.6 mmol) was added during this time. The mixture was evaporated in vacuo and water added. The solid formed was filtered off and washed successively with water and hexane. Flash chromatography of the residue on silica gel, eluting with 5% methanol/diclioromethane, followed by recrystallisation from ethyl acetate/dichloromethane gave the title-compound as a cream solid (89 mg, 30%), mp 129–131° C.; $^1$H NMR (360 MHz, d$^6$-DMSO) δ 4.74 (2H, d, J=5.9 Hz, CH$_2$), 5.92 (2H, s, CH$_2$), 5.84 (1H, t, J=6.0 Hz, OH), 7.14 (1H, s, Ar—H), 7.41 (1H, t, J=5.0 Hz, Ar—H), 7.76 (1H, d, J=7.8 Hz, Ar—H), 7.89 (1H, m, Ar—H), 7.99 (1H, t, J=7.7 Hz, Ar—H), 8.12 (1H, t, J=7.7 Hz, Ar—H), 8.34 (1H, d, J=8.1 Hz, Ar—H), 8.58 (1H, d, Ar—H), 8.62 (1H, d, Ar—H); MS (ES$^+$) m/e 375 [MH]$^+$; Anal. Found. C, 59.87; H, 3.72, N, 21.92. C$_{19}$H$_{14}$N$_6$O$_3$.0.1 CH$_2$Cl$_2$ requires C, 59.92; H, 3.74; N, 21.95%.

EXAMPLE 65

3-(5-Hydroxymethylisoxazol-3-yl)-6-(1-methyl-1,2,4-triazol-3-yl)methyloxy-1,2,4-triazolo[3,4-a]phthalazine a) 6-(1-Methyl-1,2,4-triazol-3-yl)methyloxy-3-{5-[(tetrahydropyran-2-yloxy)methyl]isoxazol-3-yl}-1,2,4-triazolo[3,4-a]phthalazine The title-compound was prepared using 6-chloro-3-[(5-tetrahydropyran-2-yloxymethyl)-isoxazol-3-yl-1,2,4-triazolot3,4-a]phthalazine (290 mg, 0.7 mmol) (prepared as described in Example 64 part d) and 1-methyl-1,2,4-triazole-3-methanol (94 mg, 0.8 mmol) (prepared using the conditions of Itoh and Okongi, EP-A-421210) using the procedure given for Example 1, $^1$H NMR (360 MHz, CDCl$_3$) δ 1.60–1.80 (6H, m, 3 of CH$_2$), 3.59 (1H, m, CH of CH$_2$), 3.92 (1H, m, CH of CH$_2$), 3.97 (3H, s, CH$_3$), 4.81 (1H, d, J=13.9 Hz, CH$_2$), 4.84 (1H, m, CH), 4.94 (1H, d, J=13.8 Hz, CH$_2$), 5.72 (2H, s, CH$_2$), 7.28 (1H, s, Ar—H), 7.79 (1H, m, Ar—H), 7.95 (1H, m, Ar—H), 8.09 (1H, s, Ar—H), 8.27 (1H, d, J=8.0 Hz, Ar—H), 8.70 (1H, d, Ar—H); MS (ES$^+$) m/e 463 [MH]$^+$.

b) 3-(5-Hydroxymethylisoxazol-3-yl)-6-(1-methyl-1,2,4-triazol-3-yl)methyloxy-1,2,4-triazolo[3,4-a]phthalazine The title-compound was prepared from the preceding phthalazine using the procedure given in Example 64 part f, mp 275–276° C.; $^1$H NMR (360 MHz, d$^6$-DMSO) δ 3.91 (3H, s, CH$_3$), 4.74 (2H, d, J=6.0 Hz, CH$_2$), 5.62 (2H, s, CH$_2$), 5.82 (1H, t, J=6.0 Hz, OH), 7.39 (1H, s, Ar—H), 7.95 (1H, t, J=8.1 Hz, Ar—H), 8.11 (1H, t, J=7.6 Hz, Ar—H), 8.17 (1H, d, J=8.0 Hz, Ar—H), 8.56 (1H, s, Ar—H), 8.60 (1H, d, Ar—H); MS (ES$^+$) m/e 379 [MH]$^+$. Anal. Found. C, 53.72; H, 3.74; N, 28.57. C$_{17}$H$_{14}$N$_8$O$_3$.0.3CH$_3$OH requires C, 53.56; H, 3.95; N, 28.88%.

EXAMPLE 66

3-(5-Fluoromethylisoxazol-3-yl)-6-(2-pyridyl)methyloxy-1,2,4-triazolo[3,4a]phthalazine a) Ethyl 5-fluoromethylisoxazole-3-carboxylate A solution of DAST (2.260 g, 14.02 mmol) in dichloromethane (15 ml) was added dropwise to a stirred solution of ethyl 5-hydroxymethylisoxazole-3-carboxylate (2.000 g, 11.69 mmol) in dichloromethane (20 ml) at −78° C. under nitrogen. The mixture was stirred at −78° C. for 0.83 h and then at room temperature for 2.5 h. Water (6 ml) and 2.5% aqueous sodium bicarbonate solution (25 ml) were added successively and the organic layer separated, dried MgSO$_4$) and evaporated in vacuo. Chromatography of the residue on silica gel eluting with 9:1 dichloromethane/hexane, gave the title-ester (1.397 g, 69° h), $^1$H NMR (250 MHz, CDCl$_3$) δ 1.43 (3H, t, J=7.2 Hz, Me), 4.47 (2H, q, J=7.1 Hz, CH$_2$), 5.48 (2H, d, J=47 Hz, CH$_2$F), 6.83 (1H, d, J=2.7 Hz, Ar—H).

b) 5-Fluoromethylisoxazole-3-carboxylic acid

10% Aqueous sodium hydroxide solution (5 ml) was added to a stirred solution of the preceding ester (1.884 g, 10.88 mmol) in ethanol (5 ml) at room temperature. After stirring overnight, the solvents were evaporated in vacuo and the residue dissolved in water and acidified to pH 1 with 35% hydrochloric acid. Ethanol was added, the solvents evaporated in vacuo and the residue azeotroped with ethanol. Ethanol was added and the mixture filtered to remove inorganic solids. Evaporation in vacuo of the filtrate gave the title-acid (0.921 g, 58%), $^1$H NMR (250 MHz, d$^6$-DMSO), 5.55 (2H, d, J=47 Hz, CH$_2$F), 6.77 (1H, br s, Ar—H).

c) 6-Chloro-3-(5-fluoromethylisoxazol-3-yl)-1,2,4-triazolo[3,4-a]phthalazine

The title-compound was prepared from the preceding acid using the procedure given for Intermediate 1 part c, $^1$H NMR (360 MHz, CDCl$_3$/d$^6$-DMSO) δ 5.60 (2H, d, J=47 Hz, CH$_2$F), 7.34 (1H, d, J=2.8 Hz, Ar—H), 7.98 (1H, m, Ar—H), 8.11 (1H, m, Ar—H), 8.36 (1H, d, J=8.0 Hz, Ar—H), 8.82 (1H, d, J=8.0 Hz, Ar—H); MS (ES$^+$) m/e 304 [MH]$^+$.

d) 3-(5-Fluoromethylisoxazol-3-yl)-6-(2-pyridyl)methyloxy-1,2,4-triazolo[3,4-a]phthalazine The title-compound was prepared from the preceding product and 2-pyridylcarbinol using the procedure given for Example 1, $^1$H NMR (360 MHz, CDCl$_3$) δ 5.59 (2H, d, J=47 Hz, CH$_2$F), 5.78 (2H, s, CH$_2$O), 7.26–7.32 (2H, m, 2 of Ar—H), 7.74–7.87 (3H, m, 3 of Ar—H), 7.98 (1H, m, Ar—H), 8.34 (1H, d, J=7.8 Hz, Ar—H), 8.66–8.72 (2H, m, 2 of Ar—H); MS (ES$^+$) m/e 377 [MH]$^+$.

EXAMPLE 67

3-(5-Fluoromethylisoxazol-3-yl)-6-(1-methyl-1,2,4-triazol-3-yl)methyloxy-1,2,4-triazolo[3,4-a]phthalazine Prepared from the product of Example 66 part c (85 mg, 0.28 mmol) and 3-hydroxymethyl-1-methyl-1,2,4-triazole using the method of Example 1 to yield a pale yellow solid (56 mg, 52%), $^1$H NMR (360 MHz, CDCl$_3$) δ 3.96 (3H, s), 5.58 (2H, d, J=44 Hz), 5.73 (2H, s), 7.51 (1H, s), 7.81 (1H, J=7 Hz), 7.96 (1H, t, J=7 Hz), 8.08 (1H, s), 8.30 (1H, d, J=7 Hz), 8.72 (1H, d, J=7 Hz); MS (ES$^+$) m/e 381 [MH]$^+$.

EXAMPLE 68

3-(5-Fluoromethylisoxazol-3-yl)-6-(1-methyl-1,2,4-triazol-5-yl)methyloxy-1,2,4-triazolo[3,4-a]phthalazine The title-compound was prepared from the product of Example 66 part c (150 mg, 0.5 mmol) and 2-methyl-1,2,4-triazole-3-methanol (61 mg, 0.53 mmol) (prepared using the conditions of Itoh and Okongi, EP-A-421210) using the procedure given in Example 1 using lithium bis(trimethylsilyl)amide (0.59 ml, 1.0M in tetrahydrofuran) as the base (80 mg, 43%), mp 250–252° C.; $^1$H NMR (360 MHz, d$^6$-DMSO) δ 4.01 (3H, s, CH$_3$), 5.76 (2H, d, J=47 Hz, CH$_2$), 5.83 (2H, s, CH$_2$), 7.70 (1H, d, J=Hz, Ar—H), 7.96 (1H, m, Ar—H), 8.02 (1H, s, Ar—H), 8.13 (1H, m, Ar—H), 8.25 (1H, d, J=7.8 Hz, Ar—H), 8.59 (1H, d, J=7.9 Hz, Ar—H);M$_1$S (ES$^+$) m/e 381 [MH]$^+$; Anal. Found. C, 52.31; H, 3.36; N, 28.64. C$_{17}$H$_{13}$N$_8$O$_2$F.0.15CH$_2$Cl$_2$ requires C, 52.40; H, 3.41; N, 28.51%.

EXAMPLE 69

3-(5-Fluoromethylisoxazol-3yl)-6-(1,2,4-triazol-3-yl)methyloxy-1,2,4-triazolo[3,4-a]phthalazine a) 3-(5-Fluoromethylisoxazol-3-yl)-6-[2-{[2-(trimethylsilyl)ethoxy]methyl}-1,2,4-triazol-3-yl) methyloxy-1,2,4-triazolo[3,4-a]phthalazine The title-compound was prepared from 6-chloro-3-(5-fluoromethylisoxazol-3-yl)-1,2,4-triazolo[3,4-a]phthalazine (160 mg, 0.53mmol) and 3-hydroxymethyl-2-{[(2-trimethylsilyl)ethoxy]methyl}-1,2,4-triazole (133 mg, 5.8 mmol) using the procedure given for Example 10, using lithium bis(trimethylsilyl)amide (0.63 ml, 1.0M in tetrahydrofuran) as base, (101 mg, 41%), $^1$H NMR (250 MHz, CDCl$_3$) δ 0.00 (9H, s, SiMe$_3$); 0.89 (2H, m, CH$_2$), 3.67 (2H, m, CH$_2$), 5.62 (2H, d, J=47 Hz, CH$_2$), 5.84 (2H, s, CH$_2$), 5.92 (2H, s, CH$_2$), 7.36 (1H, d, J=2.8 Hz, Ar—H), 7.88 (1H, m, Ar—H), 7.97 (1H, s, Ar—H), 8.04 (1H, m, Ar—H), 8.34 (1H, d, J=7.7 Hz, Ar—H), 8.74 (1H, d, Ar—H); MS (ES$^+$) m/e 497 [MH]$^+$.

b) 3-(5-Fluoromethylisoxazol-3-yl)-6-(1,2,4-triazol-3-yl)methyloxy-1,2,4-triazolo[3,4-a]phthalazine The title-compound was prepared from the preceding phthalazine (101 mg, 0.2 mmol) using the procedure given in Example 58 part c (60 mg, 80%), mp 266–268° C.; $^1$H NMR (360 MHz, d$^6$-DMSO) δ 5.70 (2H, s, CH$_2$), 5.76 (2H, d, J=47 Hz, Ar—H), 7.72 (1H, d, J=3.5 Hz, Ar—H), 7.97 (1H, m, Ar—H), 8.12 (1H, m, Ar—H), 8.23 (1H, d, J=7.8 Hz, Ar—H), 8.44 (1H, br s, Ar—H), 8.60 (1H, d, J=7.2 Hz, Ar—H); MS (ES$^+$) m/e 367 [MH]$^+$; Anal. Found. C, 51.90; H, 3.06; N, 30.09. C$_{16}$H$_{11}$N$_8$O$_2$F.0.1H$_2$O requires C, 52.21; H, 3.07; N, 30.44.

EXAMPLE 70

3-(5-Ethoxyisoxazol-3-yl)-6-(2-pyridyl)methyloxy-1,2,4-triazolo[3,4-a]phthalazine a) 3-(O-Allyloxyformyloxime)-6-chloro-1,2,4-triazolo[3,4-a]phthalazine 1-Chloro-4-hydrazinophthalazine (5.0 g, 25.7 mmol) and O-alkylglyoxal oxime (JP-A-6312673) (3.87 g, 30 mmol) in dichloromethane (200 ml) with triethylamine (7.7 g, 60 mmol) was cooled to 0° C. and bis(2-oxo-3-oxazolidinyl) phosphinic chloride (7.6 g, 60 mmol) was added. The reaction mixture was allowed to warm to room temperature and was stirred for 16 h. The solvent was removed by evaporation and the residue was triturated with water, xylene (200 ml) and triethylamine hydrochloride (0.5 g) were added and the reaction was heated to 150° C. for 2 h. The xylene solution was washed with water and evaporated to give a yellow solid which was purified by column chromatography on silica gel, eluting with ethyl acetate/hexane (1:4) followed by recrystallisation from dichloromethane/hexane to yield a pale yellow solid (2.3 g, 31%), $^1$H NMR (250 MHz, CDCl$_3$) δ 4.87–4.90 (2H, m), 5.30–5.47 (2H, m), 6.03–6.18 (1H, m), 7.90–7.96 (1H, m), 8.03–8.06 (1H, m), 8.29–8.32 (1H, m), 8.64 (1H, s), 8.76–8.85 (1H, m); MS (ES$^+$) m/e 288 [MH]$^+$.

b) 3-(O-Allyloxyformyloxime)-6-(2-pyridyl)methyloxy-1,2,4-triazolo[3,4-a]phthalazine 2-Pyridine methanol (0.824 g, 7.56 mmol) and the preceding phthalazine (2.17 g, 7.56 mmol) were dissolved in dry DMF (25 ml) and cooled to −20° C. before adding lithium bis(trimethylsilyl)amide (1M in THF, 7.6 ml) dropwise, maintaining the temperature of the reaction below −10° C. After 0.5 h, the reaction mixture was poured into water and extracted with dichloromethane. The organic layer was dried (MgSO$_4$), filtered and evaporated to yield an oil, which was purified by chromatography on silica gel, eluting with methanol/dichloromethane (1:99), to give a white solid (1.3 g, 48%), $^1$H NMR (250 MHz, CDCl$_3$) δ 4.84–4.86 (2H, m), 5.28–5.45 (2H, m), 5.71 (1H, s), 6.11 (1H, m), 7.30 (1H, m), 7.62 (1H, s); 7.48–7.81 (2H, m) 7.91 (1H, m), 8.29 (1H, m), 8.57 (1H, s), 8.66 (1H, m); MS (ES$^+$) m/e 361 [MH]$^+$.

c) 3-(Carboxaldehydeoxime)-6-(2-pyridyl)methyloxy-1,2,4-triazolo[3,4-a]phthalazine The preceding alkyl ether (1.1 g, 3.06 mmol) was suspended in a 1M solution of triethylammonium formate in ethanol 2 ml of water were added and then the suspension was purged with nitrogen. Tetrakis (triphenylphosphine) palladium (0) (30 mg) was added and the reaction was heated to reflux for four hours. The reaction was cooled to 4° C. and aged for 16 h. The product was filtered off and dried to yield 0.86 g of the product as a white solid (88%), $^1$H NMR (250 MHz, d$^6$-DMSO) δ 5.73 (2H, s), 7.45 (1H, m), 7.81 (1H, m), 7.92–8.03 (2H, m), 8.14 (1H, m), 8.36 (1H, m), 8.51 (1H, s), 8.58 (1H, m), 8.68 (1H, m), 12.29 (1H, s); MS (ES$^+$) m/e 321 [MH]$^+$.

d) 3-(Carboxaldehydechloroxime)-6-(2-pyridyl)methyloxy-1,2,4-triazolo[3,4-a]phthalazine The preceding oxime (2.53 g, 7.9 mmol) and N-chlorosuccinimide (1.12 g, 7.9 mmol) were suspended in dry DMF and heated until the reactants had dissolved. The reaction was stirred for 16 h, filtered and the white product obtained was washed with water, methanol and ether and dried to yield 5.8 g (74%) of a white solid, $^1$H NMR (250 MHz, d$^6$-DMSO) δ 5.69 (1H, s), 7.47 (1H, m), 7.82 (1H, m), 7.94–8.05 (2H, m), 8.16–8.22 (1H, m), 8.63 (1H, m), 13.38 (1H, s); MS (ES$^+$) m/e 355 [MH]$^+$.

e) 3-(5-Ethoxyisoxazol-3-yl)-6-(2-pyridyl)methyloxy-1,2,4-triazolo[3,4-a]phthalazine The preceding chloroxime (50 mg) was suspended in a solution of ethoxyacetylene in dichloromethane (20%, 20 ml) and triethylamine (43 mg) was added. The reaction was stirred for 16 h and then washed with dilute ammonium hydroxide, dried (MgSO$_4$), filtered and evaporated. The residue was purified by silica chromatography to yield a pale yellow powder (40.5 mg, 74%), $^1$H NMR (250 MHz, CDCl$_3$) δ 1.85 (3H, t, J=7 Hz), 4.70 (2H, q, J=7 Hz), 6.07 (2H, s), 6.39 (1H, s), 7.59(1H,m), 8.06–8.27 (4H, m), 8.66 (1H, m), 8.93–9.02 (2H, m); MS (ES$^+$) m/e 389 [MH]$^+$.

INTERMEDIATE 6

3-(5-Ethoxyisoxazol-3-yl)-6-(2,2,2-trifluoroethyloxy)-1,2,4-triazolo[3,4-a]phthalazine Intermediate 4 (1.5 g, 4.34 mmol) and ethoxyacetylene (5 ml of a 40% w/w solution in hexane) were suspended in dichloromethane and triethylamine (1.5 g, 14.8 mmol) in 100 ml dichloromethane was added dropwise to the mixture over 1 h. The reaction was washed with water and the organic layer was dried (MgSO$_4$), filtered and evaporated. The residue was purified by column chromatography on silica, eluting with ethyl acetate/dichloromethane (1:4), to yield a white solid (0.85 g, 51%), $^1$H NMR (250 MHz, CDCl$_3$) δ 1.50 (3H, t, J=7 Hz), 4.40 (2H, d, J=7 Hz), 5.00 (2H, d, J=9 Hz), 6.06 (1H, s), 7.88 (1H, dt, J=1 and 7 Hz), 8.03 (1H, dt, J=1 and 7 Hz), 8.28 (1H, dd, J=1 and 7 Hz), 8.73 (1H, dd, J=1 and 7 Hz); MS (ES$^+$) m/e 380 [MH]$^+$.

EXAMPLE 71

3-(5-Ethoxyisoxazol-3-yl)-6-(1-methyl-1,2,4-triazol-3-yl)methyloxy-1,2,4-triazolo[3,4-a]phthalazine Lithium hexamethyldisilazide (1.0M solution in hexane) (0.22 ml, 1.10 mmol) was added to stirred solution of 3-hydroxymethyl-1-methyl-1,2,4-triazole (90 mg, 0.79 mmol) prepared using the conditions of Itoh and Okongi, EP-A-421210) in N,N-dimethylformamide (10 ml) at −10° C. under nitrogen, and the mixture stirred for 0.25 h. After this time, Intermediate 6 (100 mg, 0.53 mmol) was added and the mixture stirred at −10° C. for 0.5 h and then room temperature overnight. Water was added to the reaction mixture and the resulting precipitate filtered off and recrystallised from dichloromethane/ethyl acetate to give the title-phthalazine (55 mg, 27%), mp 221–223° C.; $^1$H NMR (360 MHz, CDCl$_3$) δ 1.54 (3H, t, J=10.2 Hz; CH$_3$), 3.96 (3H, s, CH$_3$), 4.47 (2H, q, J=10.2 Hz, CH$_2$), 5.71 (2H, s, CH$_2$), 6.26 (1H, s, Ar—H), 7.79 (1H, m, Ar—H), 7.94 (1H, m, Ar—H), 8.08 (1H, s, Ar—H), 8.25 (1H, d, J=11.0 Hz, Ar—H), 8.70 (1H, d, J=8.1 Hz, Ar—H); MS (ES$^+$) m/e 393 [MH]$^+$; Anal. Found. C, 54.87; H, 3.91; N, 28.27; C$_{18}$H$_{16}$N$_8$O$_3$ requires C, 55.09; H, 4.11; N, 28.55%.

EXAMPLE 72

3-(5-Ethoxyisoxazol-3-yl)-6-(2-methyl-1,2,4-triazol-3-yl)methyloxy-1,2,4-triazolo[3,4-a]phthalazine The title compound was prepared from Intermediate 6 and 2-methyl 1,2,4-triazle-3-methanol (prepared using the conditions of Itoh and Okongi, EP-A-421210) following the procedure given in Example 71, mp 223–225° C.; $^1$H NMR (360 MHz, CDCl$_3$) δ 1.54 (3H, t, J=7.1 Hz, CH$_3$), 4.11 (3H, s, CH$_3$), 4.39 (2H,q, J=7.1 Hz, CH$_2$), 5.83 (2H,s, CH$_2$), 6.12 (1H, Ar—H), 7.80 (1H, m, Ar—H), 7.91 (1H, s, Ar—H), 7.95 (1H, m, Ar—H), 8.24 (1H, d, J=8.0 Hz, Ar—H), 8.70 (1H, d, J=7.9 Hz, Ar—H); MS (ES$^+$) m/e 393 [MH]$^+$; Anal. Found. C, 54.30; H, 3.67; N, 27.80; C$_{18}$H$_{16}$N$_8$O$_3$ requires C, 54.22; H, 4.07; N, 27.95%.

EXAMPLE 73

3-(5-Ethoxyisoxazol-3-yl)-6-(1,2,4-triazol-3-yl)methyloxy-1,2,4-triazolo[3,4-a]phthalazine a) 3-(5-Ethoxyisoxazol-3-yl)-6-{[1-(trimethylsilyl)ethoxy]methyl-1,2,4-triazol-5-yl}methyloxy-1,2,4-triazolo[3,4-a]phthalazine The title compound was prepared from Intermediate 6 (300 mg, 0.8 mmol) and 3-hydroxymethyl-2-{[2-(trimethylsilyl)ethoxy]methyl}-1,2,4-triazole (199 mg, 0.9 mmol) following the procedure given in Example 71 (250 mg, 62%), $^1$H NM (250 MHz, CDCl$_3$) δ 0.12 (9H, s, 3 of CH$_3$), 0.85–0.91 (2H, m, CH$_2$), 1.58 (3H, t, J=7.0 Hz, CH$_3$), 3.63–3.69 (2H, m, CH$_2$), 4.44 (2H, q, J=7.1 Hz, CH$_2$), 5.85 (2H, s, CH$_2$), 5.91 (2H, s, CH$_2$), 6.16 (1H, s, Ar—H), 7.87 (1H, m, Ar—H), 7.95 (1H, s, Ar—H), 8.02 (1H, m, Ar—H), 8.33 (1H, d, Ar—H), 8.72 (1H, d, Ar—H); MS (ES$^+$) m/e 509 [MH]$^+$.

b) 3-(5-Ethoxyisoxazol-3-yl)-6-(1,2,4-triazol-3-yl)methyloxy-1,2,4-triazolo[3,4-a]phthalazine The title compound was prepared from the preceding phthalazine (250 mg, 0.5 mmol) using the procedure described in Example 58 part c, (66 mg, 35%), mp 240–243° C.; $^1$H NMR (360 MHz, d$^6$-DMSO) δ 1.46 (3H, t, J=7.0 Hz, CH$_3$), 4.51 (2H, q, J=7.0 Hz, CH$_2$), 5.72 (2H, s, CH$_2$), 6.61 (1H, s, Ar—H), 7.96 (1H, m, Ar—H), 8.11 (1H, m, Ar—H), 8.24 (1H, d, J=8.1 Hz, Ar—H), 8.51 (1H, br s, Ar—H), 8.56 (1H, d, Ar—H); MS (ES$^+$) m/e 379 [MH]$^+$; Anal. Found. C, 53.67; H, 3.33; N, 29.52; C$_{17}$H$_{14}$N$_8$O$_3$ requires C, 53.97; H, 3.73; N, 29.62%.

EXAMPLE 74

3-(5-Ethoxyisoxazol-3-yl)-6-(1-methylimidazol-4-yl)methyloxy-1,2,4-triazolo[3,4-a]phthalazine The title compound was prepared from Intermediate 6 (150 mg, 0.4 mmol) and 4-hydroxymethyl-1-methylimidazole (49 mg, 0.4 mmol) following the procedure given in Example 71 (45 mg, 18%), mp 189–190° C. $^1$H NMR (360 MHz, CDCl$_3$) δ 1.55 (3H, t, J=7.1 Hz, CH$_3$), 3.68 (3H, s, CH$_3$), 4.40 (2H, q, J=7.0 Hz, CH$_2$), 5.60 (2H, s, CH$_2$), 6.15 (1H, s, Ar—H), 7.41 (1H, s, Ar—H), 7.61 (1H, s, Ar—H), 7.77 (1H, m, Ar—H), 7.91 (1H, m, Ar—H), 8.26 (1H, d, J=7.8 Hz, Ar—H), 8.64 (1H, d, Ar—H); MS (ES$^+$) m/e 392 [MH]$^+$; Anal. Found. C, 57.85; H, 4.07; N, 24.48; C$_{19}$H$_{17}$N$_7$O$_3$ 0.15H$_2$O requires C, 57.91; H, 4.42; N, 24.88%.

EXAMPLE 75

3-(5-Chloroisoxazol-3-yl)-6-(2-pyridyl)nethyloxy-1,2,4-triazolo[3,4-a]phthalazine The product from Example 70, part d) (50 mg, 0.14 mmol) was suspended in vinylidine chloride (5 ml) with triethylamine (43 mg, 0.42 mmol). The reaction was stirred for 16 hours, diluted with dichloromethane and washed with 5% ammonia solution and then dried (MgSO$_4$), filtered and evaporated to yield a solid which was purified by preparative thin layer chromatography using methanol/dicloromethane (3:97) as elutant to yield 12.5 mg of pure product, $^1$H NMR (360 MHz, CDCl$_3$) 8.66–8.72 (2H, m), 8.35 (1H, d, J=7 Hz), 7.98 (1H, t, J=7 Hz), 7.85 (1H, t, J=7 Hz), 7.80–7.70 (2H, m), 7.28 (1H, m), 7.03 (1H, s), 5.76 (2H, s); MS (ES$^+$) 379 [MH]$^+$.

INTERMEDIATE 7

3-(5-Chloroisoxazol-3-yl)-6-(2,2,2-trifluoroethyloxy)-1,2,4triazolo[3,4-a]phthalazine Intermediate 4 (3.5 g, 10 mmol) was dissolved in THF (350 ml) and added dropwise to a stirred solution of triethylamine (2.02 g, 20 mmol) in vinylidine chloride (200 ml) over a period of two hours. The solvent was removed and the residue was purified by column chromatography on silica gel, eluting with ethyl acetate/dichloromethane (1:10), to yield the product as a white solid (1.9 g, 50%), ¹H NMR (250 MHz, d⁶-DMSO) δ 5.33 (2H, q, J=9 Hz), 7.66 (1H, s), 8.02–8.20 (3H, m), 8.59 (1H, m); MS (ES⁺) 379 [MH]⁺.

EXAMPLE 76

3-(5-Chloroisoxazol-3-yl)-6-(1-methyl-1,2,4-triazol-3-yl)methyloxy-1,2,4-triazolo[4,3-a]phthalazine Prepared in a similar manner to Example 71 using intermediate 7 (200 mg, 0.54 mmol) and 3-hydroxymethyl-1-methyl-1,2,4-triazole (73 mg) to yield a white solid (110 mg, 53%). ¹H NMR (250 MHz, CDCl₃) δ 3.98 (3H, s), 5.72 (2H, s), 7.33 (1H, s), 7.82 (1H, t, J=7 Hz), 7.98 (1H, t, J=7 Hz), 8.10 (1H, s), 8.30 (1H, d, J=7 Hz), 8.61 (1H, d, J=7 Hz); MS (ES⁺) 383 [MH]⁺.

EXAMPLE 77

3-(5-Chloroisoxazol-3-yl)-6-(2-methy-1,2,4-triazol-3-yl)methyloxy-1,2,4-triazolo[4,3-a]phthalazine Prepared in a similar manner to Example 71 using intermediate 7 (200 mg, 0.54 mmol) and 3-hydroxyxmethyl-2-methyl-1,2,4-triazole (73 mg) to yield a white solid (126 mg, 61%), 1H NMR (360 MHz, CDCl₃) δ 4.11 (3H, s), 5.83 (2H, s), 7.11 (1H, s), 7.86 (1H, t, J=7 Hz), 7.93 (1H, s), 8.00 (1H, J=7 Hz), 8.25 (1H, d, J=7 Hz), 8.73 (1H, d, J=7 Hz); MS (ES⁺) 383 [MH]⁺.

EXAMPLE 78

3-(5-Chloroisoxazol-3-yl)-6-(1-methylimidazol-4-yl)methyloxy-1,2,4-triazolo[3,4-a]phthalazine The title compound was prepared from Intermediate 7 and 1-methyl-4-hydroxymethylimidazole (J. Org. Chem. 1968, 33, 3758) using the procedure given for Example 71, ¹H NMR (360 MHz, CDCl₃) δ 3.69 (3H, s, Me), 5.61 (2H, s, CH₂), 7.13 (1H, s, Ar—H), 7.43 (1H, s, Ar—H), 7.50 (1H, s, Ar—H), 7.79 (1H, m, Ar—H), 7.93 (1H, m, Ar—H), 8.28 (1H, d, J=8.0 Hz, Ar—H), 8.66 (1H, d, J=8.0 Hz, Ar—H); MS (ES⁺) m/e 382 [H]⁺.

EXAMPLE 79

3-(5-Chloroisoxazol-3-yl)-6-(1,2,4-triazol-3-yl)methyloxy-1,2,4-triazolo[3,4-a]phthalazine a) 3-(5-Chloroisoxazol-3-yl)-6-[2-{[2-(trimethylsilyl)ethoxy]methyl}-1,2,4-triazol-3-yl)methyloxy-1,2,4-triazolo[3,4-a]phthalazine The title compound was prepared from Intermediate 7 (200 mg, 0.5 mmol) and 3-(hydroxymethyl)-2-{[2-(trimethylsilyl)ethoxy]methyl}-1,2,4-triazole (136 mg, 0.6 mmol) following the procedure given in Example 71 (10 mg, 39%), ¹H NMR (250 MHz, CDCl₃) δ 0.13 (9H, s, 3 of CH₃), 0.89 (2H, m, CH₂), 3.67 (2H, m, CH₂), 5.83 (2H, s, CH₂), 5.90 (2H, s, CH₂), 7.14 (1H, s, Ar—H), 7.88 (1H, m, Ar—H), 7.92 (1H, s, Ar—H) 8.01 (1H, m, Ar—H), 8.36 (1H, d, Ar—H), 8.72 (1H, d, Ar—H); MS (ES⁺) m/e 499 [MH]⁺.

b) 3-(5-Chloroisoxazol-3-yl)-6-(1,2,4-triazol-3-yl)methyloxy-1,2,4-triazolo[4,3-a]phthalazine The title compound was prepared from the preceding phthalazine (105 mg, 0.2 mmol) using the procedure described in Example 58 part c, (29 mg, 37%), mp 235–236° C.; ¹H NMR (500 MHz, d⁶-DMSO) δ 5.72 (2H, s, CH₂), 7.72 (1H, s, Ar—H), 7.98 (1H, m, Ar—H), 8.19 (1H, m, Ar—H), 8.25 (1H, d, Ar—H), 8.52 (1H, br s, Ar—H), 8.59 (1H, d, Ar—H); MS (ES⁺), m/e 369 [MH]⁺; Anal. Found. C, 47.93; H, 2.34; N, 29.14 $C_{15}H_9N_8O_2Cl$. 0.15$CH_2Cl_2$ requires C, 47.70; H, 2.46; N, 29.37%.

EXAMPLE 80

3-(5-Chloroisoxazol-3-yl)-6-(1-methylimidazol-5-yl)methyloxy-1,2,4-triazolo[3,4-a]phthalazine The title compound was prepared from Intermediate 7 and 5-hydroxymethyl-1-methylimiidazole using the procedure given for Example 71, ¹H NMR (360 MHz, CDCl₃) δ 3.79 (3H, s, Me), 5.68 (2H, s, CH₂), 7.05 (1H, s, Ar—H), 7.38 (1H, s, Ar—H), 7.55 (1H, s, Ar—H), 7.82 (1H, t, J=7.2 Hz, Ar—H), 8.00 (1H, m, Ar—H), 8.17 (1H, d, J=8.0 Hz, Ar—H), 8.68 (1H, d, J 8.0 Hz, Ar—H); MS (ES4) m/e 382 [MH]⁺.

EXAMPLE 81

3-(5-Chloroisoxazol-3-yl)-6-(4-methyl-1,2,4-triazol-3-yl)methyloxy-1,2,4-triazolo[3,4-a]phthalazine The title compound was prepared from Intermediate 7 (150 mg, 0.5 mmol) and 4-methyl-1,2,4-triazole-5-methanol (prepared using the conditions of Itoh and Okongi, EP-A-421210) following the procedure given for Example 71 (41 mg, 21%,) mp 239–241° C.; ¹H NMR (360 MHz, d⁶-DMSO) δ 3.80 (3H, s, CH₃), 5.86 (2H, s, CH₂), 7.80 (1H, s, Ar—H), 7.96 91H, m, Ar—H), 8.14 (1H, m, Ar—H), 8.62 (1H, s, Ar—H); MS (ES⁺) m/e 383 [MH]⁺; Anal. Found. C, 48.95; H, 2.98; N, 27.61. $C_{16}H_{11}N_8O_2Cl$. 0.21$CH_2Cl_2$ requires C, 48.60; H, 2.87; N, 27.97%.

EXAMPLE 82

6-(2-Pyridylmethyloxy)-3-(5-trifluoromethylisoxazol-3-yl)-1,2,4-triazolo[3 4-a]phthalazine Prepared in a similar manner to Example 70 step e using a solution of trifluoromethylacetylene in dichloromethane to yield a pale yellow solid (28 mg, 48%A), ¹H NMR (250 MHz, CDCl₃) δ 5.77 (2H, m), 7.30 (1H, m), 7.67 (1H, s), 7.68–8.00 (4H, m), 8.37 (1H, m), 8.64–8.75 (2H, m); MS (ES⁺)+413 [MH]⁺.

EXAMPLE 83

3-(5-Phenymethylisoxazol-3-yl)-6-[(2-pyridyl)methyloxy]-1,2,4-triazolo[3,4-a]phthalazine Prepared in a similar manner to Example 70 step e using 3-phenyl-1-propyne to yield a solid (35 mg, 57%), 1H NM (250 MHz, CDCl₃) δ 4.23 (2H, s), 5.73 (2H, s), 6.80 (1H, s), 7.26–7.37 (6H, m), 7.72–7.97 (4H, m), 8.31 (1H, m), 8.64 (2H, m); MS (ES)⁺435 [MH]⁺.

EXAMPLE 84

3-[5-(2-Pyridylisoxazol-3-yl]-6-(2-pyridyl)methyloxy-1,2,4-triazolo[3,4-a]phthalazine Prepared in a similar manner to Example 70 step e using 2-pyridyl acetylene. ¹H NMR (250 MHz, CDCl₃) δ 5.82 (2H, s), 7.28 (1H, m), 7.41 (1H, m), 7.75–8.20 (8H, m), 8.35 (1H, m), 8.68–8.70 (2H, m); MS (E)+422 [MH]⁺.

EXAMPLE 85

3-(4-Methylisoxazol-3-yl)-6-(2-pyridyl)methyloxy-1,2,4-triazolo[3,4-a]phthalazine a) 1-Propenylacetate Dimethylaminopyridine (6.31 g, 52 mmol) was added to a stirred mixture of propionaldehyde (30 g, 0.52 mol), acetic anhydride (263.6 g, 2.58 mol) and triethylamine (104.5 g, 1.03 mol) at room temperature under nitrogen. The mixture was stirred for 36 h, poured onto ice and stirred at −200° C. for 0.5 h, then allowed to warm to room temperature and the aqueous phase separated. This was extracted with diethyl ether (×3) and the combined organic extracts washed with saturated sodium hydrogen carbonate solution until neutralized, then washed with water (×1) and brine (×1), dried (MgSO$_4$) and the solvent evaporated in vacuo. Distillation at atmospheric pressure gave the title-compound (30 g, 58%), bp 108–118° C.; $^1$H NMR (250 MHz, CDCl$_3$) δ 1.65 (6H, m, CH$_3$ E/Z), 2.16 (3H, s, OCH$_3$ E, 2.18 (3H, s, OCH$_3$ Z), 4.93 (1H, quintet, J=6.8 Hz, CH Z), 5.43 (1H, m, CH E), 7.02 (2H, m, CH E/Z).

b) 4-Methylisoxazole-3-carboxylic acid ethyl ester

Carbethoxychloraldoxime (4.68 g, 31 mmol) (prepared as described in J. Org. Chem. 1983, 48, 366) in diethyl ether (20 ml) was added dropwise over 20min to a refluxing mixture of 1-propenyl acetate (29.98 g, 0.29 mol) and triethylamine (3.12 g, 0.29 mol) in diethyl ether (45 ml). The mixture was heated under reflux for 4.5 h then allowed to cool to room temperature and poured into water (100 m). The ether layer was separated, dried (MgSO$_4$) and evaporated in vacuo. The residue was heated at 180° C. for 5 h then allowed to cool and the acetic acid formed distilled off (110–115° C.). The residue was purified by flash chromatography on silica gel, eluting with 10% ethyl acetate/hexane, to give the title compound (650 mg, 2%), $^1$H NMR (250 MHz, CDCl$_3$) δ 1.41 (3H, t, J=7.1 Hz, CH$_3$), 2.24 (3H, d, J=1.1 Hz, CH$_3$), 4.44 (2H, m, CH$_2$), 8.30 (1H, d, J=1.1 Hz, CH).

c) 4-Methylisoxazole-3-carboxylic acid

The title compound was prepared from the above ester using the procedure described in Example 30 part c. $^1$H NMR (250 MHz, CDCl$_3$) δ 2.25 (3H, d, J=1.0 Hz, CH$_3$), 6.85 (1H, br s, OH), 8.34 (1H, q, J=1.0 Hz, Ar—H).

d) 6-Chloro-3-(4-methylisoxazol-3-yl)-1,2,4-triazolo[3,4-a]phthalazine

The title compound was prepared as described in Example 1 part c using the preceding acid. $^1$H NMR (250 MHz, CDCl$_3$) δ 2.45 (3H, d, J=1.1 Hz, CH$_3$), 7.96 (1H, m, Ar—H), 8.09 (1H, m, Ar—H), 8.35 (1H, m, Ar—H), 8.44 (1H, d, J=1.0 Hz, CH), 8.82 (1H, m, Ar—H).

e) 3-(4-Methylisoxazol-3-yl)-6-(2-pridyl)methyloxy-1,2,4-triazolo[3,4-a]phthalazine The title compound was prepared from the above chloride using the procedure described in Example 1 part d, mp 163.5–164.5° C.; $^1$H NMR (360 MHz, CDCl$_3$) δ 2.41 (3H, d, J=0.8 Hz, CH$_3$), 5.74 (2H, s, CH$_2$), 7.29 (1H, m, Ar—H), 7.75–7.77 (2H, m, 2 of Ar—H), 7.84 (1H, m, ar—H), 7.95 (1H, m, Ar—H), 8.32 (1H, m, Ar—H), 8.41 (1H, d, J=1.1 Hz, Ar—H), 8.66–8.70 (2H, m, 2 of Ar—H); MS (ES)$^+$)+ m/e 359 [MH]$^+$; Anal. Found. C, 63.46; H, 3.60; N, 22.74. C$_{19}$H$_{14}$N$_6$O$_2$ requires C, 63.68; H, 3.94; N, 23.45%.

EXAMPLE 86

3-(5-Chloro-4-methylisoxazol-3-yl)-6-(2-pyridyl)methyloxy-1,2,4-triazolo[3,4-a]phthalazine The title-compound was prepared from ethyl 5-chloro-4-methylisoxazole-3-carboxylate (Chem. Abs. 1965, 63, 13234 h) using the procedure given for Example 34, $^1$H NMR (360 MHz, CDCl$_3$) δ 2.37 (3H, s, Me), 5.73 (2H, s, CH$_2$), 7.29 (1H, t, J=4.5 Hz, Ar—H), 7.75–7.86 (3H, m, 3 of Ar—H), 7.97 (1H, m, Ar—H), 8.33 (1H, d, J=8.0 Hz, Ar—H), 8.66–8.70 (2H, m, 2 of Ar—H); MS (ES)$^+$m/e 393 [MH]$^+$.

EXAMPLE 87

3-(3-Methyl-1,2,4-oxadiazol-5-yl)-6-(2-pyridyl)methyloxy-1,2,4-triazolo[3,4-a]phthalazine The title-compound was prepared in a similar manner to Example 35 part d using 3-methyl-1,2,4-oxadiazole-5-hydrazoic acid, mp. 201–203° C.; $^1$H NMR (360 MHz, d$^6$-DMSO) δ 2.56 (3H, s), 5.65 (2H, s), 7.42 (1H, m), 7.85 (2H, m), 8.05 (1H t, J=7.6 Hz), 8.16 (H, t, J=7.7 Hz), 8.37 (1H, d, J=8.2 Hz), 8.60 (2H, m); MS (E)+m/e 360 [MH]$^+$; Anal. Found. C, 60.32; H, 3.39; N, 26.55. C$_{18}$H$_{13}$N$_7$O$_2$. 0.1EtOAc requires C, 60.03; H, 3.78; N, 26.63%.

EXAMPLE 88

3-(3-Cycloprolyl-1,2,4-oxadiazol-5-yl)-6-(2-pyridyl)methyloxy-1,2,4-triazolo[3,4-a]phthalazine The title-compound was prepared in a similar manner to Example 35 part d using 3-cyclopropyl-1,2,4-oxadiazole-5-hydrazoic acid, mp. 229–231° C.; $^1$H NMR (360 MHz, d$^6$-DMSO) δ 1.11 (4H, m), 2.35 (1H, m), 5.73 (2H, s), 7.42 (1H, m), 7.85 (2H, m), 8.11 (2H, m), 8.39 (1H, d, J=8.0 Hz), 8.62 (2H, m); MS (ES$^+$m/e 386 [MH]$^+$; Anal. Foud. C, 62.81; H, 3.71; N, 25.35. C$_{20}$H$_{15}$N$_7$O2. 0.05C$_6$H$_{14}$ requires C, 62.57; H, 4.06; N, 25.16%.

EXAMPLE 89

3-(3-Methyl-1,2,4-oxadiazol-5-yl)-6-(1-methyl-1,2,4-triazol-3-yl)methyloxy-1,2,4-triazolo[3,4-a]phthalazine a) 6-Chloro-3-(3-methy-1,2,4-oxadiazol-5-yl)-1,2,4-triazolo[3,4-a]phthalazine The title compound was prepared from 1,4-dichlorophthalazine and 3-methyl-(1,2,4-oxadiazol-5-yl)hydrazoic acid (prepared using the conditions of Gregory, Warburton and Seark, CAN 78:72156) in a similar manner to Example 35 part d, $^1$H NMR (250 MHz, CDCl$_3$) δ 2.64 (3H, s, CH$_3$), 8.03 (1H, m, ArH), 8.15 (1H, m, ArH), 8.41 (1H, d, J=7.9 Hz, ArH), 8.87 (1H, d, J=8.5 Hz, ArH); MS (ES$^+$) m/e 287 [MH]$^+$.

b) 3-(3-Methyl-1,2,4-oxadiazol-5-yl)-6-(1-methyl-1,2,4-triazol-3-yl)methyloxy-1,2,4-triazolo[3,4-a]phthalazine The title-compound was made from the preceding phthalazine and 1-methyl-1,2,4-triazole-3-methanol (prepared using the conditions of Itoh and Okongi, EP-A-421210) in a similar manner to Example 98, mp 283–285° C., $^1$H NMR (360 MHz, CDCl$_3$) δ 2.60 (3H, s, CH$_3$), 3.99 (3H, s, CH$_3$), 5.76 (2H, s, CH$_2$), 7.86 (1H, m, ArH), 7.99 (1H, m, ArH), 8.10 (1H, s, ArH), 8.31 (1H, d, J=8.0 Hz, ArH), 8.73 (1H, d, J=7.2 Hz, ArH); MS (ES$^+$) m/e 364 [MH]$^+$.

EXAMPLE 90

6-(1-Benzyl-1,2,4triazol-3-yl)-3-(5-methylisoxazol-3-yl)methyloxy-1,2,4-triazolo[3,4-a]phthalazine and 6-(2-Benzyl-1,2,4-triazol-3-yl)-3-(5-methylisoxazol-3-yl)methyloxy-1,2,4-triazolo[3,4-a]phthalazine The title-compounds were prepared from 3-(5-methylisoxazol-3-yl)-6-(1,2,4-triazol-3-yl)methyloxy-1,2,4-triazolo[3,4a]phthalazine and benzylbromide following the procedure given for Example 47. The two regioisomers were separated by M.P.L.C. [Lobar Lichroprep Si60 (40-63 μm) (Art. 10402)], eluting with 2% methanol/dichloromethane, to give the title-products (51 mg, 21%):

6-(2-Benzyl-1,2,4-triazol-3-yl)-3-(5-methylisoxazol-3-yl)methyloxy-1,2,4-triazolo[3,4-a]phthalazine (less polar isomer) $^1$H NMR (360 MHz, CDCl$_3$) δ 2.55 (3H, s, CH$_3$), 5.67 (2H, s, CH$_2$), 5.79 (2H, s, CH$_2$), 6.79 (1H, s, Ar—H), 7.07–7.09 (2H, m, 2 of Ar—H), 7.15–7.17 (3H, m, 3 of Ar—H), 7.71 (1H, t, J=8.4 Hz), 7.91–7.93 (2H, m, 2 of Ar—H), 8.01 (1H, s, Ar—H), 8.64 (1H, d, J=7.8 Hz, Ar—H); MS (ES$^+$) m/e 439 [MH]$^+$.

6-(1-Benzyl-1,2,4-triazol-3-yl)-3-(5-methylisoxazol-3-yl)methyloxy-1,2,4-triazolo[3,4-a]phthalazine (more polar isomer) $^1$H NMR (360 MHz, CDCl$_3$) δ 2.56 (3H, s, CH$_3$), 5.30 (2H, s, CH$_2$), 5.73 (2H, s, CH$_2$), 6.74 (1H, s, Ar—H), 6.95–6.98 (2H, m, 2 of Ar—H), 7.26–7.30 (3H, m, 3 of Ar—H), 7.79 (1H, t, J=6.3 Hz, Ar—H), 7.95 (1H, t, J=8.1 Hz, Ar—H), 8.09 (1H, s, Ar—H), 8.29 (1H, d, J=8.1 Hz, Ar—H), 8.71 (1H, d, J=7.9 Hz, Ar—H); MS (ES$^+$) m/e 439 [MH]$^+$; Anal. Found. C, 62.91; H, 4.20; N, 23.97. C$_{23}$H$_{18}$N$_8$O$_2$. 0.25 (CH$_3$CO$_2$C$_2$H$_5$) requires C, 62.53; H, 4.48; N, 24.31%.

EXAMPLE 91

6-(1-Butyl-1,2,4-triazol-3-yl)-3-(5-methylisoxazol-3-yl)methyloxy-1,2,4-triazolo[3,4-a]phthalazine The title-compound was prepared from 3-(5-methylisoxazol-3-yl)-6-(1,2,4-triazol-3-yl)methyloxy-1,2,4-triazolo[3,4-a]phthalazine and 1-iodobutane following the procedure given for Example 47. The two regioisomers were separated by M.P.L.C. [Lobar Lichroprep Si60 (40-63 μm) (Art. 10402)], eluting with 2.5% methanol/dichloromethane, to give the title-product as the more polar isomer, $^1$H NMR (360 MHz, CDCl$_3$) δ 0.97 (3H, t, J=7.4 Hz, CH$_3$), 1.41 (2H, m, CH$_2$), 1.32–1.41 (2H, m, CH$_2$), 2.57 (3H, s, CH$_3$), 4.19 (2H, t, J=7.2 Hz, CH$_2$), 5.72 (2H, s, CH$_2$), 6.98 (1H, s, Ar—H), 7.77 (1H, t, J=7.4 Hz, Ar—H), 7.95 (1H, t, J=8.1 Hz, Ar—H), 8.09 (1H, s, Ar—H), 8.29 (1H, d, J=8.0 Hz, Ar—H), 8.68 (1H, d, J=7.9 Hz); MS (ES$^+$) m/e 405 [MH]$^+$.

EXAMPLE 92

6-(2-Ethyl-1,2,4-triazol-3-yl)-3-(5-methylisoxazol-3-yl)methyloxy-1,2,4-iazolo[3,4-a]phthalazine The title-compound was prepared from 3-(5-methylisoxazol-3-yl)-6-1,2,4-triazol-3-yl)methyloxy-1,2,4-triazolo[3,4-a]phthalazine and iodoethane following the procedure given for Example 47. The two regioisomers were separated by M.P.L.C. [Lobar Lichroprep Si6O (40-63 μm) (Art. 10402)], eluting with 2.5% methanol/dichloromethane, to give the title-product as the less polar isomer, $^1$H NMR (360 MHz, CDCl$_3$) δ 1.52 (3H, t, J=7.2 Hz, CH$_3$), 2.58 (3H, s, CH$_3$), 4.43 (2H, q, J=7.2 Hz, CH$_2$), 5.84 (2H, s, CH$_2$), 6.87 (1H, d, J=0.7 Hz, Ar—H), 7.82 (1H, t; J=8.3 Hz, Ar—H), 7.79–7.84 (2H, m, 2 of Ar—H), 8.20 (1H, d, J=8.0 Hz, Ar—H), 8.70 (1H, d, J=7.8 Hz, Ar—H); MS (ES$^+$) m/e 377 [MH]$^+$.

EXAMPLE 93

3-(5-Methylisoxazol-3-yl)-6-(1-pronyl-1,2,4-triazol-3-yl)methyloxy-1,2,4-triazolo[3,4-a]phthalazine The title-compound was prepared from 3-(5-methylisoxazol-3-yl)-6-(1,2,4-triazol-3-yl)methyloxy-1,2,4-triazolo[3,4-a]phthalazine and 1-iodopropane following the procedure given for Example 47. The two regioisomers were separated by M.P.L.C. [Lobar Lichroprep Si60 (40-63 μm) (Art. 10402)], eluting with 2.5% methanol/dichloromethane, to give the title-product as the more polar isomer, $^1$H NMR (360 MHz, CDCl$_3$) δ 0.96 (3H, t, J=7.4 Hz, CH$_3$), 1.88–1.99 (2H, m, CH$_2$), 2.59 (3H, s, CH$_3$), 4.16 (2H, t, J=7.1 Hz, CH$_2$), 5.72 (2H, s, CH$_2$), 7.00 (1H, s, Ar—H), 7.81 (1H, t, J=7.3 Hz, Ar—H), 7.92 (1H, t, J=7.8 Hz, Ar—H), 8.10 (1H, s, Ar—H), 8.26 (1H, d, J=8.2 Hz, Ar—H), 8.74 (1H, d, J=8.1 Hz, Ar—H); MS (ES$^+$) m/e 391 [MH]$^+$; Anal. Found. C, 57.72; H, 4.52; N, 27.11. C$_{19}$H$_{18}$N$_8$O$_2$. 0.8 (CH$_3$CO$_2$C$_2$H$_5$). 0.05 CH$_2$Cl$_2$ requires C, 57.77; H, 4.90; N, 27.15%.

EXAMPLE 94

3-(5-Methylisoxazol-3-yl)-6-[1-(2,2,2-trifluoroethyl)-1,2,4-triazol-3-yl]methyloxy-1,2,4triazolo[3,4-a]phthalazine The title-compound was prepared from 3-(5-methylisoxazol-3-yl)-6-(1,2,4-triazol-3-yl)methyloxy-1,2,4-triazolo[3,4-a]phthalazine and 2,2,2-trifluoroethylsulphonate following the procedure given for Example 47. The two regioisomers were separated by M.P.L.C. [Lobar Lichroprep Si60 (40–63 μm) (Art. 10402)], eluting with 2.5% methanol/dichloromethane, to give the title-product as the more polar isomer, $^1$H NMR (360 MHz, CDCl$_3$) δ 8 2.58 (3H, s, CH$_3$), 4.81 (2H, q, J=8.1 Hz, CH$_2$), 5.75 (2H, s, CH$_2$), 6.94 (1H, d, J=0.7 Hz, Ar—H), 7.80 (1H, t, J=7.2 Hz, Ar—H), 7.98 (1H, t, J=8.0 Hz, Ar—H), 8.26–8.28 (2H, m, Ar—H), 8.70 (1H, d, J=7.7 Hz, Ar—H); MS (ES$^+$) m/e 431 [MH]$^+$.

EXAMPLE 95

6-(1-Ethylimidazol-5-yl)methyloxy-3-(5-methylisoxazol-3-yl)-1,2,4-triazolo[3,4-a] phthalazine a) Methyl 1-ethylimidazole-5-carboxylate and methyl 1-ethylimidazole-4-carboxylate Potassium carbonate (0.66 g, 4.8 mmol) and ethyl iodide (0.67 ml, 8.4 mmol) were added successively to a stirred suspension of methyl 4-imidazolecarboxylate (1.00 g, 7.93 mmol) in DMF (12 ml) at 0° C. under nitrogen. The mixture was stirred at 0° C. for 1 h and then at room temperature overnight. The solvent was evaporated in vacuo and the residue partitioned between dichloromethane and water. The aqueous layer was separated and re-extracted with dichloromethane (×1) and the combined organic extracts were dried (MgSO$_4$) and evaporated in vacuo. Flash chromatography of the residue on alumina, eluting with 50–100% ethyl acetate/hexane (gradient elution), gave the title-esters:

methyl 1-ethylimidazole-5-carboxylate (less polar isomer) (0.235 g, 19%), $^1$H NMR (360 MHz, CDCl$_3$) δ 1.44 (3H, t, J=7.2 Hz, CH$_3$), 3.86 (3H, s, Me), 4.35 (2H, q, J=7.2 Hz, CH$_2$), 7.60 (1H, s, Ar—H), 7.73 (1H, S, Ar—H); MS (ES$^+$) m/e 155 [MH]$^+$.

methyl 1-ethylimidazole-4-carboxylate (more polar isomer) (0.358 g, 29%), $^1$H NMR (360 MHz, CDCl$_3$) δ 1.47 (3H, t, J=7.4 Hz, CH$_3$), 3.89 (3H, s, CH$_3$), 4.03 (2H, q, J=7.4 Hz, CH$_2$), 7.50 (1H,m s, Ar—H), 7.64 (1H, s, Ar—H); MS (ES$^+$) 155 [MH]$^+$.

b) 5-Hydroxymethyl-1-ethylimidazole

Lithium aluminum hydride (1.49 ml of a 1.0M solution in THF, 1.49 mmol) was added dropwise to a stirred solution of methyl 1-ethylimidazole-5-carboxylate (230 mg, 1.49 mmol) in THF (10 ml) at 0° C. under nitrogen. The mixture was stirred at 0° C. for 0.5 h and at room temperature for 1.8 h, then recooled to 0° C. and saturated aqueous sodium sulphate solution (1.5 ml) added dropwise. The mixture was stirred at room temperature, filtered through a pad of Hyflo and evaporated in vacuo. The residue was azeotroped with ethanol (×1) and then flash chromatographed on silica gel, eluting with 10% methanol/dichloromethane, to give the title-alcohol (175 mg, 93%), $^1$H NMR (360 MHz, CDCl$_3$) δ 1.47 (3H, t, J=7.4 Hz, CH$_3$), 4.07 (2H, q, J=7.3 Hz, CH$_2$), 4.63 (2H, s, CH$_2$O), 6.90 (1H,s , Ar—H), 7.47 (1H, s, Ar—H); MS (ES$^+$) 127 [MH]$^+$.

c) 6-(1-Ethylimidazol-5-yl)methyloxy-3-(5-methylisoxazol-3-yl-1,2,4-triazolo[3,4-a]phthalazine The title-compound was prepared from the preceding alcohol and Intermediate 1 following the procedure given for Example 71, ¹H NMR (360 MHz, CDCl₃) δ 1.52 (3H, t, J=7.4 Hz, CH₃), 2.59 (3H, s, CH₃), 4.14 q, J=7.3 Hz, CH₂), 5.68 (2H, s, CH₂O), 6.86 (1H, d, J=0.7 Hz, Ar—H), 7.38 (1H, s, Ar—H), 7.61 (1H, s, Ar—H), 7.79 (1H, dd, J=7.2 and 8.4 Hz, Ar—H), 7.95 (1H, dd, J=7.1 and 8.3 Hz, Ar—H), 8.14 (1H, d, J=7.8 Hz, Ar—H), 8.70 (1H, d, J=8.3 Hz, Ar—H); MS (ES⁺) m/e 376 [MH]⁺; Anal. Found. C, 60.51; H, 30 4.39; N, 25.88. C₁₉H₁₇N₇O₂ requires C, 60.79; H, 4.56; N, 26.12%.

EXAMPLE 96

6-(1-Ethylimidazol-4-yl)methyloxy-3-(5-methylisoxazol-3-yl)-1,2,4-triazolo[3,4-a]phthalazine The title-compound was prepared from methyl 1-ethylimidazole-4-arboxylate using the procedure given for Example 95 parts b and c, ¹H NMR (360 MHz, CDCl₃) δ 1.46 (3H, t, J=7.4 Hz, CH₃), 2.59 (3H, s, CH₃), 3.98 (2H, q, J=7.3 Hz, CH₂), 5.61 (2H, s, CH₂O), 6.90 (1H, s, Ar—H), 7.48 (1H, d, J=1.1 Hz, Ar—H), 7.69 (1H, d, J=1.1 Hz, Ar—H), 7.77 (1H, m, Ar—H), 7.91 (1H, m, Ar—H), 8.27 (1H, d, J=8.2 Hz, Ar—H), 8.66 (1H, d, J=7.1 Hz, Ar—H); MS (ES⁺) m/e 376 [MH]⁺; Anal. Found. C, .60.67; H, 4.40; N, 25.65. C₁₉H₁₇N₇O₂. 0.05C₄H₈O₂ requires C, 60.72; H, 4.62; N, 25.82%.

EXAMPLE 97

6-(1-Ethyl-1,2,3-triazol-5-yl)methyloxy-3-(5-methylisoxazol-3-yl)-1,2,4-triazolo[3,4-a]phthalazine a) Methyl 1-ethyl-1,2,3-triazole-4-carboxylate, methyl 2-ethyl-1,2,3-triazole-4-carboxylate and methyl 1-ethyl-1,2,3-triazole-5-carboxylate Potassium carbonate (3.3 g, 24 mmol) and ethyl iodide (6.4 g, 41 mmol) were added successively to a stirred solution of methyl 1,2,3-triazole-4carboxylate (J. Het. Chem. 1976, 13, 589) (5.0 g, 39 mmol) in DMF (60 ml) at 0° C. under nitrogen. The mixture was stirred at 0° C. for 1 h and then at room temperature overnight. The solvent was evaporated in vacuo and the residue partitioned between dichloromethane and water. The aqueous layer was separated and extracted with dichloromethane (×1) and the combined organic extracts were dried (MgSO₄) and evaporated in vacuo. Flash chromatography of the residue on silica, eluting with 30–60% ethyl acetate/hexane (gradient elution) gave the title-esters:

methyl 1-ethyl-1,2,3-triazole-4-carboxylate (most polar isomer) (1.22 g, 20%), ¹H NMR (250 MHz, CDCl₃) δ 1.60 (3H, t, J=7.3 Hz, CH₂), 3.96 (3H, s, CH₃), 4.55 (2H, q, J=7.4 Hz, CH₃), 8.05 (1H, s, Ar—H); MS (ES⁺) m/e 156 [MH]⁺.

methyl 2-ethyl-1,2,3-triazole-4-carboxylate (least polar isomer) (2.59 g, 42%), ¹H NMR (250 MHz, CDCl₃) δ 1.60 (3H, t, J=7.4 Hz, CH₃), 3.96 (3H, s, CH₃), 4.49 (2H, q, J=7.4 Hz, CH₂), 8.11 (1H, s, Ar—H); MS (ES⁺) m/e 156 [MH]⁺.

methyl 1-ethyl-1,2,3-triazole-5-carboxylate (880 g, 14%), ¹H NMR (250 MHz, CDCl₃) δ 1.54 (3H, t, J=7.3 Hz, CH₃), 3.94 (3H, s, CH₃), 4.78 (2H, q, J=7.2 Hz, CH₂), 8.13 (1H, s, Ar—H); MS (ES⁺) m/e 156 [MH[⁺.

b) 5-Hydroxymethyl-1-ethyl-1,2,3-triazole

The title-compound was prepared from methyl 1-ethyl-1,2,3-triazole-5-carboxylate using the procedure given for example 95 part b, ¹H NMR (250 MHz, CDCl₃) δ 1.88 (3H, t, J=7.3 Hz, CH₃), 2.74 (1H, br s, OH), 4.76 (2H, q, J=7.3 Hz, CH₂), 5.09 (2H, s, CH₂), 7.87 (1H, s, Ar—H); MS (ES⁺) m/e 128 [MH]⁺.

c) 6-(1-Ethylimidazol-1,2,3-triazol-5-yl)methyloxy-3-(5-methylisoxazol-3-yl)-1,2,4-triazolo[3,4-a]phthalazine The title-compound was prepared from the preceding alcohol and Intermediate 1 following the procedure given for Example 71, ¹H NMR (360 MHz, CDCl₃) δ 1.62 (3H, t, J=7.3 Hz, CH₃), 2.59 (3H, d, J=0.7 Hz, CH₃), 4.57 (2H, q, J=7.3 Hz, CH₂), 5.80 (2H, s, CH₂), 6.85 (1H, d, J=0.8 Hz, Ar—H), 7.83 (1H, m, Ar—H), 7.99 (1H, m, Ar—H), 8.08 (1H, s, Ar—H), 8.13 (1H, d, J=8.0 Hz, Ar—H), 8.70 (1H, d, J=8.0 Hz, Ar—H); MS (ES⁺) m/e 377 [MH]⁺; Anal. Found. C, 57.37; H, 4.11; N, 29.73. C₁₈H₁₆N8O₂ requires C, 57.44; H, 4.28; N, 29.77%.

EXAMPLE 98

6-(1-Ethyl-1,2,3-triazol-4-yl)methyloxy-3-(5-methylFisoxazol-3-yl)-1,2,4-triazolo[3,4-a]phthalazine a) 4-Hydroxymethyl-1-ethyl-1,2,3-triazole The title-compound was prepared from methyl 1-ethyl-1,2,3-triazole-4-carboxylate (Example 97 part a) using the procedure given for Example 95 part b, ¹H NMR (360 MHz, CDCl₃) δ 1.56 (3H, t, J=7.3 Hz, CH₃), 2.81 (1H, t, J=6.0 Hz, OH), 4.41 (2H, q, J=7.3 Hz, CH₂), 4.79 (2H, d, J=5.9 Hz, CH₂), 7.55 (1H, s, Ar—H); MS (ES⁺) m/e 128 [MH]⁺.

b) 6-(1-Ethyl-1,2,3-triazol-4-yl)methyloxy-3-(5-methylisoxazol-3-yl)-1,2,4-triazolo[3,4-a]phthalazine Lithium hexamethyldisilazide (0.84 ml of a 1.0M solution in tetrahydrofuran, 0.8 mmol) was added dropwise to a stirred solution of the preceding alcohol (98 mg, 0.7 mmol) in dry N,N-dimethylformamide (20 ml) at −10° C. under nitrogen. The mixture was stirred at −10° C. for 0.5 h then Intermediate 1 (200 mg, 0.7 mmol) added in one portion and stirred at −10° C. for 2 h and then at room temperature overnight. The solvent was evaporated in vacuo and the residue taken up in water and extracted into dichloromethane (×3). The combined extracts were dried (MgSO₄) and evaporated in vacuo. Flash chromatography of the residue on silica gel, eluting with 2% methanol/dicloromethane, followed by recrystallisation from ethyl acetate gave the title-compound as a white solid (111 mg, 42%), ¹H NMR (360 MHz, CDCl₃) δ 1.56 (3H, t, J=7.4 Hz, CH₃), 2.61 (3H, s, CH₃), 4.41 (2H, q, J=7.4 Hz, CH₂), 5.77 (2H, s, CH₂), 6.90 (1H, d, J=0.8 Hz, Ar—H), 7.80 (1H, m, Ar—H), 7.94 (1H, m, Ar—H), 8.25 (1H, d, J=8.1 Hz, Ar—H), 8.66 (1H, d, J=8.0 Hz, Ar—H), 8.84 (1H, s, Ar—H); MS (ES⁺) m/e 377 [MH]⁺; Anal. Found. C, 57.02; H, 4.11; N, 29.61. C₁₈H₁₈N₈O₂ requires C, 57.44; H, 4.28; N, 29.77%.

EXAMPLE 99

6-(2-Ethyl-1,2,3-triazol-4-yl)methyloxy-3-(5-methylisoxazol-3-yl)-1,2,4-triazolo[3,4-a]phthalazine a) 2-Ethyl-4-hydroxymethyl-1,2,3-triazole The title-compound was prepared from methyl 2-ethyl-1,2,3-triazole-4-carboxylate (prepared as described in Example 97 part a) using the procedure given for Example 95 part b, ¹H NMR (250 MHz, CDCl₃) δ 1.56 (3H, t, J=7.3 Hz, CH₃), 2.08 (1H, t, J=5.9 Hz, OH), 4.45 (2H, q, J=7.3 Hz, CH₂), 4.77 (2H, d, J=5.8 Hz, CH₂), 7.56 (1H, s, Ar—H); MS (ES⁺) m/e 127 [MH]⁺.

b) 6-(2-Ethyl-1,2,3-triazol-4-yl)methyloxy-3-(5-methylisoxazol-3-yl)-1,2,4-triazolo[3,4-a]phthalazine The title-compound was prepared from the preceding alcohol and Intermediate 1 following the procedure given in Example 98, ¹H NMR (360 MHz, CDCl₃) δ 1.58 (3H, t, J=7.4 Hz, CH₃), 2.59 (3H, s, CH₃), 4.48 (2q, 7.3 Hz, CH₂), 5.74 (2H, s, CH₂), 6.90 (1H, s, Ar—H), 7.80 (1H, m, Ar—H), 7.94 (1H, m, Ar—H), 8.11 (1H, s, Ar—H), 8.22 (1H, d, J=8.0 Hz, Ar—H), 8.66 (1H, d, J=8.0 Hz, Ar—H); MS (ES⁺) m/e 377 [MH]⁺; Anal. Found. C, 57.77; H, 4.15; N, 29.63. C₈H₁₆N₈O₂ requires C, 57.44; H, 4.28; N, 29.77%.

EXAMPLE 100

3-(5-Methylisoxazol-3-yl)-6-(1-methyltetrazol-5-yl)methyloxy-1,2,4-triazolo[3,4-a]phthalazine The title-compound was prepared from Intermediate 2 and 5-chloromethyl-1-methyltetrazole (Chem. Pharm. Bull., 1989, 37, 322) following the procedure given for Example 15 part b, ¹H NMR (360 MHz, CDCl₃) δ 2.60 (3H, s, CH₃), 4.33 (3H, s, CH₃), 6.03 (2H, s, CH₂), 6.89 (1H, s, Ar—H), 7.91 (1H, t, J=7.4 Hz, Ar—H), 8.04 (1H, t, J=8.3 Hz, Ar—H), 8.25 (1H, d, J=7.9 Hz, Ar—H), 8.70 (1H, d, J=7.7 Hz, Ar—H); MS (ES⁺) m/e 364 [MH]⁺.

EXAMPLE 101

6-(Imidazol-2-yl)methyloxy-3-(5-methylisoxazol-3-yl)-1,2,4-triazolo[3,4-a]phthalazine a) 3-(5-Methylisoxazol-3-yl)-6-{[1-(2-trimethylsilyl)ethyloxymethy]imidazol-2-yl}methyloxy-1,2,4-triazolo[3,4-a]phthalazine Prepared from Intermediate 1 and 1-[(2-trimethylsilyl)ethyloxymethyl]imidazole-2-methanol (CAN 121:82872) following the procedure of Example 98) ¹H NMR (250 MHz, CDCl₃) δ 0.01 (9H, s, Si(CH₃)₃), 0.89 (2H, t, J=8.2 Hz, SiCH₂), 2.65 (3H, 8, CH₃), 3.58 (2H, t, J=8.2 Hz, CH₂O), 5.57 (2H, s, CH₂O), 5.86 (2H, s, CH₂O), 6.98 (1H, J=0.7 Hz, Ar—H), 7.17 (1H, d, J=0.7 Hz, ArH), 7.18 (1H, s, ArH), 7.81 (1H, t, J=7.7 Hz, Ar—H), 7.87 (1H, t, J=7.7 Hz, Ar—H), 8.27 (1H, d, J=7.7 Hz, Ar—H), 8.74 (1H, d, J=7.7 Hz, Ar—H); MS (ES⁺) 478 [MH]⁺.

b) 6-(Imidazol-2-yl)methyloxy-3-(5-methylisoxazol-3-yl)-1,2,4-triazolo[3,4-a]phthalazine The preceding protected imidazole (0.4 g, 0.84 mmol) was suspended in trifluoroacetic acid (5 ml) and dichloromethane (5 ml) and stirred for 16 h. 2 The solvent was removed and the residue was purified by column chromatography on silica gel eluting with 5% methanol/dichloromethane, to yield the product (0.08 g, 27%), mp 188–189° C., ¹H NMR (250 MHz, d₆-DMSO) δ 2.60 (3H, s, Me), 5.62 (211, s, CH₂O), 7.13 (1H, br s, ArH), 7.19 (1H, s, ArH), 7.94 (1H, t, J=7.7 Hz, ArH), 8.10 (1H, t, J=7.7 Hz, ArH), 8.22 (1H, d, J=7.7 Hz, Ar—H), 8.60 (1H, d, J=7.7 Hz, Ar—H), 12.46 (1H, br s, NH); MS (ES⁺) 348 [MH]⁺; Anal. Found. C, 58.13; H, 3.58; N, 27.42. C₁₇H₁₃N₇O₂. 0.25(H₂O) requires C, 58.03; H, 3.87; N, 27.87%.

EXAMPLE 102

3-(5-Methylisoxazol-3-yl)-6-(2-methylpyrazol-3-yl]methyloxy-1,2,4-triazolo[3,4-a]phthalazine The title-compound was prepared from Intermediate 1 and 1-methyl-5-hydroxymethylpyrazole (tiioorg. Med. Chein. Lett. 1997, 7, 1409) following the procedure given in Example 71, mp 270–270.50° C.; ¹H NMR (250 MHz, CDCl₃) δ 2.60 (3H, s, CH₃), 4.03 (3H, s, CH₃), 5.71 (2H, s, CH₂6.60 (1H, d, J=1.9 Hz, ArH), 6.86 (1H, s, ArH), 7.26 (1H, d, J=1.8 Hz, ArH), 7.82 (1H, m, ArH), 7.98 (1H, m, ArH), 8.18 (1H, d, J=7.9 Hz, ArH), 8.70 (1H, d, J=7.9 Hz, ArH); MS (ES⁺) m/e 362 [MH]⁺.

EXAMPLE 103

3-(5-Methylisoxazol-3-yl)-6-(1-methylpyrazol-3-yl)methyloxy-1,2,4-triazolo[3,4-a]phthalazine a) 3-(5-Methylisoxazol-3-yl)-6-(4-toluenesulphonyloxy)-1,2,4-triazolo[3,4-a]phthalazine 4-Toluenesulphonyl chloride (382 mg, 2 mmol) was added to a solution of Intermediate 2 (267 mg, 1 mmol) and triethylamine (202 mg, 2 mmol) in dichloromethane (7 ml) at 0° C. and stirred for 2 h. The solvent was removed and the residue was purified by column chromatography on silica gel, eluting with ethyl acetate/dichloromethane (1:1), to yield the product as a white solid (380 mg, 90%), ¹H NMR (250 MHz, CDCl₃) δ 2.50 (3H, s, CH₃), 2.62 (3H, s, CH₃), 6.81 (1H, s, ArH), 7.45 (2H, d, J=8.2 Hz, 2 of ArH), 7.93 (1H, m, ArH), 8.05 (1H, m, ArH), 8.26–8.32 (3H, m, 3 of ArH), 25 8.74 (1H, d, J=7.5 Hz, ArH); MS (ES⁺) m/e 422 [MH]⁺.

b) 3-(5-Methylisoxazol-3-yl)-6-(1-methylpyrazol-3-yl)methyloxy-1,2,4-triazolo[3,4-a]phthalazine The title-compound was prepared from the preceding phthalazine and 1-methyl-3-hydroxymethylpyrazole (*Zh. Obshch. Rhim.* 1982, 52, 2598) in a similar manner to Example 98, mp 243–244.50° C., ¹H NMR (250 MHz, CDCl₃) δ 2.60 (3H, s, CH₃), 3.94 (3H, s, CH₃), 5.66 (2H, s, CH₂), 6.64 (1H, d, J=2.2 Hz, ArH), 6.95 (1H, s, ArH), 7.38 (1H,d, J=2.2 Hz, ArH), 7.81 (1H, m, ArH), 7.97 (1H, m, ArH), 8.25 (1H, d, J=8.1 Hz, ArH), 8.70 (1H, d, J=7.5 Hz, ArH); MS (ES⁺) m/e 362 [MH]⁺; Anal. Found. C, 56.33; H, 4.56; N, 25.36. C₁₈H₁₅N₇O₂ requires C, 56.32; H, 4.59; N, 25.54%.

EXAMPLE 104

3-(5-Methylisoxazol-3-yl)-6-(1-methylpyrazol-4-yl)methyloxy-1,2,4-triazolo[3,4-a]phthalazine The title-compound was prepared from Intermediate 1 and 1-methyl-4-hydroxymethylpyrazole following the procedure given for Example 71, mp 212–213° C.; ¹H NMR (250 MHz, CDCl₃) δ 2.60 (3H, s, CH₃), 3.89 (3H, s, NCH₃), 5.56 (2H, s, CH₂O), 6.88 (1H, s, ArH), 7.74 (1H, s, ArH), 7.82 (1H, t, J=7.7 Hz, ArH), 7.96 (1H, t, J=7.7 Hz, ArH), 8.04 (1H, s, ArH), 8.18 (1H, d, J=7.7 Hz, ArH), 8.68 (1H, d, J=7.7 Hz, ArH); MS (ES⁺) 362 [MH]⁺.

EXAMLE 105

3-(5-Ethylisoxazol-3-yl)-6-(2-methyl-1,2,4-triazol-3-yl)methyloxy-1,2,4-triazolo[3,4-a]phthalazine a) 5-[2-(Phenoxythiocarbonyloxy)ethyl]isoxazole-3-carboxylic acid ethyl ester Pyridine (2.4 g, 31 mmol) was added to a stirred solution of 5-hydroxyethylisoxazole-3-carboxylic acid ethyl ester (4.75 g, 26 mmol) (prepared analogously to Example 64 part a) in dichloromethane (150 ml) under nitrogen at room temperature. The mixture was cooled to 0° C. and phenyl chlorothionoformate (5.3 g, 31 mmol) was added dropwise. The mixture was stirred at 0° C. for 1 hand at room temperature for 2 h, then diluted with dichloromethane (200 ml) and washed with water (×2). The organic layer was dried MgSO₄) and evaporated in, vacuo. Flash chromatography of the residue on silica gel, eluting with 20% ethyl acetate/hexane, gave the title-compound (6.7 g, 81%), ¹H NMR (250 MHz, CDCl₃) δ 1.43 (3H, t, J=7.1 Hz, CH₃), 3.37 (2H, t, J=6.3 Hz, CH₂), 4.46 (2H, q, J=7.1 Hz, CH₂), 4.83 (2H, t, J=6.3 Hz, CH₂), 6.60 (1H, s, Ar—H), 7.08–7.11 (2H, m, 2 of Ar—H), 7.29 (1H, m, Ar—H), 7.38–7.46 (2H, m, 2 of Ar—H); MS (ES⁺) m/e 322 [MH]⁺, m/e 168 [MH—154]⁺.

b) 5-Ethylisoxazole-3-carboxylic acid

Tris(trimethylsilyl)silane (8.9 g, 36 mmol) and azobisisobutyronitrile (153 mg, 2% w/w) were added successively to a stirred solution of the preceding ester (7.66 g, 24 mmol) in toluene (180 ml) at room temperature. The mixture was heated at 80° C. for 3 h then cooled to room temperature and the solvent evaporated in vacuo. Flash chromatography of the residue on silica gel, eluting with 0%–10% ethyl acetate/hexane (gradient elution), yielded crude 5-ethylisoxazole-3-carboxylic acid ethyl ester. The crude material was taken up in methanol (30 ml) and aqueous sodium hydroxide solution (60 ml, approx. 1.2M) added dropwise with stirring. The mixture was stirred at room temperature for 1 h then the solvents evaporated in vacuo and the residue taken up in water and washed with dichloromethane (×3). The aqueous phase was acidified using 2M hydrochloric acid and extracted into dichloromethane (×4). The combined extracts were dried ($MgSO_4$) and evaporated in vacuo to yield the title-compound as a white solid (1.15 g, 34%); $^1$H NMR (250 MHz, $CDCl_3$) δ 1.35 (3H, t, J=7.6 Hz, $CH_3$), 2.86 (2H, q, J=7.6 Hz, $CH_2$), 5.55 (1H, br s, OH), 6.48 (1H, s, Ar—H).

c) 6-Chloro-3-(5-ethylisoxazol-3-yl)-1,2,4-triazolo[3,4-a] phthalazine

The title-compound was prepared from the preceding acid following the procedure given for Example 1 part c, $^1$H NMR (250 MHz, $CDCl_3$) δ 1.42 (3H, t, J=7.6 Hz, $CH_3$), 2.94 (2H, q, J=7.6 Hz, $CH_2$), 6.89 (1H, s, Ar—H), 7.96 (1H, m, Ar—H), 8.08 (1H, m, Ar—H), 8.35 (1H, m, Ar—H), 8.81 (1H, m, Ar—H); MS ($ES^+$) m/e 302 $[MH]^+$.

d) 3-(5-Ethylisoxazol-3-yl)-6-(2-methyl-1,2,4-triazol-3-yl)methyloxy-1,2,4-triazolo[3,4-a]phthalazine The title-compound was prepared from the preceding chloride and 2-methyl-1,2,4-triazole-3-methanol (prepared using the conditions of Itoh and Okongi, EP-A-421210), following the procedure given in Example 98, mp 240–242° C.; $^1$H NMR (360 MHz, $CDCl_3$) δ 1.42 (3H, t, J=7.6 Hz, $CH_3$), 2.92 (2H, q, J=7.5 Hz, $CH_2$), 4.11 (3H, s, $CH_3$), 5.85 (2H, s, $CH_2$), 6.88 (1H, s, Ar—H), 7.83 (1H, m, Ar—H), 7.93 (1H, s, Ar—H), 7.99 (1H, m, Ar—H), 8.23 (1H, d, J=7.9 Hz, Ar—H), 8.70 (1H, d, J=8.0 Hz, Ar—H); MS ($ES^+$) m/e 377 $[MH]^+$; Anal. Found. C, 56.67; H, 4.15; N, 28.89. $C_{18}H_{16}N_8O_2$. $0.1CH_2Cl_2$ requires C, 56.49; H, 4.24; N, 29.11%.

EXAMPLE 106

3-(5-Ethylisoxazol-3-yl)-6-(1-methyl-1,2,4-triazol-3-yl)methyloxy-1,2,4-triazolo[3,4-a]phthalazine The title-compound was prepared from 6-chloro-3-(5-ethylisoxazol-3-yl)-1,2,4triazolo[4,3-a]phthalazine (prepared as described in Example 105 part c) and 3-hydroxymethyl-1-methyl-1,2,4-triazole (prepared using the conditions of Itoh and Okongi, EP-A-421210), following the conditions described in Example 98, mp 236–238° C.; $^1$H NMR (360 MHz, $CDCl_3$) δ 1.42 (3H, t, J=7.5 Hz, $CH_3$), 2.94 (2H, q, J=7.4 Hz, $CH_2$), 3.97 (3H, s, $CH_3$), 5.73 (2H, s, $CH_2$), 6.99 (1H, s, Ar—H), 7.79 (1H, m, Ar—H), 7.95 (1H, m, Ar—H), 8.08 (1H, s, Ar—H), 8.27 (1H, d, J=7.8 Hz, Ar—H), 8.70 (1H, d, J=7.8 Hz, Ar—H); MS ($ES^+$) m/e 377 $[MH]^+$; Anal. Found. C, 55.55; H, 4.16; N, 28.38. $C_{18}H_{16}N_8O_2$. $0.2CH_2Cl_2$ requires C, 55.57; H, 4.20; N, 28.49%.

EXAMPLE 107

3-(5-Ethylisoxazol-3-yl)-6-(pyrazin-2-yl)methyloxy-1,2,4-triazolo[3 4-a]phthalazine The title-compound was prepared from 6-hydroxy-3-(5-ethylisoxazol-3-yl)-1,2,4-triazolo[3,4-a]phthalazine (prepared from 6-chloro-3-( 5-ethylisoxazol-3-yl)-1,2,4-triazolo[3,4-a]phthalazine, Example 105 part c, using conditions described for the preparation of Intermediate 2) and 2-chloromethylpyrazine (prepared as described in Example 15 part a) using the procedure described in Example 15 part b, $^1$H NMR (360 MHz, $CDCl_3$) δ 1.42 (3H, t, J=7.6 Hz, $CH_3$), 2.94 (2H, q, J=7.6 Hz, $CH_2$), 5.83 (2H, s, $CH_2$), 6.84 (1H, s, Ar—H), 7.84 (1H, m, Ar—H), 7.98 (1H, m, Ar—H), 8.30 (1H, d, J=7.9 Hz, Ar—H), 8.60–8.64 (2H, m, 2 of Ar—H), 8.70 (1H, m, Ar—H), 9.15 (1H, d, J=1.3 Hz, Ar—H); MS ($ES^+$) m/e 374 $[MH]^+$; Anal. Found. C, 61.16; H, 3.79; N, 26.19. $C_{19}H_{15}N_7O_2$ requires C, 61.12; H, 4.05; N, 26.26%.

EXAMPLE 108

6-(1-Ethyl-1,2,3-triazol-4v)methyloxy-3-(3-isoxazolyl)-1,2,4-triazolo[3,4-a]phthalazine The title-compound was prepared from 6-chloro-3-(3-isoxazolyl)-1,2,4-triazolo[3,4-a]phthalazine (prepared as described in Example 34, step b) and 4-hydroxymethyl-1-ethyl-1,2,3-triazole (prepared as described in Example 98 part a), following the procedure described in Example 98, but performing the reaction at −450° C. $^1$H NMR (360 MHz, $CDCl_3$) δ 1.55 (3H, t, J=7.5 Hz, $CH_3$), 4.40 (2H, q, J=7.4 Hz, $CH_2$), 5.78 (2H, s, $CH_2$), 7.31 (1H, d, J=1.7 Hz, Ar—H), 7.82 (1H, m, Ar—H), 7.95 (1H, m, Ar—H), 8.27 (1H, d, J=7.8 Hz, Ar—H), 8.64–8.66 (2H, m, 2 of Ar—H), 8.69 (1H, s, Ar—H); MS ($ES^+$) m/e 363 $[MH]^+$; Anal. Found. C, 56.24; H, 3.70; N, 30.65. $C_{17}H_{14}N_8O_2$ requires C, 56.35; H, 3.89; N, 30.92%.

EXAMPLE 109

6-(1-Ethyl-1,2,4-triazol-3-yl)methyloxy-3-(3-isoxazolyl)-1,2,4-triazolo[3,4-a]phthalazine a) 3-(3-Isoxazolyl)-6-[2-{[2-(trimethylsilyl)ethoxy]methyl}-1,2,4-triazol-3-yl]methyloxy-1,2,4-triazolo[3,4-a]phthalazine The title-compound was prepared from 6-chloro-3-(3-isoxazolyl)-1,2,4-triazolo[3,4-a]phthalazine (described in Example 34, part b) and 3-(hydroxymethyl)-2-{[2-(trimethylsilyl)ethoxy]methyl}-1,2,4-triazole (described in Example 45, part c) following the procedure described in Example 45, part d, $^1$H NMR (360 MHz, $CDCl_3$) δ 0.00 (9H, s, 3 of $CH_3$), 0.88 (2H, q, J=8.4 Hz, $CH_2$), 3.67 (2H; t, J=8.3 Hz, $CH_2$), 5.84 (2H, s, $CH_2$), 5.92 (2H, s, $CH_2$), 7.30 (1H, d, J=1.7 Hz, Ar—H), 7.89 (1H; t, J=7.1 Hz, Ar—H), 7.96 (1H, s, Ar—H), 8.02 (1H, t, J=7.6 Hz, Ar—H), 8.32 (1H, d, J=8.2 Hz, Ar—H), 8.70 (1H, s, Ar—H), 8.75 (1H, d, J=8.2 Hz, Ar—H).

b) 3-(3-Isoxazolyl)-6-(1,2,4-triazol-3-yl)methyloxy-1,2,4-triazolo[3,4-a]phthalazine The title-compound was prepared from the preceding phthalazine using the procedure in Example 46, 1H NMR (250 MHz, $d^4$-MeOH) δ 5.73 (2H, s, $CH_2$), 7.48 (1H, s, Ar—H), 7.95 (1H, m, Ar—H), 8.05–8.07 (2H, m, 2 of Ar—H), 8.38 (1H, m, Ar—H), 8.60 (1H, m, Ar—H), 8.99 (1H, s, Ar—H).

c) 6-(1-Ethyl-1,2,4-triazol-3-yl)methyloxy-3-(3-isoxazolyl -1,2,4-triazolo[3,4-a]phthalazine The title compound was prepared from the preceding phthalazine and iodoethane using the procedure described in Example 47 at −40° C., $^1$H NMR (360 MHz, $CDCl_3$) δ 1.56 (3H, t, J=7.4 Hz, $CH_3$), 4.24 (2H, q, J=7.4 Hz, $CH_2$), 5.73 (2H, s, $CH_2$), 7.41 (1H, d, J=1.7 Hz, Ax-H), 7.79 (1H, t, J=7.6 Hz, Ar—H), 7.96 (1H, t, J=8.3 Hz, Ar—H), 8.11 (1H, s, Ar—H), 8.28 (1H, d, J=8.2 Hz, Ar—H), 8.73 (1H, d, J=1.7 Hz, Ar—H), 8.76 (1H, d, J=8.2 Hz, Ar—H); MS (ES$^+$) m/e 363 [MH]$^+$.

EXAMPLE 110

6-(1-Ethyl-1,2,3-triazol-5-yl)methyloxy-3-(3-isoxazolyl)-1,2,4-triazolo[3,4-a]phthalazine The title-compound was prepared from 6-chloro-3-(3-isoxazolyl) 1,2,4-triazolo[3,4-a]phthalazine (prepared as described in Example 34 step b) and 5-hydroxymethyl-1-ethyl-1,2,3-triazole (prepared as described in Example 97 part b), following the procedure given for Example 71 but performing the reaction at −456° C.; $^1$H NMR (360 MHz, CDCl$_3$) δ 1.62 (3H, t, J=7.2 Hz, CH$_3$), 4.58 (2H, q, J=7.3 Hz, CH$_2$), 5.81 (2H, s, CH$_2$), 7.25 (1H, d, J=1.8 Hz, Ar—H), 7.84 (1H, m, Ar—H), 7.99 (1H, m, Ar—H), 8.08 (1H, s, Ar—H), 8.14 (1H, d, J=7.8 Hz, Ar—H), 8.66 (1H, d, J=1.8 Hz, Ar—H), 8.72 (1H, d, J=7.8 Hz, Ar—H); MS (ES$^+$) m/e 363 [MH]$^+$; Anal. Found. d, 56.47; H 3.68; N, 30.82. C$_{17}$H$_{14}$N$_8$O$_2$ requires C, 56.35; H, 3.89; N, 30.92%.

EXAMPLE 111

6-(1-Ethylimidazol-4-yl)-4-(3-isoxazolyl)methyloxy-1,2,4-triazolo[3,4-a]phthalazine The title-compound was prepared from 6-chloro-3-(3-isoxazolyl)-1,2,4-triazolo[3,4a]phthalazine (described in Example 34, part c) and 1-ethylimidazole-4-methanol using the conditions described in Example 98, $^1$H NMR (360 MHz, CDCl$_3$) δ 1.45 (3H, t, J=7.3 Hz, CH$_3$), 3.96 (2H, q, J=7.3 Hz, CH$_2$), 5.62 (2H, s, CH$_2$), 7.31 (1H, d, J=1.7 Hz, Ar—H), 7.47 (1H, d, J=1.1 Hz, Ar—H), 7.67 (1H, d, J=1.1 Hz, Ar—H), 7.78 (1H, t, J=8.6 Hz, Ar—H), 7.92 (1H, t, J=6.4 Hz, Ar—H), 8.28 (1H, d, J=8.1 Hz, Ar—H), 8.70–8.73 (2H, m, 2 of Ar—H); MS (ES$^+$) m/e 362 [MH]$^+$.

EXAMPLE 112

6-(2-Ethyl-1,2,4-triazol-3-yl)-3-(3-isoxazolyl)methyloxy-1,2,4-triazolo[3,4-a]phthalazine a) 2-Ethyl-1,2,4-triazole-3-methanol To a solution of 1,2,4-triazole (10 g, 0.145 mol) in N,N-dimethylformamide (150 ml) under nitrogen at room temperature was added sodium hydride (6.4 g of a 60% dispension in oil, 0.16 mol). The mixture was stirred for 0.5 h and cooled to 0° C. Iodoethane (14 ml, 0.174 mol) was added and stirred for 1 h at room temperature. The solvent was removed in vacuo and the residue dissolved in ethyl acetate (300 ml) and washed with water (3×10 ml). The organic layer was dried (MgSO$_4$) and evaporated in vacuo, and the crude product purified by vacuum distillation (bp 120° C. at 20 mmHg) to give the ethylated triazole (7.49 g, 41%). A solution of this material (2.4 g, 0.025 mol) in tetrahydrofuran (35 ml) at −40° C. under nitrogen was treated with n-butylithium (16.24 ml of a 1.6M solution in hexane, 0.026 mol) over 0.25 h. After 0.25 h, N,N-dimethylformamide (2.03 ml, 0.026 mol) was added and the mixture allowed to warm to room temperature over 2 h. Sodium borohydride (1.0 g, 0.03 mol) and methanol (20ml) were added and the reaction mixture stirred for 12 h. The solvent was evaporated in vacuo and the crude material mixed with water (50 ml) and extracted into dichloromethane (6×5ml). The combined organic extracts were dried (MgSO$_4$) evaporated in vacuo and the residue purified by chromatography on silica gel, eluting with 0–5% methanol/dichloromethane (gradient elution), to give the title-compound (0.5 g, 16%), $^1$H NMR (360 MHz, CDCl$_3$) δ 1.47 (3H, t, J=7.3 Hz, CH$_3$), 4.24 (2H, q, J=7.3 Hz, CH$_2$), 4.75 (2H, s, CH$_2$), 5.14 (1H, br s, OH), 7.26 (1H, s, Ar—H).

b) 6-(2-Ethyl-1,2,4triazol-3-yl)-3-(3-isoxazolyl)methyloxy-1,2,4-triazolo[3,4-a]phthalazine The title-compound was prepared from 6-chloro-3-(3-isoxazolyl)-1,2,4-triazolo[3,4-a]phthalazine (described in Example 34, part c) and 2-ethyl-1,2,4-triazole-3-methanol using the conditions described in Example 71 at −40° C., $^1$H NMR (360 MHz, CDCl$_3$) δ 1.52 (3H, t, J=7.2 Hz, CH$_3$), 4.43 (2H, q, J=7.3 Hz, CH$_2$), 5.85 (2H, s, CH$_2$), 7.29 (1H, d, J=1.7 Hz, Ar—H), 7.83 (1H, t, J=7.3 Hz, Ar—H), 7.95–8.01 (2H, m, 2 of Ar—H), 8.21 (1H, d, J=8.1 Hz, Ar—H), 8.70 (1H, d, J=1.7 Hz, Ar—H), 8.76 (1H, d, J=8.1 Hz, Ar—H); MS (ES$^+$) m/e 363 [MH]$^+$.

EXAMPLE 113

3-(3-Isoxazolyl)-6-(2-propyl-1,2,4-triazol-3-yl)methlox-1,2,4-triazolo[3,4-a]phthalazine The title-compound was prepared from 6-chloro-3-(isoxazol-3-yl)-1,2,4-triazolo[3,4-a]phthalazine (described in Example 34 part b) and 2-propyl-3-hydroxymethyl-1,2,4-triazole prepared as described in WO-A-9804559 using the procedure given for Example 71, $^1$H NMR (360 MHz, CDCl$_3$) δ 0.95 (3H, t, J=7.4 Hz, Ar—H), 1.91–2.01 (2H, m, CH$_2$), 4.34 (2H, t, J=7.0 Hz, CH$_2$), 5.85 (2H, s, CH$_2$), 7.28 (1H, d, J=1.7 Hz, Ar—H), 7.83 (1H, t, J=8.3 Hz, Ar—H), 7.96–8.01 (2H, m, 2 of Ar—H), 8.21 (1H, d, J=7.9 Hz, Ar—H:), 8.62 (1H, s, Ar—H), 8.70 (1H, d, J=7.1 Hz, Ar—H); MS (ES$^+$) m/e 377 [MH]$^+$; Anal. Found. C, 57.12; H, 3.87; N, 29.49. C$_{18}$H$_{16}$N$_8$O$_2$. 0.05CH$_2$Cl$_2$ requires C, 56.96; H, 4.26; N, 29.44%.

EXAMPLE 114

3-(3-Isoxazolyl)-6-(1-propyl-1,2,4-triazol-3-yl)methyloxy-1,2,4-triazolo[3,4-a]phthalazine The title-compound was prepared from 6-chloro-3-(isoxazol-3-yl)-1,2,4-triazolo[3,4-a]phthalazine (described in Example 34 part b) and 1-propyl-3-hydroxymethyl-1,2,4-triazole prepared as described in WO-A-9804559 using the procedure given for Example 71, $^1$H NMR (360 MHz, CDCl$_3$) δ 0.95 (3H, t, J=7.4 Hz, CH$_3$), 1.89–1.99 (2H, m, CH$_2$), 4.15 (2H, t J=7.0 Hz, CH$_2$), 5.73 (2H, s, CH$_2$), 7.40 (1H, d, J=1.7 Hz, Ar—H), 7.80 (1H, t, J=7.2 Hz, Ar—H), 7.96 (1H, t, J=6.9 Hz, Ar—H), 8.09 (1H, s, Ar—H), 8.28 (1H, d, J=7.9 Hz, Ar—H), 8.70 (1H, s, Ar—H), 8.74 (1H, d, J=7.7 Hz, Ar—H); MS (ES$^+$) m/e 377 [MH]$^+$.

EXAMPLE 115

6-(1-Benzylimidazol-2-yl)methyloxy-3-(3-isoxazolyl)-1,2,4-triazolo[3,4-a]phthalazine The title-compound was prepared from Intermediate 5 and 1-benzyl-2-(hydroxymethyl)imidazole in a similar manner to Example 98, mp 197.5–198.5° C.; $^1$H NMR (250 MHz, CDCl$_3$) δ 5.39 (2H, s, CH$_2$), 5.78 (2H, s, CH$_2$), 6.92–7.19 (7H, m, 7 of ArH), 7.31 (1H, d, J=1.7 Hz, ArH), 7.67 (1H, m, ArH), 7.84 (1H, d, J=7.9 Hz, ArH), 7.91 (1H, m, ArH), 8.63 (1H, d, J=10.0 Hz, ArH), 8.65 (1H, d, J=1.7 Hz, ArH); MS (ES$^+$) m/e 424 [MH]$^+$.

EXAMPLE 116

3-(5-Methoxymethylisoxazol-3-yl)-6-(1-methyl-1,2,4-triazol-3-yl)methyloxy-1,2,4-triazolo[3,4a]phthalazine a) 3-(5-Methoxymethylisoxazol-3-yl)-6-(2,2,2-trifuoroethyloxy)-1,2,4-triazolo[3,4-a]phthalazine A solution of triethylamine (1.0 g, 10.2 mmol) in dichloromethane (50 ml) was added dropwise to a suspension of Intermediate 4 (1 g, 2.9 mmol) and methyl propargyl ether (0.812 g, 11.6 mmol) in dichloromethane (50 ml). After 1 h, the solvent was evaporated in vacuo and the residue dissolved in ethyl acetate, washed with water, dried (MgSO$_4$) and evaporated in vacuo. The crude product was purified by chromatography on silica gel, eluting with 10–40% ethyl acetate/dichloromethane (gradient elution) followed by recrystallisation from ethyl acetate to give the title compound (230 mg, 21%), $^1$H NMR (250 MHz, CDCl$_3$) δ 3.52 (3H, s, CH$_3$), 4.70 (2H, s, CH$_2$O), 5.03 (2H, q, J=8.1 Hz, CH$_2$CF$_3$), 7.11 (1H, s, Ar—H), 7.90 (1H, m, ArH), 8.04 (1H, m, ArH), 8.28 (1H, d, J=7.9 Hz, ArH), 8.74 (1H, d, J=7.5 Hz, ArH); MS (ES$^+$) m/e 380 [MH]$^+$.

b) 3-(5-Methoxymethylisoxazol-3-yl)-6-(1-methyl-1,2,4-triazol-3-yl)methyloxy-1,2,4-triazolo[3,4-a]phthalazine The title-compound was prepared from the preceding phthalazine and 1-methyl-1,2,4-triazole-3-methanol (prepared using the conditions of Itoh and Okongi, EP-A-421210) in a similar manner to Example 98, mp 235.5–236.5° C.; $^1$H NMR (360 MHz, CDCl$_3$) δ 3.51 (3H, s, CH$_3$), 3.97 (3H, s, CH$_3$), 4.71 (2H, s, CH$_2$), 5.72 (2H, s, CH$_2$), 7.29 (1H, s, ArH), 7.80 (1H, m, ArH), 7.96 (1H, m, ArH), 8.08 (1H, s, ArH), 8.29 (1H, d, J=7.7 Hz, ArH), 8.71 (1H, d, J=7.2 Hz, ArH); MS (ES$^+$) m/e 393 [MH]$^+$; Anal. Found. C, 55.47; H, 4.01; N, 28.30. C$_{18}$H$_{16}$N$_8$O$_3$ requires C, 55.10; H, 4.11; N, 28.56%.

EXAMPLE 117

3-(5-Methoxymethylisoxazol-3-yl)-6-(2-methyl-1,2,4-triazol-3-yl)methyloxy-1,2,4-triazolo[3,4-a]phthalazine The title-compound was prepared from the product of Example 116 part a and 1-methyl-1,2,4-triazole-5-methanol (prepared using the conditions of Itoh and Okongi, EP-A-421210) in a similar manner to Example 98, mp 206–207.56° C.; $^1$H NMR (360 MHz, CDCl$_3$) δ 3.53 (3H, s, CH$_3$), 4.12 (3H, s, CH$_3$), 4.73 (2H, s, CH$_2$), 5.87 (2H, s, CH$_2$), 7.20 (1H, s, ArH), 7.42 (1H, s, ArH), 7.93 (1H, m, ArH), 8.06 (1H, m, ArH), 8.30 (1H, d, J=7.7 Hz, ArH), 8.70 (1H, d, J=7.2 Hz, ArH); MS (ES$^+$) m/e 393 [MH]$^+$.

EXAMPLE 118

3-(5-Methoxyisoxazol-3-yl)-6-(1-methylimidazol-4-yl)methyloxy-1,2,4-triazolo[3,4-a]phthalazine a) 3-(5-Methoxyisoxazol-3-yl)-6-(4-toluenesulphonyloxy)-1,2,4-triazolo[3,4-a]phthalazine Sodium methoxide (165 mg, 0.3 mmol) was added to a stirred suspension of 3-(5-chloroisoxazol-3-yl)-6-hydroxy-1,2,4-triazolo[3,4-a]phthalazine (400 mg, 0.14 mmol) (prepared from Intermediate 7 using the procedure described in Example 15 part b) in N,N-dimethylformamide (20 ml) at 0° C. under nitrogen. The mixture was stirred at 0° C. for 3 h then water was added (6 ml) and the solvents evaporated in vacuo. The residue was taken up in water and acidified to pH 2 using 2M hydrochloric acid. The resulting precipitate was filtered off, washed with hexane and azeotroped with ethanol to give crude 6-hydroxy-3(5-methoxyisoxazol-3-yl)-1,2,4-triazolo[3,4-a]phthalazine, MS (ES$^+$) 284 [MH]$^+$. The title-compound was prepared from this material using the procedure described in Example 103 part a, $^1$H NMR (250 MHz, CDCl$_3$) δ 2.49 (3H, s, CH$_3$), 4.15 (3H, s, CH$_3$), 6.10 (1H, s, Ar—H), 7.45 (2H, d, J=8.5 Hz, Ar—H), 7.92 (1H, m, Ar—H), 8.06 (1H, m, Ar—H), 8.26–8.32 (3H, m, 3 of Ar—H), 8.64 (1H, d, Ar—H); MS (ES$^+$) 438 [MH]$^+$.

b) 3-(5-Methoxyisoxazol-3-yl)-6-(1-methylimidazol-4-yl)methyloxy-1,2,4-triazolo[3,4-a]phthalazine The title-compound was prepared from the preceding compound and 4-hydroxymethyl-1-methylimidazole using the conditions described for Example 98, $^1$H NMR (360 MHz, CDCl$_3$) δ 3.68 (3H, s, CH$_3$), 4.14 (3H, s, CH$_3$), 5.61 (2H, s, CH$_2$), 6.18 (1H, s, Ar—H), 7.41 (1H, s, Ar—H), 7.60 (1H, s, Ar—H), 7.77 (1H, m, Ar—H), 7.91 (1H, m, Ar—H), 8.26 (1H, d, J=8.5 Hz, Ar—H), 8.64 (1H, d, J=8.5 Hz, Ar—H); MS (ES$^+$) 378 [MH]$^+$; Anal. Found. C, 55.86; H, 3.81; N, 24.93. C$_{18}$H$_{15}$N$_7$O$_3$. 0.15 CH$_2$Cl$_2$ requires C, 55.88; H, 3.95; N, 25.13%.

EXAMPLE 119

3-(5-Methoxyisoxazol-3-yl)-6-(1-methyl-1,2,4-triazol-3-yl)methyloxy-1,2,4-triazolo[3,4-a]phthalazie The title-compound was prepared from 3-(5-methoxyisoxazol-3-yl)-6-(4toluenesulphonyloxy)-1,2,4triazolo[3,4a]phthalazine (prepared as described in Example 118 part a) and 3-hydroxymethyl-1-methyl-1,2,4-triazole (prepared using the conditions of Itoh and Okongi, EP-A-421210) using the conditions given for in Example 98, $^1$H NMR (360 MHz, CDCl$_3$) δ 3.96 (3H, s, CH$_3$), 4.15 (3H, s, CH$_3$), 5.72 (2H, s, CH$_2$), 6.30 (1H, s, Ar—H), 7.79 (1H, m, Ar—H), 7.95 (1H, m, Ar—H), 8.07 (1H, s, Ar—H), 8.28 (1H, d, J=8.4 Hz, Ar—H), 8.68 (1H, d, J=8.4 Hz, Ar—H); MS (ES$^+$) m/e 379 [MH]$^+$; Anal. Found. C, 53.97; H, 3.73; N, 29.62. C$_{17}$H$_{14}$N$_8$O$_3$ requires C, 54.04; H, 3.48; N, 29.32%.

EXAMPLE 120

3-(3-Methylisoxazol-5-yl)-6-(2-pyridyl)methyloxy-1,2,4-triazolo[3,4-a]phthalazine a) 6-Chloro-3-(3-(3-methylisoxazol-5-yl)-1,2,4-triazolo[3,4-a]phthalazine The title-compound was prepared from 3-methyl-5-isoxazole carboxylic acid (*Eur. J. Med Chem.*, 1992, 27, 581) using the procedure described for Intermediate 1, step c, $^1$H NMR (250 MHz, GDCl$_3$) δ 2.50 (3H, s, CH$_3$), 7.22 (1H, s, Ar—H), 8.00 (1H, m, Ar—H). 8.10 (1H, m, Ar—H), 8.36 (1H, d, J=8.2 Hz, Ar—H), 8.84 (1H, m, Ar—H); MS (ES$^+$) m/e 286 [M]$^+$.

b) 3-(3-Methylisoxazol-5-yl)-6-(2-pyridyl)methyloxy-1,2,4-triazolo[3,4-a]phthalazine The title-compound was prepared from the preceding product and 2-pyridylcarbinol using the procedure given for Example 1, $^1$H NMR (360 MHz, CDCl$_3$/d$^6$-DMSO) δ 2.48 (3H, s, CH$_3$), 5.78 (2H, s, CH$_2$), 7.05 (1H, s, Ar—H), 7.34 (1H, m, Ar—H), 7.65 (1H, d, J=7.8 Hz, Ar—H), 7.79–7.90 (2H, m, 2 of Ar—H), 8.01 (1H, m, Ar—H), 8.36 (1H, d, J=7.9 Hz, Ar—H), 8.68–8.72 (2H, m, 2 of Ar—H); MS (ES$^+$) m/e 359 [MH]$^+$; Anal. Found. C, 63.04; H, 3.63; N, 22.89. C$_{19}$H$_{14}$N$_6$O$_2$. 0.25H$_2$O requires C, 62.89; H, 4.03; N, 23.16%.

EXAMPLE 121

3-(3-Methylisoxazol-5-yl)-6-(6-methylpyridin-2-yl)methyloxy-1,2,4-triazolo[3,4-a]phthalazine The title-compound was prepared from the product of Example 120, step a, and 6-methyl-2-pyridylcarbinol using the procedure given for Example 1, $^1$H NMR (360 MHz, CDCl$_3$) δ 2.48 (3H, s, CH$_3$), 2.64 (3H, s, CH$_3$), 5.74 (2H, s, CH$_2$), 7.07 (1H, s, Ar—H), 7.18 (1H, d, J=7.7 Hz, Ar—H), 7.44 (1H, d, J=7.6 Hz, Ar—H), 7.69 (1H, t, J=7.7 Hz, Ar—H), 7.85 (1H, m, Ar—H), 7.99 (1H, m, Ar—H), 8.35

(1H, d, J=8.6 Hz, Ar—H), 8.71 (1H, d, Ar—H); MS (ES⁺) m/e 373 [MH]⁺.

EXAMPLE 122

3-(3-Methylisoxazol-5-yl)-6-(pyrazin-2-yl)methyloxy-1,2,4-triazolo[3,4-a]phthalazine The title-compound was prepared from 6-hydroxy-3-(3-methylisoxazol-5-yl)-1,2,4-triazolo[3,4-a]phthalazine (generated from the product of Example 120 part a using the conditions described for the preparation of Intermediate 2) and 2-chloromethylpyrazine (prepared as described in Example 15 part a) using the procedure described in Example part b. ¹H NMR (360 MHz, CDCl₃) δ 2.48 (3H, s, CH₃), 5.83 (2H, s, CH₂), 7.03 (1H, s, Ar—H), 7.87 (1H, m, Ar—H), 8.01 (1H, m, Ar—H), 8.32 (1H, d, J=7.8 Hz, Ar—H), 8.62–8.68 (2H, m, 2 of Ar—H), 8.72 (1H, d, J=7.8 Hz, Ar—H), 8.99 (1H, s, Ar—H); MS (ES⁺) m/e 360 [MH]⁺; Anal. Found C, 60.24; H, 3.44; N, 27.03. C₁₈H₁₃N₇O₂ requires C, 60.16; H, 3.63; N, 27.28%.

EXAMPLE 123

3-(3-Methylisoxazol-5-yl)-6-(2-methyl-1,2,4-triazol-3-yl)methyloxy-1,2,4-triazolo[3,4-a]phthalazine The title-compound was prepared from the product of Example 120 part a and 2-methyl-1,2,4-triazole-3-methanol (prepared using the conditions of Itoh and Okongi, EP-A-42120) following the procedure given for Example 98, ¹H NMR (400 MHz, CDCB) δ 2.43 (3H, s, CH₃), 4.16 (3H, s, CH₃), 5.82 (2H, s, CH₂), 7.07 (1H, s, Ar—H), 7.84 (1H, m, Ar—H), 7.95–8.04 (2H, m, 2 of Ar—H), 8.21 ilH, d, J=8.0 Hz, Ar—H), 8.62 (1H, d, J=8.0 Hz, Ar—H); MS(ES⁺) m/e 363 [MH]⁺; Anal. Found. C, 56.12; H, 3.90; N, 30.74. C₁₇H₁₄N₈O₂ requires C, 56.35; H, 3.89; N, 30.92%.

EXAMPLE 124

3-(3-Methylisoxazol-5-yl)-6-(1-methyl-1,2,4-triazol-3-yl)methyloxy-1,2,4-triazolo[3. 4-a]phthalazine The title-compound was prepared from the product of Example 120 part a and 3-hydroxymethyl-1-methyl-1,2,4-triazole (prepared using the conditions of Itoh and Okongi, EP-A-421210) following the conditions described for Example 71, mp 270–271.5° C.; ¹H NMR (360 MHz, CDCl₃) δ 2.50 (3H, s, CH₃), 3.97 (3H, s, CH₃), 5.73 (2H, s, CH₂), 7.31 (1H, s, Ar—H), 7.82 (1H, m, Ar—H), 7.97 (1H, m, Ar—H), 8.09 (1H, s, Ar—H), 8.31 (1H, d, J=8.6 Hz, Ar—H), 8.70 (1H, d, J=8.6 Hz, Ar—H); MS (ES⁺) m/e 363 [MH]⁺; Anal. Found. C, 55.92; H, 3.63; N, 30.16. C₁₇H₄N₈O₂. 0.06CH₂Cl₂ requires C, 55.77; H, 3.87, N, 30.49%.

EXAMPLE 125

3-(3-Ethoxyisoxazol-5-yl)-6-(1-methyl-1,2,4-triazol-3-yl)methyloxy-1,2,4-triazolo[3,4-a]phthalazine
a) Methyl (3-hydroxy)isoxazole-5-carboxylate To a solution of N-hydroxyurea (3.80 g, 0.05 mol) and diazabicyclo[5.4.0]undec-7-ene (8.37 g, 0.055 mol) in methanol (50 ml) at 0° C. under nitrogen was added dimethylacetylene dicarboxylate (7.10 g, 0.05 mol). The reaction was stirred at 0° C. for 1 h then at room temperature for 12 h. The solvent was evaporated in vacuo and the residue taken up into water (20 ml) and acidified to pH 1 with concentrated hydrochloric acid. The mixture was extracted with diethyl ether (3×25 ml), dried (Na₂SO₄) and evaporated in vacuo. The resulting solid was recrystallised from chloroform to give the title-ester (2.20 g, 31%), ¹H NMR (250 MHz, CDCl₃) δ 3.97 (3H, s, CH₃), 6.61 (1H, s, Ar—H).
b) Methyl (3-ethoxy)isoxazole-5-carboxylate To a stirred solution of the preceding ester (2.20 g, 0.015 mol) in N,N-dimethylformamide (50 ml) at 0° C. under nitrogen was added sodium hydride (0.74 g of a 60% dispersion in oil, 0018 mol). After 0.5 h, iodoethane (2.4 ml, 0.03 mol) was added dropwise and the reaction mixture allowed to warm to room temperature and stirred for 24 h. The solvent was evaporated in vacuo and the residue dissolved in ethyl acetate (100 ml) and washed with water (3×75 ml). The organic layer was dried (MgSO₄) evaporated in vacuo and the crude product purified by chromatography on silica gel, eluting with ethyl acetate/hexane (2:3), to give the title-compound (2.20 g, 84%), ¹H NMR (250 MHz, CDCl₃) δ 1.43 (3H, t, J=7.0 Hz, CH₃), 3.94 (3H, s, CH₃), 4.33 (2H, q, J=7.1 Hz, CH₂), 6.52 (1H, d, J=2.3 Hz, Ar—H).
c) 3-Ethoxyisoxazole-5-carboxylic acid To a solution of the preceding ester (2.20 g, 0.013 mol) in methanol (10 ml) at room temperature was added a solution of sodium hydroxide (2.06 g, 0.051 mol) in water (15 ml). The mixture was stirred for 1 h then cooled to 0° C. and acidified to pH1 with concentrated hydrochloric acid. The resulting white solid was filtered off to give the title-acid (1.5 g, 75%), ¹H NMR (250 MHz, CDCl₃) δ 1.44 (3H, t, J=4.9 Hz, CH₃), 4.38 (2H, q, J=4.9 Hz, CH₂), 6.63 (1H, s, Ar—H), 6.74 (1H, br s, OH).
d) 6-Chloro-3-(3-ethoxyisoxazol-5-yl-1,2,4-triazolo[3,4-a]phthalazine The title-compound was prepared from 1-chloro-4-hydrazinophthalazine and the preceding acid in a similar manner to that described for Intermediate 1 part c, ¹H NMR (360 MHz, CDCl₃) δ 1.50 (3H, t, J=7.1 Hz, CH₃), 4.43 (2H, q, J=7.1 Hz, CH₂), 6.97 (1H, s, Ar—H), 7.96 (1H, t, J=8.3 Hz, Ar—H), 8.09 (1H, t, J=8.3 Hz, Ar—H), 8.34 (1H, d, J=7.6 Hz, Ar—H), 8.81 (1H, d, J=7.6 Hz, Ar—H).
e) 3-(3-Ethoxyisoxazol-5-yl]-6-(1-methyl-1,2,4-triazol-3-yl)methyloxy-1,2,4-triazolo[3,4-a]phthalazine The title-compound was prepared from the preceding phthalazine and 1-methyl-1,2,4-triazole-3-methanol (prepared using the conditions of Itoh and Okongi, EP-A-421210) following the procedure given in Example 71, ¹H NMR (360 MHz, CDCl₃) δ 1.49 (3H, t, J=7.1 Hz, CH₃), 3.97 (3H, s, CH₃), 4.46 (2H, q, J=7.1 Hz, CH₂), 5.70 (2H, s, CH₂), 7.10 (1H, s, Ar—H), 7.81 (1H, t, J=8.4 Hz, Ar—H), 7.96 (1H, t, J=8.3 Hz; Ar—H), 8.08 (1H, s, Ar—H), 8.30 (1H, d, J=8.1 Hz, Ar—H), 8.7Q (1H, d, J=8.1 Hz, Ar—H); MS (ES⁺) m/e 393 [MH]⁺.

EXAMPLE 126

6-(2-Methyl-1,2,4-triazol-3-yl)methyloxy-3-(Pyrazin-2-yl)-1,2,4-triazolo[3,4-a]phthalazine
a) 6-Chloro-3-(pyrazin-2-yl)-1,2,4-triazolo[3,4-a]phthalazine The title-compound was prepared from 1-chloro-4-hydrazinophthalazine and pyrazine-2-carboxylic acid as described for Intermediate 1 part c, ¹H NMR (250 MHz, CDCl₃) δ 7.99 (1H, t, J=7.2 Hz, Ar—H), 8.09 (1H, t, J=8.2 Hz, Ar—H), 8.33 (1H, d, J=6.8 Hz; Ar—H), 8.80 (1H, m, Ar—H), 8.82–8.88 (2H, m, 2 of Ar—H), 9.67 (1H, d, J=1.5 Hz, Ar—H).
b) 6-(2-Methyl-1,2,4-triazol-3-yl)methyloxy-3-(pyrazin-2-yl)-1,2,4-triazolo[3,4-a]phthalazie The title-compound was prepared from the preceding phthalazine and 2-methyl-1,2,4-triazole-3-methanol (prepared using the conditions of Itoh and Okongi, EP-A-421210) following the procedure given for Example 98, $^1$H NMR (360 MHz, CDCl$_3$) δ 4.06 (3H, s, CH$_3$), 5.97 (2H, s, CH$_2$), 7.83 (1H, t, J=7.5 Hz, Ar—H), 8.00–8.02 (2H, m, 2 of Ar—H), 8.19 (1H, d, J=8.5 Hz, Ar—H), 8.77–8.81 (2H, m, 2 of Ar—H), 8.82 (1H, s, Ar—H), 9.65 (1H, s, Ar—H); MS (ES$^+$) m/e 360[MH]$^+$.

EXAMPLE 127

3-Prazin-2-yl)-6-(pyrid-2-yl)methyloxy-1,2,4-triazolo[3,4-a]phthalazine

The title-compound was prepared from 6-chloro-3-(pyrazin-2-yl)-1,2,4-triazolo[3,4-a]phthalazine and 2-pyridylcarbinol using the procedure given for Example 98, $^1$H NMR (360 MHz, CDCl$_3$) δ 5.77 (2H, s, CH$_2$), 7.40 (1H, t, J=6.6 Hz, Ar—H), 7.71 (1H, d, J=7.8 Hz, Ar—H), 7.95–8.00 (2H, m, 2 of Ar—H), 8.08 (1H, t, J=7.6 Hz, Ar—H), 8.40 (1H, d, J=8.0 Hz, Ar—H), 8.70 (2H, m, 2 of Ar—H), 8.78 (1H, m, Ar—H), 8.88 (1H, s, Ar—H), 9.58 (1H, s, Ar—H); MS (ES$^+$) m/e 356 [MH]$^+$.

EXAMPLE 128

3-(5-Methyl-1,2,4-oxadiazol-3-yl)-6-(1-methyl-1,2,4-triazol-3-yl)methyloxy-1,2,4-triazolo[3,4-a]phthalazine a) 3-Carboxamidoxime-6-(2,2,2-trifluoroethyloxy)-1,2,4-triazolo[3,4-a]phthalazine Intermediate 4 (690 mg, 2 mmol) was suspended in ethanol (10 ml) and concentrated ammonium hydroxide (10 ml) was added. The reaction was stirred for 0.5 h and then diluted with ethanol and evaporated. The product was washed successively with water, ethanol and ether and dried to yield the title-product (0.6 g, 92%); $^1$H NMR (250 MHz, d$_6$-DMSO) δ 5.23 (2H, q, J=8.7 Hz), 6.10 (2H, br s), 7.98 (1H, t, J=7.7 Hz), 8.12 (1H, t, J=7.7 Hz), 8.18 (1H, d, J=7.7 Hz), 8.56 (1H, d, J=7.7 Hz), 10.25 (1H, s); (ES$^+$) m/e 327 [MH]$^+$.

b) 3-(5-Methyl-1,2,4-oxadiazol-3-yl)-6-(2,2,2-trifluoroethyloxy-1,2,4-triazolo[3,4-a]phthalazine The preceding amide oxime (0.6 g, 1.8 mmol) in acetic anhydride (10 ml) was heated at reflux for 16 h. The solvent was removed and the residue was azeotroped with xylene. The residue was taken up in dichloromethane, washed with water, dried (MgSO$_4$) and evaporated. The residue was purified by column chromatography on silica gel, eluting with ethyl acetate/dichloromethane, to yield the title-product (0.31 g, 49%), $^1$H NMR (250 MHz, CDCl$_3$) δ 2.79 (3H, s), 5.00 (2H, q, J=8.7 Hz), 7.91 (1H, t, J=7.7 Hz), 8.08 (1H, t, J=7.7 Hz), 8.29 (1H, d, J=7.7 Hz), 8.78 (1H, d, J=7.7 Hz); MS (ES$^+$) 351 [MH]$^+$.

c) 3-(5-Methyl-1,2,4-oxadiazol-3-yl)-6-(1-methyl-1,2,4triazol-3-yl)methyloxy-1,2,4-triazolo[3,4-a]phthalazine The title-compound was prepared from the preceding phthalazine and 1-methyl-1,2,4-triazole-3-methanol (prepared using the conditions of Itoh and Okongi, EP-A-421210) in a similar manner to Example 98, $^1$H NMR (250 MHz, CDCl$_3$) δ 2.78 (3H, s, CH$_3$), 3.99 (3H, s, CH$_3$), 5.74 (2H, s, CH$_2$), 7.81 (1H, m, Ar—H), 7.97 (1H, m, Ar—H), 8.10 (1H, s, Ar—H), 8.28 (1H, d, J=7.7 Hz, Ar—H), 8.74 (1H, d, J=7.5 Hz, Ar—H); MS (ES$^+$) m/e 364 [MH]$^+$.

What is claimed is:

1. A compound of formula III:

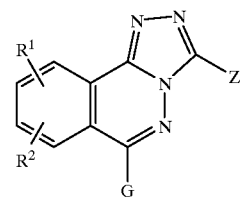

(III)

wherein:

R$^1$ is hydrogen, halogen, CF$_3$, OCF$_3$, CN or a group C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or CF$_3$ groups;

R$^2$ is hydrogen, halogen, CF$_3$, OCF$_3$, CN or a group C$_{1-4}$alkyl, C$_{2-4}$alkenyl, C$_{2-4}$alkynyl, C$_{1-4}$alkoxy, C$_{2-4}$alkenyloxy or C$_{2-4}$alkynyloxy, each of which groups is unsubstituted or substituted with one or two halogen atoms;

Z is a 5-membered heteroaromatic ring containing 1, 2 or 3 heteroatoms independently selected from oxygen, nitrogen and sulphur, at most one of the heteroatoms being oxygen or sulphur and providing that when two of the heteroatoms are nitrogen then an oxygen or sulphur atom is also present and that when one of the atoms is oxygen or sulphur then at least one nitrogen atom is present, or a 6-membered heteroaromatic ring containing 2 or 3 nitrogen atoms, Z being optionally substituted by R$^v$ and/or R$^w$, where R$^v$ is halogen, R$^6$, NR$^7$R$^8$, NR$^7$COR$^8$, CN, furyl, thienyl, phenyl, benzyl, pyridyl or a 5-membered heteroaromatic ring containing at least one nitrogen atom and optionally 1, 2 or 3 other heterotoms independently selected from oxygen, nitrogen and sulphur, at most one of the other heteroatoms being oxygen or sulphur and R$^w$ is R$^6$ or CN;

R$^6$ is C$_{1-6}$alkyl, C$_{2-6}$alkenyl, C$_{2-6}$alkynyl, C$_{3-6}$cycloalkyl, hydroxyC$_{1-6}$alkyl, C$_{1-6}$alkoxy, C$_{2-6}$alkenyloxy, C$_{2-6}$alkynyloxy, C$_{1-6}$alkoxyC$_{1-6}$alkyl, CH$_2$F or CF$_3$;

R$^7$ and R$^8$ are each independently hydrogen, C$_{1-6}$alkyl, C$_{2-6}$alkenyl, C$_{2-6}$alkynyl, C$_{3-6}$cycloalkyl or CF$_3$;

or R$^7$ and R$^8$, together with the nitrogen atom to which they are attached, form a 4–7 membered heteroaliphatic ring containing the nitrogen atom as the sole heteroatom; and G is a leaving group.

2. A compound of formula VIII:

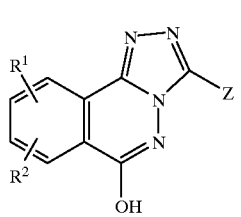

(VIII)

wherein:

$R^1$ is hydrogen, halogen, $CF_3$, $OCF_3$, CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms or with a pyridyl or phenyl ring each of which rings may be unsubstituted or independently substituted by one or two halogen atoms or nitro, cyano, amino, methyl or $CF_3$ groups;

$R^2$ is hydrogen, halogen, $CF_3$, $OCF_3$, CN or a group $C_{1-4}$alkyl, $C_{2-4}$alkenyl, $C_{2-4}$alkynyl, $C_{1-4}$alkoxy, $C_{2-4}$alkenyloxy or $C_{2-4}$alkynyloxy, each of which groups is unsubstituted or substituted with one or two halogen atoms;

Z is a 5-membered heteroaromatic ring containing 1, 2 or 3 heteroatoms independently selected from oxygen, nitrogen and sulphur, at most one of the heteroatoms being oxygen or sulphur and providing that when two of the heteroatoms are nitrogen then an oxygen or sulphur atom is also present and that when one of the atoms is oxygen or sulphur then at least one nitrogen atom is present, or a 6-membered heteroaromatic ring containing 2 or 3 nitrogen atoms, Z being optionally substituted by $R^v$ and/or $R^W$, where $R^v$ is halogen, $R^6$, $NR^7R^8$, $NR^7COR^8$, CN, furyl, thienyl, phenyl, benzyl, pyridyl or a 5-membered heteroaromatic ring containing at least one nitrogen atom and optionally 1, 2 or 3 other heterotoms independently selected from oxygen, nitrogen and sulphur, at most one of the other heteroatoms being oxygen or sulphur and $R^w$ is $R^6$ or CN;

$R^6$ is $C_{1-6}$alkyl, $C_{2-6}$alkenyl, $C_{2-6}$alkyl, $C_{3-6}$cycloalkyl, hydroxy$C_{1-6}$alkyl, $C_{1-6}$alkoxy, $C_{2-6}$alkenyloxy, $C_{2-6}$alkynyloxy, $C_{1-6}$alkoxy$C_{1-6}$alkyl, $CH_2F$ or $CF_3$; and $R^7$ and $R^8$ are each independently hydrogen, $C_{1-6}$alkyl, $C_{2-6}$alkenyl, $C_{2-6}$alkynyl, $C_{3-6}$cycloalkyl or $CF_3$;

or $R^7$ and $R^8$, together with the nitrogen atom to which they are attached, form a 4–7 membered heteroaliphatic ring containing the nitrogen atom as the sole heteroatom.

* * * * *